United States Patent
Li et al.

(10) Patent No.: US 12,378,303 B2
(45) Date of Patent: Aug. 5, 2025

(54) RECOMBINANT COLLAGEN AND PREPARATION METHOD AND USE THEREOF

(71) Applicant: JIANGSU TRAUTEC MEDICAL TECHNOLOGY CO., LTD., Changzhou (CN)

(72) Inventors: Jiajia Li, Changzhou (CN); Liping Wang, Changzhou (CN); Huimin Liu, Changzhou (CN); Wenwen Jiang, Changzhou (CN); Chenming Qian, Changzhou (CN); Pengfei Cheng, Changzhou (CN); Song Qian, Changzhou (CN)

(73) Assignee: JIANGSU TRAUTEC MEDICAL TECHNOLOGY CO., LTD., Changzhou (CN)

( * ) Notice: Subject to any disclaimer, the term of this patent is extended or adjusted under 35 U.S.C. 154(b) by 0 days.

(21) Appl. No.: 18/715,637

(22) PCT Filed: Nov. 23, 2022

(86) PCT No.: PCT/CN2022/133595
§ 371 (c)(1),
(2) Date: May 31, 2024

(87) PCT Pub. No.: WO2023/098523
PCT Pub. Date: Jun. 8, 2023

(65) Prior Publication Data
US 2025/0034233 A1    Jan. 30, 2025

(30) Foreign Application Priority Data
Dec. 3, 2021 (CN) .......................... 202111470250.8

(51) Int. Cl.
C07K 14/78 (2006.01)
C12P 21/02 (2006.01)

(52) U.S. Cl.
CPC .............. C07K 14/78 (2013.01); C12P 21/02 (2013.01)

(58) Field of Classification Search
None
See application file for complete search history.

(56) References Cited

U.S. PATENT DOCUMENTS 5,710,252 A    1/1998 Weber et al.
5,773,249 A *  6/1998 Cappello ............... C12N 15/66
                                              435/69.7

FOREIGN PATENT DOCUMENTS

| | | |
|---|---|---|
| CN | 101316862 A | 12/2008 |
| CN | 106554410 A | 4/2017 |
| CN | 109988234 A | 7/2019 |
| CN | 110003324 A | 7/2019 |
| CN | 110029111 A | 7/2019 |
| CN | 110747198 A | 2/2020 |
| CN | 110964099   | 4/2020 |
| CN | 114106150 A | 3/2022 |
| EP | 0699752 A2  | 3/1996 |

OTHER PUBLICATIONS

Fertala A. Bioengineering (Basel). Dec. 2, 2020;7(4):155 (Year: 2020).*
Golser AV et al. ACS Biomater Sci Eng. Jun. 11, 2018;4(6):2106-2114 (Year: 2018).*
Juming Yao, et al., Design, Expression and Characterization of Collagen-Like Proteins Based on the Cell Adhesive and Crosslinking Sequences Derived from Native Collagens, Japanese Biochemical, 2004, pp. 643-649, vol. 136 No. 5.
Barbara Brodsky Doyle, et al., Infrared Spectroscopy of Collagen and Collagen-Like Polypeptides, Biopolymers, 1975, pp. 937-957, vol. 14.
Hee-Seok Jeong, et al., Isolation and Characterization of Collagen from Marine Fish (*Thunnus obesus*), Biotechnology and Bioprocess Engineering, 2013, pp. 1185-1191, vol. 18.
Zhou Ai-Mei, et al., Purification and characterization of recombinant human-source collagen, Food and Fermentation Industries, 2015, pp. 46-52, vol. 41 No.3.
Chen Jingtao, et al., FT-IR Spectrometric Study of Reconbinant Collagen and Borine Tendon Type I Colleagen, Material Herald, 2008, pp. 119-121, vol. 22 No.3.
PO2452 CO 1A1 Human, retrieved from: https://wwwuniprot.org/uniprot/P02452.
PO2458 CO 2A1 Human, retrieved from: https://www.uniprot.org/uniprot/P02458.

* cited by examiner

*Primary Examiner* — Ram R Shukla
*Assistant Examiner* — Douglas Charles Ryan
(74) *Attorney, Agent, or Firm* — Bayramoglu Law Offices LLC

(57) ABSTRACT

A recombinant collagen and a preparation method and use thereof, and in particular, a full-length collagen α1 chain produced through recombinant expression, and a preparation method and use thereof are provided. When a variant (which is denoted as α1 (I) M1) of a human type I collagen α1 chain (α1 (I) chain) and a variant (which is denoted as α1 (II) M6) of a human type II collagen α1 chain (α1 (II) chain) constructed in the present disclosure are produced through recombinant expression in *Pichia pastoris*, a main degradation product (a main degradation band) in substantially the same proportion as a target product (a target band) of a full-length α1 chain occurring during the recombinant expression of native full-length α1 (I) chain and α1 (II) chain is eliminated, and a yield of the target product is improved.

12 Claims, 32 Drawing Sheets
Specification includes a Sequence Listing.

```
              1                                                    50
    α1(Ⅰ)    QLSYGYDEKS TGGISVPGPM GPSGPRGLPG PPGAPGPQGF QGPPGEPGEP
    α1(Ⅰ)M1  QLSYGYDEKS TGGISVPGPM GPSGPRGLPG PPGAPGPQGF QGPPGEPGEP
              51                                                   100
    α1(Ⅰ)    GASGPMGPRG PPGPPGKNGD DGEAGKPGRP GERGPPGPQG ARGLPGTAGL
    α1(Ⅰ)M1  GASGPPGPPG PPGPPGKNGD DGEAGKPGRP GERGPPGPQG ARGLPGTAGL
              101                                                  150
    α1(Ⅰ)    PGMKGHRGFS GLDGAKGDAG PAGPKGEPGS PGENGAPGQM GPRGLPGERG
    α1(Ⅰ)M1  PGMKGHRGFS GLDGAKGDAG PAGPKGEPGS PGENGAPGQP GPPGLPGERG
              151                                                  1057
    α1(Ⅰ)    RPGAPGPAGA ······ ······ ······ ······ ······ ······  GGRYYRA
    α1(Ⅰ)M1  RPGAPGPAGA ······ ······ ······ ······ ······ ······  GGRYYRA
```

FIG. 1

```
              1                                                    50
    α1(Ⅱ)    QMAGGFDEKA GGAQLGVMQG PMGPMGPRGP PGPAGAPGPQ GFQGNPGEPG
    α1(Ⅱ)M6  QMAGGFDEKA GGAQLGPPQG PPGPPGPPGP PGPAGAPGPQ GFQGNPGEPG
              51                                                   100
    α1(Ⅱ)    EPGVSGPMGP RGPPGPPGKP GDDGEAGKPG KAGERGPPGP QGARGFPGTP
    α1(Ⅱ)M6  EPGVSGPPGP PGPPGPPGKP GDDGEAGKPG KAGERGPPGP QGARGFPGTP
              101                                                  150
    α1(Ⅱ)    GLPGVKGHRG YPGLDGAKGE AGAPGVKGES GSPGENGSPG PMGPRGLPGE
    α1(Ⅱ)M6  GLPGVKGHRG YPGLDGAKGE AGAPGVKGES GSPGENGSPG PPGPPGLPGE
              151                                                  1060
    α1(Ⅱ)    RGRTGPAGAA ······ ······ ······ ······ ······ ······GPDPLQYMRA
    α1(Ⅱ)M6  RGRTGPAGAA ······ ······ ······ ······ ······ ······GPDPLQYMRA
```

FIG. 2

Target band of α1 (I)

FIG. 7A

Main degradation band of α1 (I)

FIG. 7B

Target band of α1 (II)

FIG. 7C

Main degradation band of α1 (II)

FIG. 7D

Target band of α1 (I) M1

FIG. 8A

Target band of α1 (II) M6

SEQUENCE LISTING

```
Sequence total quantity: 12
SEQ ID NO: 1           moltype = AA  length = 1057
FEATURE                Location/Qualifiers
source                 1..1057
                       mol_type = protein
                       organism = Homo sapiens
SEQUENCE: 1
QLSYGYDEKS TGGISVPGPM GPSGPRGLPG PPGAPGPQGF QGPPGEPGEP GASGPMGPRG   60
PPGPPGKNGD DGEAGKPGRP GERGPPGPQG ARGLPGTAGL PGMKGHRGFS GLDGAKGDAG  120
PAGPKGEPGS PGENGAPGQM GPRGLPGERG RPGAPGPAGA RGNDGATGAA GPPGPTGPAG  180
PPGFPGAVGA KGEAGPQGPR GSEGPQGVRG EPGPPGPAGA AGPAGNPGAD GQPGAKGANG  240
APGIAGAPGF PGARGPSGPQ GPGGPPGPKG NSGEPGAPGS KGDTGAKGEP GPVGVQGPPG  300
PAGEEGKRGA RGEPGPTGLP GPPGERGGPG SRGFPGADGV AGPKGPAGER GSPGPAGPKG  360
SPGEAGRPGE AGLPGAKGLT GSPGSPGPDG KTGPPGPAGQ DGRPGPPGPP GARGQAGVMG  420
FPGPKGAAGE PGKAGERGVP GPPGAVGPAG KDGEAGAQGP PGPAGPAGER GEQGPAGSPG  480
FQGLPGPAGP PGEAGKPGEQ GVPGDLGAPG PSGARGERGF PGERGVQGPP GPAGPRGANG  540
APGNDGAKGD AGAPGAPGSQ GAPGLQGMPG ERGAAGLPGP KGDRGDAGPK GADGSPGKDG  600
VRGLTGPIGP PGPAGAPGDK GESGPSGPAG PTGARGAPGD RGEPGPPGPA GFAGPPGADG  660
QPGAKGEPGD AGAKGDAGPP GPAGPAGPPG PIGNVGAPGA KGARGSAGPP GATGFPGAAG  720
RVGPPGPSGN AGPPGPPGPA GKEGGKGPRG ETGPAGRPGE VGPPGPPGPA GEKGSPGADG  780
PAGAPGTPGP QGIAGQRGVV GLPGQRGERG FPGLPGPSGE PGKQGPSGAS GERGPPGPMG  840
PPGLAGPPGE SGREGAPGAE GSPGRDGSPG AKGDRGETGP AGPPGAPGAP GAPGPVGPAG  900
KSGDRGETGP AGPAGPVGPV GARGPAGPQG PRGDKGETGE QGDRGIKGHR GFSGLQGPPG  960
PPGSPGEQGP SGASGPAGPR GPPGSAGAPG KDGLNGLPGP IGPPGPRGRT GDAGPVGPPG 1020
PPGPPGPPGP PSAGFDFSFL PQPPQEKAHD GGRYYRA                         1057
```

```
SEQ ID NO: 2            moltype = AA  length = 1057
FEATURE                 Location/Qualifiers
source                  1..1057
                        mol_type = protein
                        note = Amino acid sequence of a1 (I) M1
                        organism = synthetic construct
SEQUENCE: 2
QLSYGYDEKS TGGISVPGPM GPSGPRGLPG PPGAPGPQGF QGPPGEPGEP GASGPPGPPG    60
PPGPPGKNGD DGEAGKPGRP GERGPPGPQG ARGLPGTAGL PGMKGHRGFS GLDGAKGDAG   120
PAGPKGEPGS PGENGAPGQP GPPGLPGERG RPGAPGPAGA RGNDGATGAA GPPGPTGPAG   180
PPGFPGAVGA KGEAGPQGPR GSEGPQGVRG EPGPPGPAGA AGPAGNPGAD GQPGAKGANG   240
APGIAGAPGF PGARGPSGPQ GPGGPPGPKG NSGEPGAPGS KGDTGAKGEP GPVGVQGPPG   300
PAGEEGKRGA RGEPGPTGLP GPPGERGGPG SRGFPGADGV AGPKGPAGER GSPGPAGPKG   360
SPGEAGRPGE AGLPGAKGLT GSPGSPGPDG KTGPPGPAGQ DGRPGPPGPP GARGQAGVMG   420
FPGPKGAAGE PGKAGERGVP GPPGAVGPAG KDGEAGAQGP PGPAGPAGER GEQGPAGSPG   480
FQGLPGPAGP PGEAGKPGEQ GVPGDLGAPG PSGARGERGF PGERGVQGPP GPAGPRGANG   540
APGNDGAKGD AGAPGAPGSQ GAPGLQGMPG ERGAAGLPGP KGDRGDAGPK GADGSPGKDG   600
VRGLTGPIGP PGPAGAPGDK GESGPSGPAG PTGARGAPGD RGEPGPPGPA GFAGPPGADG   660
QPGAKGEPGD AGAKGDAGPP GPAGPAGPPG PIGNVGAPGA KGARGSAGPP GATGFPGAAG   720
RVGPPGPSGN AGPPGPPGPA GKEGGKGPRG ETGPAGRPGE VGPPGPPGPA GEKGSPGADG   780
PAGAPGTPGP QGIAGQRGVV GLPGQRGERG FPGLPGPSGE PGKQGPSGAS GERGPPGPMG   840
PPGLAGPPGE SGREGAPGAE GSPGRDGSPG AKGDRGETGP AGPPGAPGAP GAPGPVGPAG   900
KSGDRGETGP AGPAGPVGPV GARGPAGPQG PRGDKGETGE QGDRGIKGHR GFSGLQGPPG   960
PPGSPGEQGP SGASGPAGPR GPPGSAGAPG KDGLNGLPGP IGPPGPRGRT GDAGPVGPPG  1020
PPGPPGPPGP PSAGFDFSFL PQPPQEKAHD GGRYYRA                          1057

SEQ ID NO: 3            moltype = DNA  length = 3171
FEATURE                 Location/Qualifiers
source                  1..3171
                        mol_type = other DNA
                        note = Nucleotide sequence encoding a1 (I) M1
                        organism = synthetic construct
SEQUENCE: 3
caacttagtt atggatacga tgaaaaatcc acaggtggaa tcagtgttcc tggacctatg    60
ggtccatcag gtccaagagg tttaccagga cctccaggtg ccccaggtcc cagggattt   120
caaggtccac caggagagcc tggtgagcca ggagcttctg gtccacctgg tccccctgga   180
ccacctggtc ctccagagaaa gaatggagat gatggtgaag ctggaaaacc tggaagacct   240
ggagaaagag gaccaccagg accccagggt gccagagcac tgccaggtac cgcaggtctg   300
cctggaatga aggtcatag aggattttca ggattagacg gtgccaaagg agacgctgga   360
cctgcaggac caaagggtga gccaggaagt ccaggagaga tggtgcacc aggacagcca   420
ggtccacctg gactgcccgg tgaaagaggt agacccggag caccaggacc agcaggtgca   480
agaggaaatg atggagctac aggtgctgca ggaccccag gtcaacagg accagccggt   540
cctcccggtt tcccaggtgc cgttggagca aaaggtgaag ctggtccaca gggtccaaga   600
ggttctgaag gtcacagggg agttagagga gaaccaggac ccctggacc agctggtgca   660
gcaggaccag ctggtaaccc tggtgctgac ggtcagccag gtgctaaggg agcaaatgga   720
gcaccaggaa tagctggtgc cccaggattt ccggtgctga gaggtccaag tggtccacaa   780
ggaccaggag gtccaccccgg tcccaaagga aacagtggag aaccaggtgc acccggttca   840
aagggagata caggagctaa aggagagccc ggtccagtgg tgttcaggg accaccggga   900
cctgctggag aggaaggtaa aagaggtgca agaggtgagc caggaccaac aggtctgcct   960
ggtccccctg gtgaaagagg tggtccaggt agtagagat ttccaggagc tgatggtgta  1020
gcaggaccaa agggacccgc aggtgagaga gatcacccg gtccagccgg accaaaagga  1080
tcaccaggag aagctggtag accaggaga gctggtctgc caggtgctaa aggattgaca  1140
ggatcacccg gttcacctgg tcctgatgga agacaggagc tccaggtcc cgctggtcag  1200
gacggtagac caggacccc aggacccca ggtcaagag gtcaggcagg tgtaatgggt  1260
ttccccggac ctaaaggagc agctggagaa cctggtaaag ctggagagag aggagtgcct  1320
ggaccccctg gagctgttgg tccagcagga aaggatggtg aggcaggtgc acaaggtcca  1380
cctggacccg ctggacctgc aggtgagaga ggagagcaag gtcccgcagg ttctccaggt  1440
tttcagggtt tgccaggtcc agccggtcct cctggagagg caggaaagcc aggagaacaa  1500
ggagttccag gagacctggg tgcaccagga ccctctggtg caagaggaga gaggagattt  1560
cctggagaaa gaggtgtgca gggaccacca ggtcccgccg gtccaagagg agcaaatgga  1620
gcccctggaa atgacggagc taagggtgac gctggtgcac aggagcacc aggttctcaa  1680
ggtgctcccg gattgcaggg tatgcctgga gagagaggtg cagctggact gccaggtcca  1740
aaaggtgaca gaggagacgc cggtcctaag ggagctgacg gttctcctgg aaaggacggt  1800
gtgagaggtt tgacaggacc aataggtcca cccggtcctg ctggagcccc tggagacaaa  1860
ggtgaatcag gtccttccgg tccagccgga ccaacaggag caagaggagc acctggagac  1920
agaggagagc caggtcctcc aggacctgca ggtttcgctg gtcctcccgg agcagatgga  1980
cagccaggag ctaagggaga acccggtgac gctggtgcta agggagatgc aggtccacca  2040
ggtcctgctg gtcctgctgg acctcccgga ccaataggta atgttggagc accggagca  2100
aaaggtgcca gaggttccgc aggtcctccc ggagcaactg gttttccagg agctgccgga  2160
agagtgggtc cacctggtcc ttctggaaat gcaggaccac caggtcctcc tggtccagcc  2220
ggaaaggaag gtgaaagggg acctagagga gaaacaggtc ccgcaggtag acccggtgag  2280
gtgggtccac ctggtccacc cggtccagct ggtgagaaag gaagtcctgg agcagacgga  2340
ccagctggtg ccctgggac caccaggacc caaggatact ccaggaccc caggtcaaag  2400
ggtttaccag gtcagagagg agaaagaggt tttccaggat taccaggtcc ctcaggtgag  2460
cccggaaaac agggtccctc aggagcaagt ggtgaaagag gaccaccagg accaatggga  2520
cctccaggat tagctggtcc accaggagaa tcaggaagag agggtgctcc tggagcaaa  2580
ggttcaccag gaagagacgg ttcacccgga gccaagggag acagaggtga acaggtcccc  2640
gcaggtccac caggagcacc cggagcccct ggtgctccag gacctgtcgg accagcagga  2700
```

-continued

```
aaatccggtg acagaggtga gactggaccc gcaggtcctg ctggtcctgt tggaccagtg   2760
ggtgcaagag gaccagcagg tccacaaggt ccaagaggtg acaaaggtga gacaggtgag   2820
cagggtgaca gaggaattaa aggtcacaga ggattttcag gactgcaggg accacccggt   2880
cctcccggtt ccccaggaga gcaaggtcca tccggtgcat ccggtccagc tgggcccaga   2940
ggaccacctg gttctgctgg tgcaccaggt aaagatggat tgaacgtttt gcctggtcca   3000
ataggacctc ctggtccaag aggaagaact ggtgacgccg gtcccgtcgg accacccggt   3060
ccaccaggtc ccccaggtcc acccggacca ccatccgcag gatttgattt ctcattcctt   3120
cctcaacctc tcaagagaaa agcacatgat ggaggtagat actatagagc c            3171
```

| SEQ ID NO: 4 | moltype = AA   length = 1060 |
|---|---|
| FEATURE | Location/Qualifiers |
| source | 1..1060 |
| | mol_type = protein |
| | organism = Homo sapiens |

```
SEQUENCE: 4
QMAGGFDEKA GGAQLGVMQG PMGPMGPRGP PGPAGAPGPQ GFQGNPGEPG EPGVSGPMGP    60
RGPPGPPGKP GDDGEAGKPG KAGERGPPGP QGARGFPGTP GLPGVKGHRG YPGLDGAKGE   120
AGAPGVKGES GSPGENGSPG PMGPRGLPGE RGRTGPAGAA GARGNDGQPG PAGPPGPVGP   180
AGGPGFPGAP GAKGEAGPTG ARGPEGAQGP RGEPGTPGSP GPAGASGNPG TDGIPGAKGS   240
AGAPGIAGAP GFPGPRGPPG PQGATGPLGP KGQTGEPGIA GFKGEQGPKG EPGPAGPQGA   300
PGPAGEEGKR GARGEPGGVG PIGPPGERGA PGNRGFPGQD GLAGPKGAPG ERGPSGLAGP   360
KGANGDPGRP GEPGLPGARG LTGRPGDAGP QGKVGPSGAP GEDGRPGPPG PQGARGQPGV   420
MGFPGPKGAN GEPGKAGEKG LPGAPGLRGL PGKDGETGAA GPPGPAGPAG ERGEQGAPGP   480
SGFQGLPGPP GPPGEGGKPG DQGVPGEAGA PGLVGPRGER GFPGERGSPG AQGLQGPRGL   540
PGTPGTDGPK GASGPAGPPG AQGPPGLQGM PGERGAAGIA GPKGDRGDVG EKGPEGAPGK   600
DGGRGLTGPI GPPGPAGANG EKGEVGPPGP AGSAGARGAP GERGETGPPG PAGFAGPPGA   660
DGQPGAKGEQ GEAGQKGDAG APGPQGPSGA PGPQGPTGVT GPKGARGAQG PPGATGFPGA   720
AGRVGPPGSN GNPGPPGPPG PSGKDGPKGA RGDSGPPGRA GEPGLQGPAG PPGEKGEPGD   780
DGPSGAEGPP GPQGLAGQRG IVGLPGQRGE RGFPGLPGPS GEPGKQGAPG ASGDRGPPGP   840
VGPPGLTGPA GEPGREGSPG ADGPPGRDGA AGVKGDRGET GAVGAPGAPG PPGSPGPAGP   900
TGKQGDRGEA GAQGPMGPSG PAGARGIQGP QGPRGDKGEA GEPGERGLKG HRGFTGLQGL   960
PGPPGPSGDQ GASGPAGPSG PRGPPGPVGP SGKDGANGIP GPIGPPGPRG RSGETGPAGP  1020
PGNPGPPGPP GPPGPGIDMS AFAGLGPREK GPDPLQYMRA                        1060
```

| SEQ ID NO: 5 | moltype = AA   length = 1060 |
|---|---|
| FEATURE | Location/Qualifiers |
| source | 1..1060 |
| | mol_type = protein |
| | note = Amino acid sequence of α1 (II) M6 |
| | organism = synthetic construct |

```
SEQUENCE: 5
QMAGGFDEKA GGAQLGPPQG PPGPPGPPGP PGPAGAPGPQ GFQGNPGEPG EPGVSGPPGP    60
PGPPGPPGKP GDDGEAGKPG KAGERGPPGP QGARGFPGTP GLPGVKGHRG YPGLDGAKGE   120
AGAPGVKGES GSPGENGSPG PPGPPGLPGE RGRTGPAGAA GARGNDGQPG PAGPPGPVGP   180
AGGPGFPGAP GAKGEAGPTG ARGPEGAQGP RGEPGTPGSP GPAGASGNPG TDGIPGAKGS   240
AGAPGIAGAP GFPGPRGPPG PQGATGPLGP KGQTGEPGIA GFKGEQGPKG EPGPAGPQGA   300
PGPAGEEGKR GARGEPGGVG PIGPPGERGA PGNRGFPGQD GLAGPKGAPG ERGPSGLAGP   360
KGANGDPGRP GEPGLPGARG LTGRPGDAGP QGKVGPSGAP GEDGRPGPPG PQGARGQPGV   420
MGFPGPKGAN GEPGKAGEKG LPGAPGLRGL PGKDGETGAA GPPGPAGPAG ERGEQGAPGP   480
SGFQGLPGPP GPPGEGGKPG DQGVPGEAGA PGLVGPRGER GFPGERGSPG AQGLQGPRGL   540
PGTPGTDGPK GASGPAGPPG AQGPPGLQGM PGERGAAGIA GPKGDRGDVG EKGPEGAPGK   600
DGGRGLTGPI GPPGPAGANG EKGEVGPPGP AGSAGARGAP GERGETGPPG PAGFAGPPGA   660
DGQPGAKGEQ GEAGQKGDAG APGPQGPSGA PGPQGPTGVT GPKGARGAQG PPGATGFPGA   720
AGRVGPPGSN GNPGPPGPPG PSGKDGPKGA RGDSGPPGRA GEPGLQGPAG PPGEKGEPGD   780
DGPSGAEGPP GPQGLAGQRG IVGLPGQRGE RGFPGLPGPS GEPGKQGAPG ASGDRGPPGP   840
VGPPGLTGPA GEPGREGSPG ADGPPGRDGA AGVKGDRGET GAVGAPGAPG PPGSPGPAGP   900
TGKQGDRGEA GAQGPMGPSG PAGARGIQGP QGPRGDKGEA GEPGERGLKG HRGFTGLQGL   960
PGPPGPSGDQ GASGPAGPSG PRGPPGPVGP SGKDGANGIP GPIGPPGPRG RSGETGPAGP  1020
PGNPGPPGPP GPPGPGIDMS AFAGLGPREK GPDPLQYMRA                        1060
```

| SEQ ID NO: 6 | moltype = DNA   length = 3180 |
|---|---|
| FEATURE | Location/Qualifiers |
| source | 1..3180 |
| | mol_type = other DNA |
| | note = Nucleotide sequence encoding α1 (II) M6 |
| | organism = synthetic construct |

```
SEQUENCE: 6
caaatggctg gtggattcga tgaaaaggct ggtggagccc aattaggtcc tccacaaggt    60
cctcccggtc cacctggtcc tcccggtcct ccaggtcccg ccggtgctcc tggaccacag   120
ggttccaag gaaaccccgg tgaaccaggt gagcctggtg tttcaggtcc tcccggtcct   180
ccaggaccac ctgaccacc aggaaagcct ggtgacgacg gagaagctgg taaaccagga   240
aaggcaggag agagaggtcc acctggacct cagggtgcca gaggtttccc aggtaccccc   300
ggtcttcctg gtgtcaaggg tcatagaggt taccccggtt tggatggtgc caaggtgaa   360
gccggtgccc ctggtgttaa gggtgaatca ggaagtccag gtgaaaatgg aagtcccggt   420
ccacccggtc cacctggact gccaggtgag agaggaagaa ccggaccagc tggtgctgca   480
ggtgctagag gaaatgacgg acagcccgga ccagccggac ctcccggtcc tgttgggccc   540
gcaggtggtc ctggtttccc tggtgctcct ggagccaaag gagaagccgg acccaccgga   600
gccagaggtc ccgagggagc acaggacct agaggagaac caggtacacc aggtagtccc   660
ggtcctgctg gtgcatcagg aaatcccgga actgacggta ttccaggagc aaagggatct   720
```

```
gcaggagcac caggaatagc tggtgctcct ggatttccag gtcccagagg acctcccggt   780
cctcaaggag caacaggtcc tttgggacca aaaggtcaaa caggagaacc aggtattgct   840
ggattcaaag gagagcaagg tccaaaggga gagcccggtc ccgcaggtcc ccaaggagcc   900
ccaggaccag ctggtgaaga aggaaaaaga ggagccagag gtgaacctgg aggagtagga   960
cctattggtc ctcctggtga gagaggtgct cccggaaaca gaggttttcc tggtcaagat  1020
ggtctggctg gacctaaagg tgctccagga gagagaggcc ttcaggact tgctggtcca  1080
aaaggtgcta acggagatcc aggaagaccc ggtgaacctg gtctgcctgg agctagagga  1140
ttaacaggaa gaccaggtga cgcaggtccc cagggtaaag tgggtcccag tggtgcccca  1200
ggtgaagatg gaagacctgg tcctcccgga ccccaaggtg caagaggtca gcctggagtg  1260
atgggatttc ctggacccaa gggtgctaac ggagaacctg gaaaagctgg tgagaaagga  1320
ctgcccggtg ccccaggtct tagaggtttg ccaggtaaag atggagaaac aggagccgca  1380
ggaccacccg gtccagccgg accagcagga gagagaggtg aacaaggagc cctggtccaa  1440
agtggttttc agggtcttcc aggtcccct ggtccaccag agagggagg taaaccaggt  1500
gaccaaggtg tccctggaga agcagtgca cccggtcttg tgggtccaaa aggtgaaaga  1560
ggattccctg gtgagagagg atctcccgga gcccagggac ttcaaggtcc tagaggtctg  1620
ccaggtaccc ctggtacaga cggaccaaag ggagcatcag gacccgctgg acctcccgga  1680
gcccaaggtc ctccaggttt acaaggtatg cctggtgaaa gaggtgctgc aggtatagct  1740
ggaccaaaag gagacagagg tgacgttggt gagaaggtc ccgaaggagc ccctggaaaa  1800
gatggtggaa gaggattaac aggtcctata ggaccacccg gtccagccgg tgctaatgga  1860
gaaaaaggaa agtaggtcc tccaggtcca gcaggatctg caggtgctag aggtgcccct  1920
ggagagagag gtgaaacagg accacctggt ccagctggtt tcgctggtcc cccaggagct  1980
gatggacagc ccggtgcaaa aggtgaacaa ggagaagccg gacagaaggg agatgctgga  2040
gcccccggtc cacaaggtcc ctcaggagca ccaggtcctc aaggtccaac tggtgtgacc  2100
gggcaaaagg gtgcaagagg agcacaggga cctccaggag caacaggttt cccaggagct  2160
gctggtagag tcggtccacc cggatctaat ggtaaccccg gccaccagg accacctgga  2220
ccatctggaa aggatgacc caaaggagca agaggaatt caggaccacc cggaagacca  2280
ggagaacctg gattacaggg tcccgccggt ccaccaggag agaaaggaga gcccggagat  2340
gatggtccct caggtgcaga gggaccccca ggaccccaag gtctggcagg tcaaagaggt  2400
atagtgggtc ttccaggtca agaggtgaaa agaggatttc aggacttcc aggtccttca  2460
ggtgaacccg gtaaacaggg agcccccgga gcctcaggtg acagaggtcc tccaggacca  2520
gtaggacccc caggtttaac cggaccagca ggtgagccga aagagaaggg ttctcctgga  2580
gccgatggac ctcaggaag agacggtgca gctggtgtta agggtgacag aggtgaaact  2640
ggagccgtag gagccccagg tgccccgga ccacccggat cacccggacc tgcaggtcct  2700
actggtaaac aaggagatag aggagaagcc ggtgcccagg gtcctatggg tcctttctggt  2760
cctgcaggag caaggtat acaaggtcca caggtccca gaggtgacaa gggtgaagca  2820
ggagaaccg gtgagagagg tctgaaggt catagaggat tcaccgggtt acagggttg  2880
ccaggacccc ctggaccaag tggtgaccag ggtgcatccg tccagcagg tccttctgga  2940
ccaagaggtc ctcccggtcc agttggtcca tcaggtaaaa acggagccaa cggtatccca  3000
ggtcccatcg gtcctccagg tcctagagga agaagtggag agactggtcc tgctggacct  3060
cctggaaacc ctggtcctcc aggacctcca ggtcctggag gtcccggaat agatatgtcc  3120
gctttcgctg gattgggacc aagagagaaa ggtcctgacc ctcttcaata tatgagagca  3180
```

```
SEQ ID NO: 7              moltype = AA  length = 1071
FEATURE                   Location/Qualifiers
source                    1..1071
                          mol_type = protein
                          note = Amino acid sequence of a1 (I) M1 with N-terminal
                            Strep-Tag II tag and C-terminal 6 x His Tag
                          organism = synthetic construct
SEQUENCE: 7
WSHPQFEKQL SYGYDEKSTG GISVPGPMGP SGPRGLPGPP GAPGPQGFQG PPGEPGEPGA    60
SGPPGPPGPP GPPGKNGDDG EAGKPGRPGE RGPPGPQGAR GLPGTAGLPG MKGHRGFSGL   120
DGAKGDAGPA GPKGEPGSPG ENGAPGQPGP PGLPGERGRP GAPGPAGARG NDGATGAAGP   180
PGPTGPAGPP GFPGAVGAKG EAGPQGPRGS EGPQGVRGEP GPPGPAGAAG PAGNPGADGQ   240
PGAKGANGAP GIAGAPGFPG ARGPSGPQGP GGPPGPKGNS GEPGAPGSKG DTGAKGEPGP   300
VGVQGPPGPA GEEGKRGARG EPGPTGLPGP PGERGGPGSR GFPGADGVAG PKGPAGERGS   360
PGPAGPKGSP GEAGRPGEAG LPGAKGLTGS PGSPGPDGKT GPPGPAGODG RPGPPGPPGA   420
RGQAGVMGFP GPKGAAGEPG KAGERGVPGP PGAVGPAGKD GEAGAQGPPG PAGPAGERGE   480
QGPAGSPGFQ GLPGAPGPPG EAGKPGAGQGV PGDLGAPGPS PGERGRPFG ERGVQGPPGP   540
AGPRGANGAP GNDGAKGDAG APGAPGSQGA PGLQGMPGER GAAGLPGPKG DRGDAGPKGA   600
DGSPGKDGVR GLTGPIGPPG PAGAPGDKGE SGPSGPAGPT GARGAPGDRG EPGPPGPAGF   660
AGPPGADGQP GAKGEPGDAG AKGDAGPPGP AGPAGPPGPI GNVGAPGAKG ARGSAGPPGA   720
TGFPGAAGRV GPPGPSGNAG PPGPPGPAGK EGGKGPREGV GEPGPPGPAE              780
KGSPGADGPA GAPGTPGPQG IAGQRGVVGL PGQRGERGFP GLPGSEGPG KQGPSGASGE   840
RGPPGPMGPP GLAGPPGESG REGAPGAEGS PGRDGSPGAK GDRGETGPAG PPGAPGAPGA   900
PGPVGPAGKS GDRGETGPAG PAGPVGPVGA RGPAGPQGPR GDKGETGEQG DRGIKGHRGF   960
SGLQGPPGPP GSPGEQGPSG ASGPAGPRGP PGSAGPAGKD GLNGLPGPIG PPGPRGRTGD  1020
AGPVGPPGPP GPPGPPGPPS AGFDFSFLPQ PPQEKAHDGG RYYRAHHHHH H           1071
```

```
SEQ ID NO: 8              moltype = DNA  length = 3216
FEATURE                   Location/Qualifiers
source                    1..3216
                          mol_type = other DNA
                          note = DNA sequence of gene COL1A1M1 encoding a1 (I) M1
                            with N-terminal Strep-Tag II tag and C-terminal 6 x His Tag
                          organism = synthetic construct
SEQUENCE: 8
tggtctcatc cacaatttga aaagcaactt agttatggat acgatgaaaa atccacaggt    60
ggaatcagtg ttcctggacc tatgggtcca tcaggtccaa gaggtttacc aggacctcca   120
```

```
ggtgcccag gtccccaggg atttcaaggt ccaccaggag agcctggtga gccaggagct     180
tctggtccac ctggtccccc tggaccacct ggtcctccag gaaagaatgg agatgatggt     240
gaagctggaa aacctggaag acctggagaa agaggaccac caggacccca gggtgccaga     300
ggactgccag gtaccgcagg tctgcctgga atgaaaggtc atagaggatt ttcaggatta     360
gacggtgcaa agggagacgc tggacctgca ggaccaaagg gtgagccagg aagtccagga     420
gagaatggtg caccaggaca gccaggtcca cctggactgc ccgtgaaag aggtagaccc      480
ggagcaccag gaccagcagg tgcaagagga atgatggag ctacaggtgc tgcaggaccc      540
ccaggtccaa caggaccagc cggtcctccc ggtttcccag gtgccgttgg agcaaaaggt     600
gaagctggtc cacagggtcc aagaggttct gaaggtccac agggagttag aggagaaca     660
ggaccccctg gaccagctga tgcagcagga ccagctggtc accctggtgc tgacggtcag     720
ccaggtgcta agggagcaaa tggagcacca ggaatagctg gtccccagg atttcccggt      780
gctagaggtc caagtggtcc acaaggacca ggaggtccac ccgtccaa aggaaacagt       840
ggagaaccag gtgcacccgg ttcaaggga gatacaggag ctaaggaga gcccggtcca       900
gtgggtgttc agggaccacc cggacctgct ggagaggaag gtaaaagggg tgcaagaggt    960
gagccaggac aacaggtct gcctggtccc cctggtgaaa gaggtggtcc aggtagtaga    1020
ggatttccag gagctgatgg tgttgcagga ccaaagggac cgcaggtga gagaggatca    1080
cccggtccag ccggaccaaa aggatcacca ggagaagctg gtagaccagg agaagctggt    1140
ctgccaggtg ctaaaggatt gacaggatca cccggttcac ctggtcctga tggaaagaca    1200
ggacctccag gtcccgctgg tcaggacggt agaccaggac ccccaggacc ccaggtgca     1260
agaggtcagg caggtgtaat gggttttccc ggacctaaag gagcagctgg agaacctggt    1320
aaagctggag agaggagt gcctggaccc cctggagctg ttggtccagc aggaaggat      1380
ggtgaggcag gtgcacaagg tccacctgga ccgctggaa ctgcaggtga gaggagag      1440
caaggtcccg caggttctcc aggttttcag ggtttgccag gtccagccgg tcctcctgga    1500
gaggcaggaa agccaggaga acaaggagtt ccaggagacc tgggtgcacc aggaccctct    1560
ggtgcaagag agagagagg atttcctgga aaaagggt gcagggacc accaggtccc       1620
gccggtccaa gaggagcaaa tggagccccc tgaaatgacg gagctaaggg tgacgctggt    1680
gcaccaggag cacccaggtt tcaaggtgct cccggattgc agggtatgcc tggagaga     1740
ggtgcagctg gactgccagg tccaaaaggt gacagaggag acgccggtcc taagggagct    1800
gacggttctc ctgaaagga cggtgtgaga ggtttgacag gaccaatagg tccaccccgt    1860
cctgctggag cccctggaga caaagggaa tcaggtcctt ccggtccagc cggaccaaca    1920
ggagcaagag gagcacctgg agacagagga gagccaggtc ctccaggac tgcaggttcc    1980
gctggtcctc ccggagcaga tggacagcca ggagctaagg gagaacccgg tgacgctggt    2040
gctaagggag atgcaggtcc accagggtct gctggtctg ctggacctcc cggaccaata    2100
ggtaatgttg gagcaccccgg agcaaaaggt gccagaggtt ccgcaggtcc tcccgagca    2160
actggttttc caggagctgc cggaagagtg ggtccacctg gtccttctgg aaatgcaaa    2220
ccaccaggtc ctcctggtcc agccggaaag gaaggtggaa agggacctag aggagaaaca   2280
ggtcccgcag gtagacccgg tgaggtgggt ccacctggtc cacccggtcc agctggtgag    2340
aaaggaagtc ctggagcaga cggaccagct ggtgccctg taacaccagg accccaagga    2400
atagctggtc aaagaggtgt tgttggttta ccaggtcaga gaggagaaa aggttttcca    2460
ggattaccag gtccctcagg tgagcccgga aaacaggtca cctcaggagc aagtggtgaa    2520
agagaccac caggaccaat gggacctcca ggattagctg gtccaccagg agaatcagga    2580
agagagggtg ctcctggagc agaaggttca ccaggaagag acggttcacc cggagccaag    2640
ggagacagag gtgaaacagg tcccgcaggt ccaccaggac accccggtgct ccctggtgct    2700
ccaggacctg tcggaccagc aggaaaatcc ggtgacaga gtgagactgg acccgcaggt    2760
cctgctggtc ctgttggacc agtgggtgca agaggaccag caggtccaca aggtccaaga    2820
ggtgacaaag tgagacaggt gagcagggt gacagagaaa tttaaaggtca cagaggattt    2880
tcaggactgc aggggaccacc cggtcctccc ggttcccag gagagcaagg tccatccggt    2940
gcatccggtc cagctggacc cagaggacca cctggttctg ctgtgcacc aggtaaagat     3000
ggattgaacg gtttgcctgg tccaatagga cctcctggtc caagaggaag aactggtgac    3060
gccgtccccg tcgaccacc cggtccacca ggtccccag gtccaccgg accaccatcc       3120
gcaggattg atttctcatt ccttcctcaa cctcctcaag agaaagcaca tgatggaggt     3180
agatactata gagcccatca ccaccatcat cattaa                              3216

SEQ ID NO: 9          moltype = AA  length = 1076
FEATURE               Location/Qualifiers
source                1..1076
                      mol_type = protein
                      note = Amino acid sequence of a1(II) M6 with N-terminal
                        Strep-Tag II tag and C-terminal 6 x His Tag
                      organism = synthetic construct
SEQUENCE: 9
EFWSHPQFEK QMAGGFDEKA GGAQLGPPQG PPGPPGPPGP PGPAGAPGPQ GFQGNPGEPG      60
EPGVSGPPGP PGPPGPPGKP GDDGEAGKPG KAGERGPPGP QGARGFPGTP GLPGVKGHRG    120
YPGLDGAKGE AGAPGVKGES GSPGENGSPG PPGPPGLPGE RGRTGPAGAA GARGNDGQPG    180
PAGPPGPVGP AGGPGFPGAP GAKGEAGPTG ARGPEGAQGP RGEPGTPGSP GPAGASGNPG    240
TDGIPGAKGS AGAPGIAGAP GFPGPRGPPG PQGATGPLGP KGQTGEPGIA GFKGEQGPKG    300
EPGPAGPQGA PGPAGEEGKR GARGEPGGVG PIGPPGERGA PGNRGFPGQD GLAGPKGAPG    360
ERGPSGLAGP KGANGDPGRP GEPGLPGARG LTGRPGDAGP QGKVGPSGAP GEDGRPGPPG    420
PQGARGQPGV MGFPGPKGAN GEPGKAGEKG LPGAPGLRGL PGKDGETGAA GPPGPAGPAG    480
ERGEQGAPGP SGFQGLPGPP GPPGEGGKPG DQGVPGEAGA PGLVGPRGER GFPGERGSPG    540
AQGLQGPRGL PGTPGTDGPK GASGPAGPPG AQGPPGLQGM PGERGAAGIA GPKGDRGDVG    600
EKGPEGAPGK DGGRGLTGPI GPPGPAGANG EKGEVGPPGP AGSAGARGAP GERGETGPPG    660
PAGFAGPPGA DGQPGAKGEQ GEAGQKGDAG APGPQGPSGA PGPQGPTGVT GPKGARGAQG    720
PPGATGFPGA AGRVGPPGSN GNPGPPGPPG PSGDGPKGA RGDSGPPGRA GEPGLQGPPG    780
PPGEKGEPGD DGPSGAEGPP GPQGLAGQRG IVGLPGQRGE RGFPGLPGPS GEPGKQGAPG    840
ASGDRGPPGP VGPPGLTGPA GEPGREGSPG ADGPPGRDGA AGVKGDRGET GAVGAPGAPG    900
PPGSPGPAGP TGKQGDRGEA GAQGPMGPSG PAGARGIQGP QGPRGDKGEA GEPGERGLKG    960
HRGFTGLQGL PGPPGPSGDQ GASGPAGPSG PRGPPGPVGP SGKDGANGIP GPIGPPGPRG   1020
RSGETGPAGP PGNPGPPGPP GPPGPGIDMS AFAGLGPREK GPDPLQYMRA HHHHHH        1076
```

SEQ ID NO: 10           moltype = DNA  length = 3231
FEATURE                 Location/Qualifiers
source                  1..3231
                        mol_type = other DNA
                        note = DNA sequence of gene COL2A1M6 encoding a1 (II) M6
                        with N-terminal Strep-Tag II tag and C-terminal 6 x His Tag
                        organism = synthetic construct
SEQUENCE: 10
gaattctgga gtcatcctca attcgaaaaa caaatggctg gtggattcga tgaaaaggct   60
ggtggagccc aattaggtcc tccacaaggt cctcccggtc cacctggtcc tcccggtcct  120
ccaggtcccg ccgtgctcc tggaccacag ggtttccaag aaacccggg tgaaccaggt   180
gagcctggtg tttcaggtcc tcccggtcct ccaggaccac tggaccacc aggaaagcct   240
ggtgacgacg gagaagctgg taaaccagga aaggcaggag ggtggttcc acctggactg   300
cagggtgcca gaggtttccc aggtaccct ggtcttcctg tgtcaaggg tcatagaggt   360
taccccggtt tggatggtgc caagggtgaa gccggtgccc ctggtgttaa gggtgaatca   420
ggaagtcccg gtgaaaatgg aagtcccggt ccacccggtc cacctggact gccaggtgag   480
agaggaagaa ccggaccagc tggtgctgca ggtgctgcaa ggaatgacgg acagcccgga   540
ccagccggac ctcccggtcc tgttgggcc gcaggtggtc ctggttccc tggtgctcct   600
ggagccaaag agaagccgg acccaccgga gccagaggtc ccgagggagc cagggacct   660
agaggagaac caggtacacc aggtagtccc ggtcctgctg gtgcatcagg aaatcccgga   720
actgacggta ttccaggagc aaagggatct gcaggacgac caggaatagc tggtgctcct   780
ggatttccag gtcccagagg acctccccgg cctcaaggag caacaggtcc tttgggacca   840
aaaggtcaaa caggagaacc aggtattgct ggattcaaag gagagcaagg tccaaaggga   900
gagcccggtc ccgcaggtcc ccaaggagcc caggaccag ctggtgaaga aggaaaaaga   960
ggagccagag gtgaacctgg aggagtagga cctattggtc ctcctggtga gaggtgct  1020
cccggaaaca gaggttttcc tggtcaagat ggtctggctg gacctaaagg tgctccagga  1080
gagagaggac cttcaggact tgctggtcca aaaggtgcta acggagatcc aggaagaccc  1140
ggtgaacctg tctgcctgg agctagagga ttaacaggaa gaccaggtga cgcaggtccc  1200
cagggtaaag tgggtcccag tggtgcccca ggtgaagatg gaaagacctg tcctcccgga  1260
ccccaaggtg caagaggtca gctggagtg atgggatttc ctggacccaa gggtgctaac  1320
ggagaacctg gaaaagctgg tgagaaagga ctgcccggtg ccccaggtct tagaggttg  1380
ccaggtaaag atggagaaac aggagccgca ggaccacccg gtccagccgg accagcagga  1440
gagagaggtg aacaaggagc acctggtcca agtggttttc agggtcttcc aggtcccct  1500
ggtccaccag gagagggagg taaaccaggt gaccaaggtg tcctggaga agcaggtca  1560
cccggtcttg tgggtccaag aggtgaaaga ggattccctg gtgagagagg atctcccgga  1620
gcccaggac ttcaaggtcc tagaggtctg ccaggtaccc tggtacaga cggaccaaag  1680
ggagcatcag gaccgctgg acctcccgga gcccaaggtc ctcaggttt acaaggtatg  1740
cctgtggaaa gaggtgtgc aggtatagct ggaccaaaag gagacagggt gacgttggt  1800
gagaagggtc ccgaaggagc ccctggaaaa gatggtggaa gaggattaac aggtcctata  1860
ggaccacccg gtccagccgg tgctaatgga gaaaaggag aagtaggcc tccaggtcca  1920
gcaggatctg caggtgctag aggtgccct ggagagagag tgaaacagg accacctggt  1980
ccagctggtt tcgctggtcc cccaggagct gatggacagc ccggtgcaa aggtgaacaa  2040
ggagaagccg gacagaaggg agatgctgga gcccccggtc acaaggtcc ctcaggagca  2100
ccaggtcctc aaggtccaac tggtgtgacc gggccaaagg gtcaagagg agcacaggga  2160
cctccaggag caacaggttt cccaggagct gctggtagag tcggtccacc cggatctaat  2220
ggtaacccg gaccaccagg accacctgga ccatctggca aggatggagca  2280
agaggagatt caggaccacc cggaagagca ggagaacctg gattacaggg tcccgccggt  2340
ccaccaggag agaaggaga gcccggagat gatggtccct caggtgcaga gggacccca  2400
ggaccccaag gtctggcagg tcaaagaggt atagtgggtc ttccaggtca agagggtaa  2460
agaggatttc caggacttcc aggtcctcc ggtgaacccg gtaaacaggg gcctcaggtg  2520
gcctcaggtg acagaggtcc tccaggacca gtaggacccc aggtttaac cggaccagca  2580
ggtgagccag aagagaagg ttctcctgga gccgatggac ctcaggaag acggtgca  2640
gctggtgtta gggtgacag aggtgaaact ggagccgtag gagccccagg tgcccccgga  2700
ccaccggat cacccggacc tgcaggtcct actggtaaa aaggagatag aggagaagcc  2760
ggtgccagg gtcctatggg tccttctggt cctgcaggaa caagaggtat acaaggtca  2820
cagggtccca gaggtgacaa gggtgaagca ggagaaccg gtgagagagg tctgaagggt  2880
catagaggat tcaccgggtt acaggttttg ccaggacccc ctggaccaag tggtgaccag  2940
ggtgcatccg gtccagcagg tcctcctgga ccaagggtcc ctcccggtcc agttggtcca  3000
tcaggtaaag acggagccaa cggtatccca gtcctcccatg gtccctagagga  3060
agaagtggag agactggcc tgctggacct cctggaaacc ctggtctcc aggaccca  3120
ggtcctccag gtccccgaat agatatgtcc gcttcgctgg gattgggacc aagaagaaa  3180
ggtcctgacc tcttcaaata tatgagagca caccatcacc atcatcacta a           3231

SEQ ID NO: 11           moltype = AA length = 1464
FEATURE                 Location/Qualifiers
source                  1..1464
                        mol_type = protein
                        organism = Homo sapiens
SEQUENCE: 11
MFSFVDLRLL LLLAATALLT HGQEEGQVEG QDEDIPPITC VQNGLRYHDR DVWKPEPCRI   60
CVCDNGKVLC DDVICDETKN CPGAEVPEGE CCPVCPDGSE SPTDQETTGV EGPKGDTGPR  120
GPRGPAGPPG RDGIPGQPGL PGPPGPPGPP GPPGLGGNFA PQLSYGYDEK STGGISVPGP  180
MGPSGPRGLP GPPGAPGPQG FQGPPGEPGE PGASGPMGPR GPPGPPGKNG DDGEAGKPGR  240
PGERGPPGPQ GARGLPGTAG LPGMKGHRGF SGLDGAKGDA GPAGPKGEPG SPGENGAPGQ  300
MGPRGLPGER GRPGAPGPAG ARGNDGATGA AGPPGPTGPA GPPGFPGAVG AKGEAGPQGP  360
RGSEGPQGVR GEPGPPGPAG AAGPAGNPGA DGQPGAKGAN GAPGIAGAPG FPGARGPSGP  420
QGPGGPPGPK GNSEPGAPG SKGDTGAKGE PGPVGVQGPP GPAGEEGKRG ARGEPGPTGL  480
PGPPGERGGP GSRGFPGADG VAGPKGPAGE RGSPGPAGPK GSPGEAGRPG EAGLPGAKGL  540

```
                                                -continued

TGSPGSPGPD GKTGPPGPAG QDGRPGPPGP PGARGQAGVM GFPGPKGAAG EPGKAGERGV    600
PGPPPGAVGPA GKDGEAGAQG PPGPAGPAGE RGEQGPAGSP GFQGLPGPAG PPGEAGKPGE    660
QGVPGDLGAP GPSGARGERG FPGERGVQGP PGPAGPRGAN GAPGNDGAKG DAGAPGAPGS    720
QGAPGLQGMP GERGAAGLPG PKGDRGDAGP KGADGSPGKD GVRGLTGPIG PPGPAGAPGD    780
KGESGPSGPA GPTGARGAPG DRGEPGPPGP AGFAGPPGAD PGPGAKGEPG DAGAKGDAGP    840
PGPAGPAGPP GPIGNVGAPG AKGARGSAGP PGATGFPGAA GRVGPPGPSG NAGPPGPPGP    900
AGKEGGKGPR GETGPAGRPG EVGPPGPPGP AGEKGSPGAD GPAGAPGTPG PQGIAGQRGV    960
VGLPGQRGER GFPGLPGPSG EPGKQGPSGA SGERGPPGPM GPPGLAGPPG ESGREGAPGA   1020
EGSPGRDGSP GAKGDRGETG PAGPPGAPGA PGAPGPVGPA GKSGDRGETG PAGPAGPVGP   1080
VGARGPAGPQ GPRGDKGETG EQGDRGIKGH RGFSGLQGPP GPPGSPGEQG PSGASGPAGP   1140
RGPPGSAGAP GKDGLNGLPG PIGPPGPRGR TGDAGPVGPP GPPGPPGPPG PPSAGFDFSF   1200
LPQPPQEKAH DGGRYYRADD ANVVRDRDLE VDTTLKSLSQ QIENIRSPEG SRKNPARTCR   1260
DLKMCHSDWK SGEYWIDPNQ GCNLDAIKVF CNMETGETCV YPTQPSVAQK NWYISKNPKD   1320
KRHVWFGESM TDGFQFEYGG QGSDPADVAI QLTFLRLMST EASQNITYHC KNSVAYMDQQ   1380
TGNLKKALLL QGSNEIEIRA EGNSRFTYSV TVDGCTSHTG AWGKTVIEYK TTKTSRLPII   1440
DVAPLDVGAP DQEFGFDVGP VCFL                                          1464

SEQ ID NO: 12          moltype = AA  length = 1487
FEATURE                Location/Qualifiers
source                 1..1487
                       mol_type = protein
                       organism = Homo sapiens
SEQUENCE: 12
MIRLGAPQTL VLLTLLVAAV LRCQGQDVQE AGSCVQDGQR YNDKDVWKPE PCRICVCDTG     60
TVLCDDIICE DVKDCLSPEI PFGECCPICP TDLATASGQP GPKGQKGEPG DIKDIVGPKG    120
PPGPQGPAGE QGPRGDRGDK GEKGAPGPRG RDGEPGTPGN PGPPGPPGPP GPPGLGGNFA    180
AQMAGGFDEK AGGAQLGVMQ GPMGPMGPRG PPGPAGAPGP QGFQGNPGEP GEPGVSGPMG    240
PRGPPGPPGK PGDDGEAGKP GKAGERGPPG PQGARGFPGT PGLPGVKGHR GYPGLDGAKG    300
EAGAPGVKGE SGSPGENGSP GPMGPRGLPG ERGRTGPAGA AGARGNDGQP GPAGPPGPVG    360
PAGGPGFPGA PGAKGEAGPT GARGPEGAQG PRGEPGTPGS PGPAGASGNP GTDGIPGAKG    420
SAGAPGIAGA PGFPGPRGPP GPQGATGPLG PKGQTGEPGI AGFKGEQGPK GEPGPAGPQG    480
APGPAGEEGK RGARGEPGGV GPIGPPGERG APGNRGFPGQ DGLAGPKGAP GERGPSGLAG    540
PKGANGDPGR PGEPGLPGAR GLTGRPGDAG PQGKVGPSGA PGEDGRPGPP GPQGARGQPG    600
VMGFPGPKGA NGEPGKAGEK GLPGAPGLRG LPGKDGETGA AGPPGPAGPA GERGEQGAPG    660
PSGFQGLPGP PGPPGEGGKP GDQGVPGEAG APGLVGPRGE RGFPGERGSP GAQGLQGPRG    720
LPGTPGTDGP KGASGPAGPP GAQGPPGLQG MPGERGAAGI AGPKGDRGDV GEKGPEGAPG    780
KDGGRGLTGP IGPPGPAGAN GEKGEVGPPG PAGSAGARGA PGERGETGPP GPAGFAGPPG    840
ADGQPGAKGE QGEAGQKGDA GAPGPQGPSG APGPQGPTGV TGPKGARGAQ GPPGATGFPG    900
AAGRVGPPGS NGNPGPPGPP GPSGKDGPKG ARGDSGPPGR AGEPGLQGPA GPPGEKGEPG    960
DDGPSGAEGP PGPQGLAGQR GIVGLPGQRG ERGFPGLPGP SGEPGKQGAP GASGDRGPPG   1020
PVGPPGLTGP AGEPGREGSP GADGPPGRDG AAGVKGDRGE TGAVGAPGAP GPPGSPGPAG   1080
PTGKQGDRGE AGAQGPMGPS GPAGARGIQG PQGPRGDKGE AGEPGERGLK GHRGFTGLQG   1140
LPGPPGPSGD QGASGPAGPS GPRGPPGPVG PSGKDGANGI PGPIGPPGPR GRSGETGPAG   1200
PPGNPGPPGP PGPPGPGIDM SAFAGLGPRE KGPDPLQYMR ADQAAGGLRQ HDAEVDATLK   1260
SLNNQIESIR SPEGSRKNPA RTCRDLKLCH PEWKSGDYWI DPNQGCTLDA MKVFCNMETG   1320
ETCVYPNPAN VPKKNWWSSK SKEKKHIWFG ETINGGFHFS YGDDNLAPNT ANVQMTFLRL   1380
LSTEGSQNIT YHCKNSIAYL DEAAGNLKKA LLIQGSNDVE IRAEGNSRFT YTALKDGCTK   1440
HTGKWGKTVI EYRSQKTSRL PIIDIAPMDI GGPEQEFGVD IGPVCFL                 1487
```

RECOMBINANT COLLAGEN AND PREPARATION METHOD AND USE THEREOF

CROSS REFERENCE TO THE RELATED APPLICATIONS

This application is the national phase entry of International Application No. PCT/CN2022/133595, filed on Nov. 23, 2022, which is based upon and claims priority to Chinese Patent Application No. 202111470250.8, filed on Dec. 3, 2021, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBNJIP142_Sequence Listing_20250422.xml, created on 04/22/2025, and is 35,362 bytes in size.

TECHNICAL FIELD

The present disclosure relates to a recombinant collagen and a preparation method and use thereof, and in particular to a full-length collagen α1 chain produced through recombinant expression, and a preparation method and use thereof. The present disclosure belongs to the technical field of collagen expression.

BACKGROUND

Type I collagen and type II collagen are typical fibrillar collagens in the human body. Type I collagen and type I collagen each are composed of three a peptide chains, and each a peptide chain contains an amino-terminal peptide region, a characteristic (G-X-Y)$_n$ triplet-repeat sequence region, and a carboxyl-terminal peptide region.

Type I collagen is composed of two α1 chains and one α2 chain. Type I collagen is the most abundant collagen among all types of collagen in the human body, and is found in muscles, skins, arterial walls, and fibrocartilage. Type II collagen is composed of three α1 chains, and is mainly distributed in cartilage tissues, vitreous humors, and corneas. The amount of type II collagen accounts for 90% or more of the total amount of collagen in an adult cartilage matrix. Type II collagen is an essential component for chondrogenic and skeletal pattern formation, skeletal growth, and mature cartilage maintenance.

As an important native biological protein, collagen has unique functional characteristics such as excellent biocompatibility, biological activity, and degradability. Therefore, collagen can be widely used in many fields such as chemical industry, medicine, food, and cosmetics, and is especially suitable for the preparation of various biological devices. Collagen is the most desirable source of biological materials and has promising application prospects.

Commercially available collagen products are mainly collagen extracts obtained by treating animal tissues with acid hydrolysis, alkaline hydrolysis, and enzymatic hydrolysis. However, during the above treatment process, collagen is severely degraded and thus loses its biological activity, and extracted collagen peptides have different lengths, heterogeneous properties, unstable qualities, and potential safety hazards from viral infections such as bovine spongiform encephalopathy and foot-and-mouth disease. In addition, animal-derived collagen has a quite different amino acid sequence from human-derived collagen, and is a heterologous protein, which will lead to immune rejection and allergic symptoms.

The production of a recombinant collagen through genetic engineering can effectively avoid these defects. Among the existing expression methods for recombinant collagen, expression systems such as mammalian cell expression systems, insect cell (baculovirus) expression systems, and transgenic animal and plant expression systems have characteristics such as high costs, low yield, and long cycle, and are mostly used for experiments at a scientific research stage. In large-scale industrial production, prokaryotic (*Escherichia coli*) expression systems and *Pichia pastoris* expression systems are mainly used to express human collagen. In *Escherichia coli*, there is no post-translational modification in the protein, and the protein is expressed intracellularly on a large scale. As a result, the bacterial cells need to be lysed, such that a large number of impurities such as host proteins and native endotoxins and peptidoglycans (as cell wall components) are produced, which can only be removed by a complicated purification process. Because human collagen is a foreign protein for *Pichia pastoris* after all, the expression of human collagen in *Pichia pastoris* occupies many intracellular resources (the methanol metabolism pathway relied by the above expression can result in the expression of up to 30% of soluble proteins in the cell), and *Pichia pastoris* cells will adjust correspondingly in response to a foreign protein. Typically, the recombinant protein is severely degraded in *Pichia pastoris*. α1 chains of human type I collagen and type U collagen each are a long peptide chain of 1,000 or more amino acids, and thus are prone to degradation.

α1 chains of human type I collagen and type II collagen each contain an amino-terminal peptide, a triple helix region, and a carboxyl-terminal peptide in a mature sequence thereof. A human type I collagen α1 chain (hereinafter canonically referred to as α1 (I)) has a full length of 1,057 amino acids (AA), and a human type II collagen α1 chain (hereinafter canonically referred to as α1 (II)) has a full length of 1,060 AA. There are many studies and patents on the expression of the human α1 (1) chain in *Pichia pastoris*, and few studies and patents on the expression of the human α1 (II) chain. In most of the existing studies on the expression of a full-length α1 (I) chain and a full-length α1 (II) chain in *Pichia pastoris*, only a part of the sequence of the α1 (I) chain, rather than the mature full-length sequence of the α1 (I) chain, is expressed. In some published findings, although a full-length α1 (I) chain is expressed, a main degradation product in substantially the same proportion as a target product is produced during the expression, and thus a main degradation band (the main degradation product) in substantially the same proportion as a target band (the target product) of the full-length α1 chain is presented during sodium dodecyl sulfate-polyacrylamide gel electrophoresis (SDS-PAGE). Such degradation results in reduced yield of the full-length α1 chain expressed. In addition, because the main degradation product has similar correlated properties to the full-length α1 chain, two-step tandem affinity purification is required to obtain a high-purity single full-length α1 chain product, which increases the complexity of the purification process and increases purification costs accordingly. Therefore, an important challenge for the production of a recombinant collagen in *Pichia pastoris* is to keep the full-length peptide chain intact and reduce the degradation, while maintaining the biological activity of the collagen unchanged.

SUMMARY

An objective of the present disclosure is to overcome some technical problems in the prior art, and to provide a full-length collagen α1 chain produced through recombinant expression in *Pichia pastoris*, and a preparation method and use thereof. Compared with native full-length α1 (1) and α1 (II) chains, when a variant of a recombinant human type I collagen α1 chain (which is denoted as α1 (I) M1) and a variant of a recombinant human type II collagen α1 chain (which is denoted as α1 (II) M6) according to the present disclosure are expressed in *Pichia pastoris*, a main degradation band (a main degradation product) in substantially the same proportion as a target band (a target product) of a full-length α1 chain is eliminated, and a yield of the target product is improved. The variants according to the present disclosure have similar physical and chemical characteristics and identical biological activity to the native full-length collagen α1 (I) and α1 (II) chains and commercially available human collagens expressed in *Pichia pastoris*, and thus both have application values in the field of biomedical materials.

To achieve the above objective, the present disclosure adopts the following technical solutions.

The present disclosure provides a recombinant collagen α1 chain, where the recombinant collagen α1 chain is α1 (I) M1 or α1 (II) M6; and the α1 (I) M1 is obtained through an amino acid mutation in a native full-length amino acid sequence of a human type I collagen α1 chain, and the α1 (II) M6 is obtained through an amino acid mutation in a native full-length amino acid sequence of a human type II collagen α1 chain.

Preferably, the α1 (I) M1 has 4 amino acid mutation sites, and the α1 (II) M6 has 9 amino acid mutation sites.

Preferably, the human type I collagen α1 chain is set forth in SEQ ID NO: 1; and the amino acid mutation sites include M at position 106, R at position 109, M at position 190, and R at position 193, and specifically, the amino acid mutation sites are mutated to P.

The human type II collagen α1 chain is set forth in SEQ ID NO: 4; and the amino acid mutation sites include V at position 67, M at position 68, M at position 72, M at position 75, R at position 78, M at position 108, R at position 11, M at position 162, and R at position 165, and specifically, the amino acid mutation sites are mutated to P.

Further, the α1 (I) M1 has an amino acid sequence as set forth in SEQ ID NO: 2, and the α1 (II) M6 has an amino acid sequence as set forth in SEQ ID NO: 5.

In the present disclosure, when the amino acid mutations at the amino acid mutation sites of the amino acid sequence are changed to some extent, that is, an amino acid(s) at the same amino acid mutation site(s) of the amino acid sequence is mutated to a different amino acid(s), technical effects similar to those of the present disclosure can also be obtained. When one or more of the amino acid mutation sites is/are changed, technical effects similar to those of the present disclosure may also be obtained.

The present disclosure also provides a nucleotide encoding the recombinant collagen α1 chain, where a sequence of the nucleotide encoding the recombinant collagen α1 chain includes a nucleotide sequence encoding the α1 (I) M1 or a nucleotide sequence encoding the α1 (II) M6.

Further, the nucleotide sequence encoding the α1 (I) M1 is set forth in SEQ ID NO: 3; and the nucleotide sequence encoding the α1 (II) M6 is set forth in SEQ ID NO: 6.

The present disclosure also provides a recombinant expression vector containing the nucleotide encoding the recombinant collagen α1 chain.

The present disclosure also provides an engineered strain constructed with the recombinant expression vector, where the engineered strain carries the recombinant expression vector or expresses the recombinant collagen α1 chain.

A host strain for the engineered strain is preferably *Pichia pastoris*. The engineered strain was deposited in the China General Microbiological Culture Collection Center (CGMCC) located at NO. 1, West Beichen Road, Chaoyang District, Beijing, China on Mar. 11, 2021, with an accession number of CGMCC NO. 21891 or CGMCC NO. 21892 and a taxonomic name of *Pichia pastoris*. The engineered strain with the accession number of CGMCC NO. 21891 expresses the recombinant collagen α1 chain α1 (I) M1, and the engineered strain with the accession number of CGMCC NO. 21892 expresses the recombinant collagen α1 chain α1 (II) M6.

It should be noted that the host strain of the present disclosure is not limited to *Pichia pastoris*. According to the method of the present disclosure, the recombinant collagen α1 chain can be produced by secretory expression in *Pichia pastoris* or other yeast species, and technical effects similar to those of the present disclosure can theoretically be obtained.

The present disclosure also provides a use of the recombinant expression vector or the engineered strain in an expression of the recombinant collagen α1 chain.

The present disclosure also provides a preparation method of the recombinant collagen α1 chain, including:

(1) Synthesizing a nucleotide sequence encoding the recombinant collagen α1 chain, where respective amino acids at amino acid mutation sites of an amino acid sequence of a native collagen α1 chain are mutated. 4 amino acids of a type I collagen α1 chain are mutated to obtain α1 (I) M1, and 9 amino acids of a type II collagen α1 chain are mutated to obtain α1 (II) M6. Affinity purification tags are added to an amino terminus and a carboxyl terminus of the amino acid sequence, and then a DNA sequence encoding α1 (I) M1 or α1 (11) M6 is synthesized, such that the DNA sequence includes bispecific affinity purification tags, which facilitates the immunological antibody detection based on the two tag sequences.

Detection results show that, when the α1 (I) M1 or α1 (II) M6 is expressed in *Pichia pastoris*, a main degradation band (a main degradation product) in substantially the same proportion as a target band (a target product) of a full-length α1 chain produced when the full-length α1 (I) chain or full-length α1 (II) chain is expressed in *Pichia pastoris* is eliminated.

Compared with the original native sequences, mutated amino acids in the α1 (I) M1 and α1 (II) M6 are located in a characteristic (G-X-Y), triplet-repeat sequence region, but all are amino acids located on X and Y, such that structural characteristics of an amino acid sequence of the $(G-X-Y)_n$ triplet-repeat sequence in collagen do not change. In addition, the α1 (I) M1 and α1 (II) M6 still maintain physical and chemical characteristics and biological activities similar to those of the original collagen.

(2) Constructing a recombinant expression vector;

where the synthesized DNA sequences are ligated to expression vectors pPIC9K to construct a recombinant expression vector pPIC9K-COL1A1M1 expressing the recombinant collagen α1 (I) M1 and a recombinant expression vector pPIC9K-COL2A1M6 expressing the recombinant collagen α1 (II) M6, respectively.

(3) Constructing recombinant engineered strains for an inducible expression, and screening the recombinant engineered strains;

where the recombinant expression vector is linearized with Sac I and then electrotransformed into *Pichia pastoris* competent cells, the electrotransformed *Pichia pastoris* competent cells are transferred to a Minimal Dextrose (MD) plate for primary screening and then further screened on Yeast Extract Peptone Dextrose (YPD) plates with different concentrations of G418, and then colonies are picked and inoculated into a Buffered Glycerol-complex Medium (BMGY medium) and subjected to inducible expression in a Buffered Methanol-complex Medium (BMMY medium). An engineered strain with a high expression level is screened out.

The engineered strain with the high expression level screened out is *Pichia pastoris*, and has an accession number of CGMCC NO. 21891 or CGMCC NO. 21892.

(4) Cultivating for high-density fermentation;

where the engineered strain with the high expression level identified through protein expression is cultivated in a fermentation tank for a high-density fermentation to obtain a fermentation supernatant.

(5) Purifying the fermentation supernatant to obtain a protein;

where the fermentation supernatant is purified by one-step cation exchange chromatography and then lyophilized to obtain a high-purity collagen α1 (I) M1 or α1 (II) M6.

The obtained recombinant collagen α1 (I) M1 and recombinant collagen α1 (II) M6 expressed in *Pichia pastoris* according to the present disclosure are analyzed through protein property characterization and in vitro experiments. The recombinant collagen α1 (I) M1 and recombinant collagen α1 (II) M6 obtained in the present disclosure have structural characteristics of recombinant collagen, have cell adhesion activities, and are substantially consistent with the commercially available human collagens. More importantly, the two variant proteins of the present disclosure have similar or identical structural characteristics and cell adhesion activities compared with the unmutated original collagen.

The present disclosure also provides a composition including the recombinant collagen α1 chain or a collagen α1 chain prepared by the preparation method described above.

The present disclosure also provides an article including the recombinant collagen α1 chain or a collagen α1 chain prepared by the preparation method described above or the composition described above. The article includes, but is not limited to, a drug, a pharmaceutical composition, a medical device, a biological material, a tissue-engineered product, a cosmetic, or a health product.

Further, the article includes a material for providing an adhesion, a support, and a growth and migration space for a cell or a material serving as a channel for delivering a nutrient and a metabolite.

Further, the article is a collagen hydrogel.

The present disclosure also provides a use of the recombinant collagen α1 chain, the nucleotide, the recombinant expression vector, the engineered strain, or the composition in the manufacture of a product, where the product includes, but is not limited to, a drug, a medical device, a biological material, a tissue-engineered product, a cosmetic, or a health product.

The present disclosure also provides a use of the recombinant collagen α1 chain, the nucleotide, the recombinant expression vector, the engineered strain, or the composition in the manufacture of a product for promoting wound healing or tissue regeneration. Further, the product is a collagen hydrogel.

The present disclosure has the following advantages.

(1) In the collagen α1 chain variants of the present disclosure, a proportion of the amino acid mutation sites in the original native sequence is very small (the proportion of mutated amino acids is lower than 1%, and a homology between amino acid sequences before and after mutation is higher than 99%), such that the complete recombinant α1 chain collagen is obtained without changing the properties (physical and chemical characteristics and biological activity) of the original protein itself, and the collagen α1 chain variants of the present disclosure have the same properties and biological activities as a recombinant protein of a native sequence when prepared into related products.

The α1 (I) M1 and α1 (II) M6 have physical and chemical characteristics and biological activities similar to those of α1 (I) and α1 (II), respectively, and both have application values in the field of biomedical materials. In the present disclosure, it is found through cell adhesion experiments on α1 (I) M1, α1 (II) M6, α1 (I), and α1 (II) that, there is no significant difference in the cell adhesion activity between α1 (1) and α1 (I) M1 and between α1 (II) M6 and α1 (II), and the cell adhesion activities of the α1 (I) M1 and α1 (II) M6 are substantially consistent with those of the commercially available human collagens. Collagen hydrogels are prepared from collagens α1 (I) M1, α1 (II) M6, α1 (I), and α1 (II) expressed in *Pichia pastoris*, and hydromechanical characteristics of the collagen hydrogels are tested. There is no significant difference in the viscosity, elasticity modulus, and swelling degree between the collagen hydrogel prepared from α1 (I) and the collagen hydrogel prepared from α1 (I) M1 and between the collagen hydrogel prepared from α1 (II) M6 and the collagen hydrogel prepared from α1 (II). Lyophilized collagen hydrogels are scanned by scanning electron microscopy (SEM). These collagen hydrogels all have a porous network structure and a pore size ranging from 100 μm to 200 μm, and have the potential to be applied in the field of biomedical materials. The four collagen hydrogels each are co-cultivated with NIH/3T3 cells in vitro). After Calcein Acetoxymethyl Ester (Calcein AM) is added, viable cells exhibiting green fluorescence that adhere to the collagen hydrogel and grow in the collagen hydrogel can be detected. After methylthiazolyldiphenyl-tetrazolium bromide (MTT) is added, blue-purple crystals produced by viable cells that adhere to the collagen hydrogel and migrate and grow into the collagen hydrogel can be observed.

(2) In the present disclosure, expressed proteins are identified by SDS-PAGE and Western blot (WB). Identification results show that, compared with the full-length α1 (I) chain and full-length α1 (II) chain, when the α1 (I) M1 and α1 (II) M6 are expressed in *Pichia pastoris*, a main degradation band (a main degradation product) in substantially the same proportion as a target band (a target product) of a full-length α1 chain is eliminated, and the yield of the target product is improved. In addition, a high-density fermentation experiment is performed in a fermentation tank, and fermentation products are detected by SDS-PAGE. It can be found that α1 (I) M1 and α1 (II) M6 each can still maintain the integrity of the target band and do not lead to a main degradation band under high-density fermentation conditions, while the recombinant human α1 (1) and α1 (II) produced by fermentation under the same high-density fermentation conditions lead to obvious main degradation bands.

Moreover, for the recombinant collagen of the present disclosure, the fermentation supernatant only needs to be purified by one-step cation exchange chromatography and then lyophilized to obtain the lyophilized high-purity α1 (I) M1 or α1 (II) M6 collagen sponge. The collagen sponge is detected by SDS-PAGE, and there is mainly a single band of the target product, and no main degradation band, indicating that the high-purity target product is obtained. In the present disclosure, the cost of purification is reduced. However, for α1 (I) and α1 (II), after the fermentation supernatant is purified by one-step cation exchange chromatography, a purified protein product that is a mixture of a target band (a target product, a full-length α1 chain) and a main degradation band (a main degradation product) can only be obtained. Thus, two-step affinity chromatography is required to obtain the high-purity collagen α1 (I) or α1 (II).

BRIEF DESCRIPTION OF THE DRAWINGS

FIG. 1 shows differences between amino acid sequences of α1 (I) M1 (SEQ ID NO: 2) and α1 (T) (SEQ ID NO: 1), where amino acids in bold and gray background indicate difference sites.

FIG. 2 shows differences between amino acid sequences of α1 (II) M6 (SEQ ID NO: 5) and α1 (II) (SEQ ID NO: 4), where amino acids in bold and gray background indicate difference sites.

FIG. 6A is a WB pattern with an anti-6×His Tag antibody and FIG. 6B is a WB pattern with an anti-Strep-Tag II antibody.

Figure 7A:
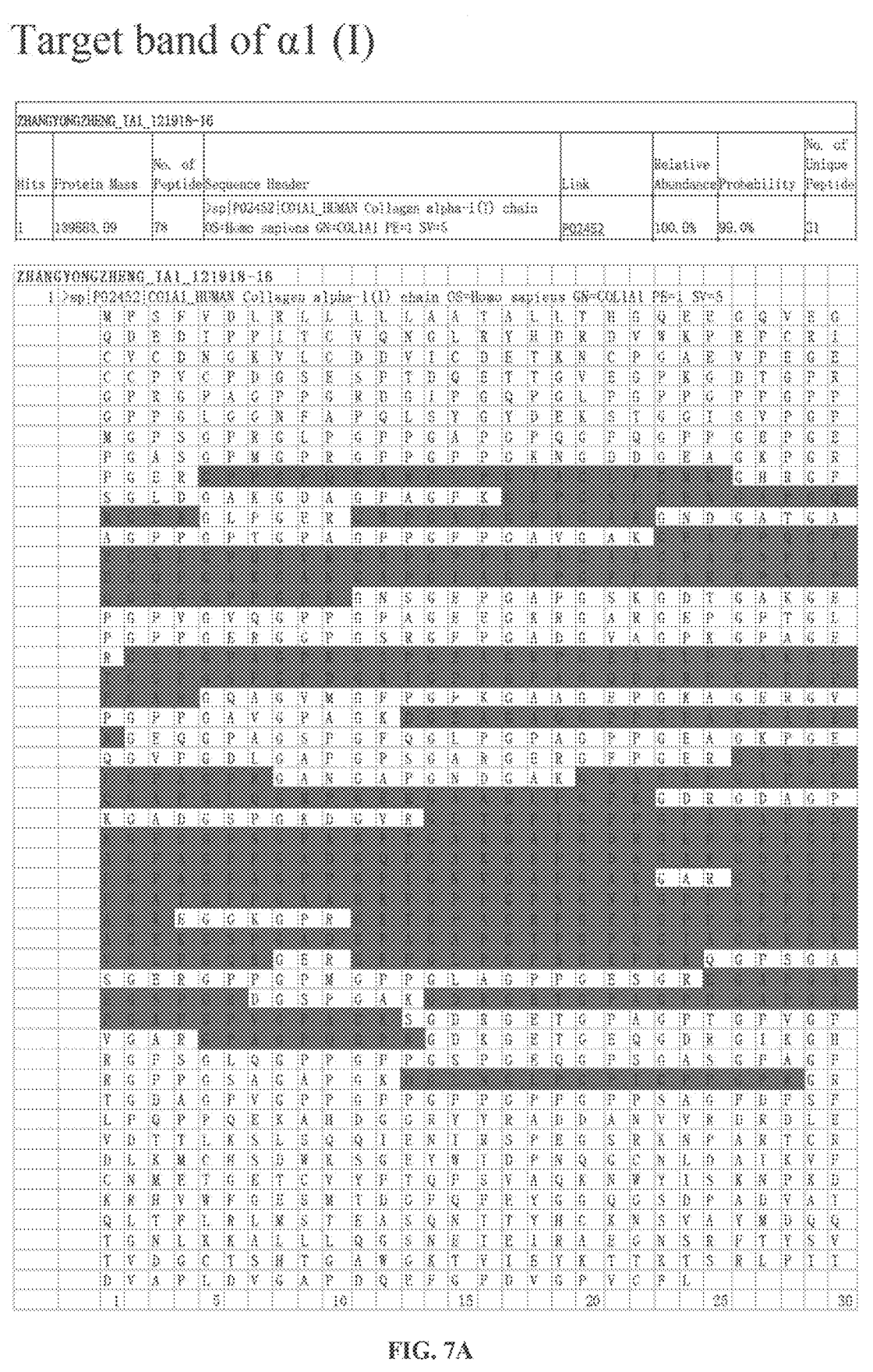
Figure 7B:
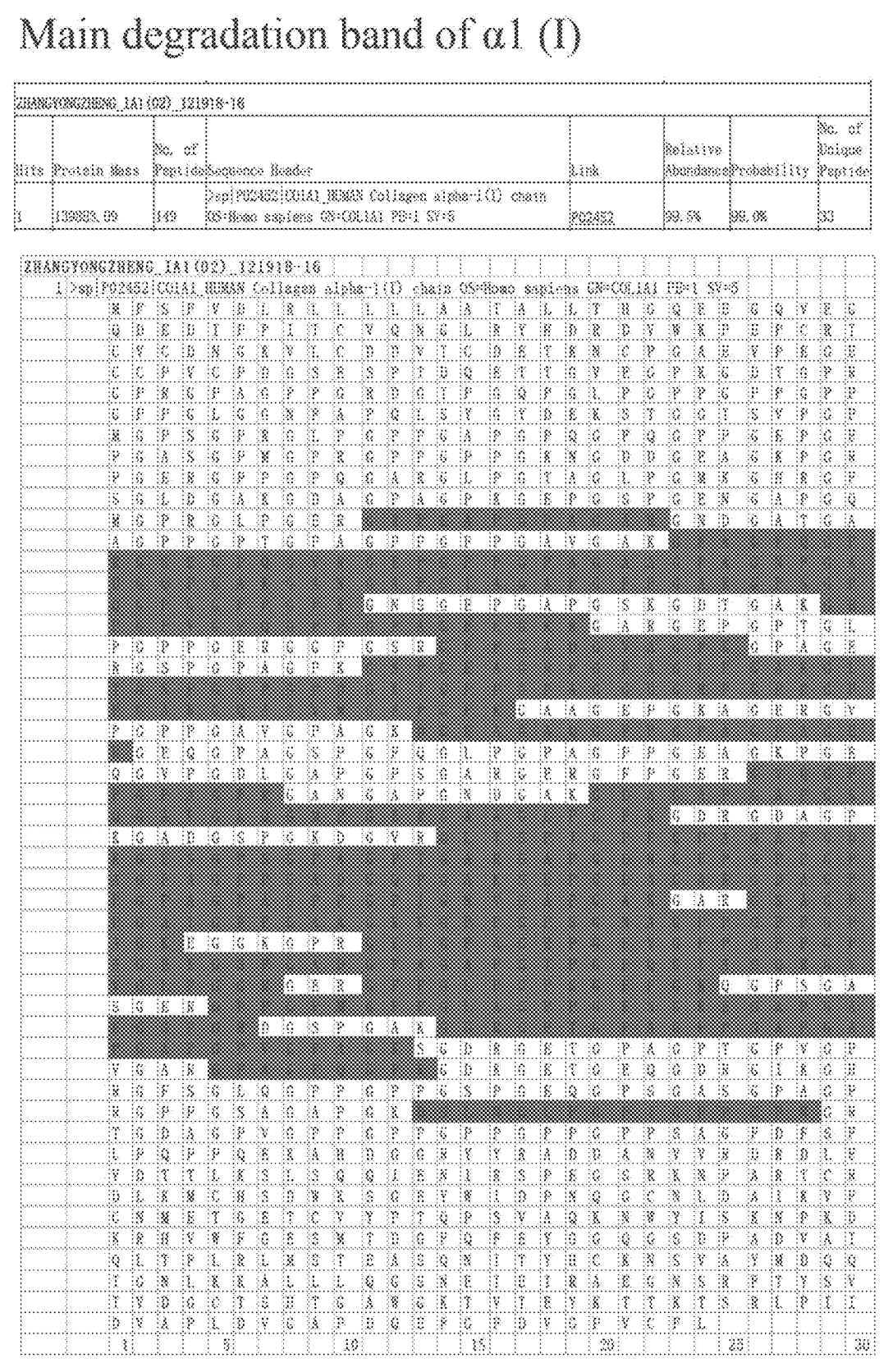
Figure 7C:
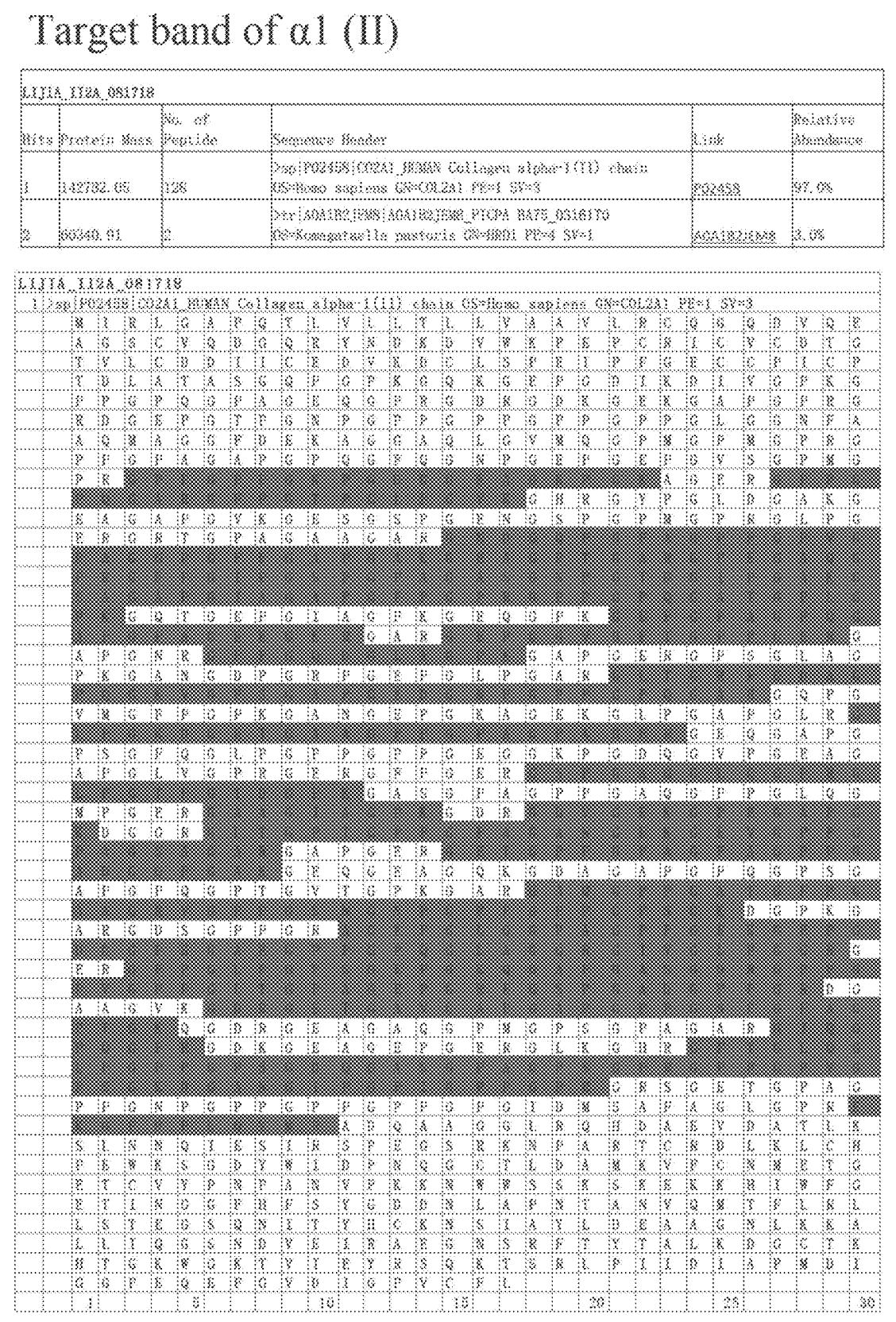
Figure 7D:
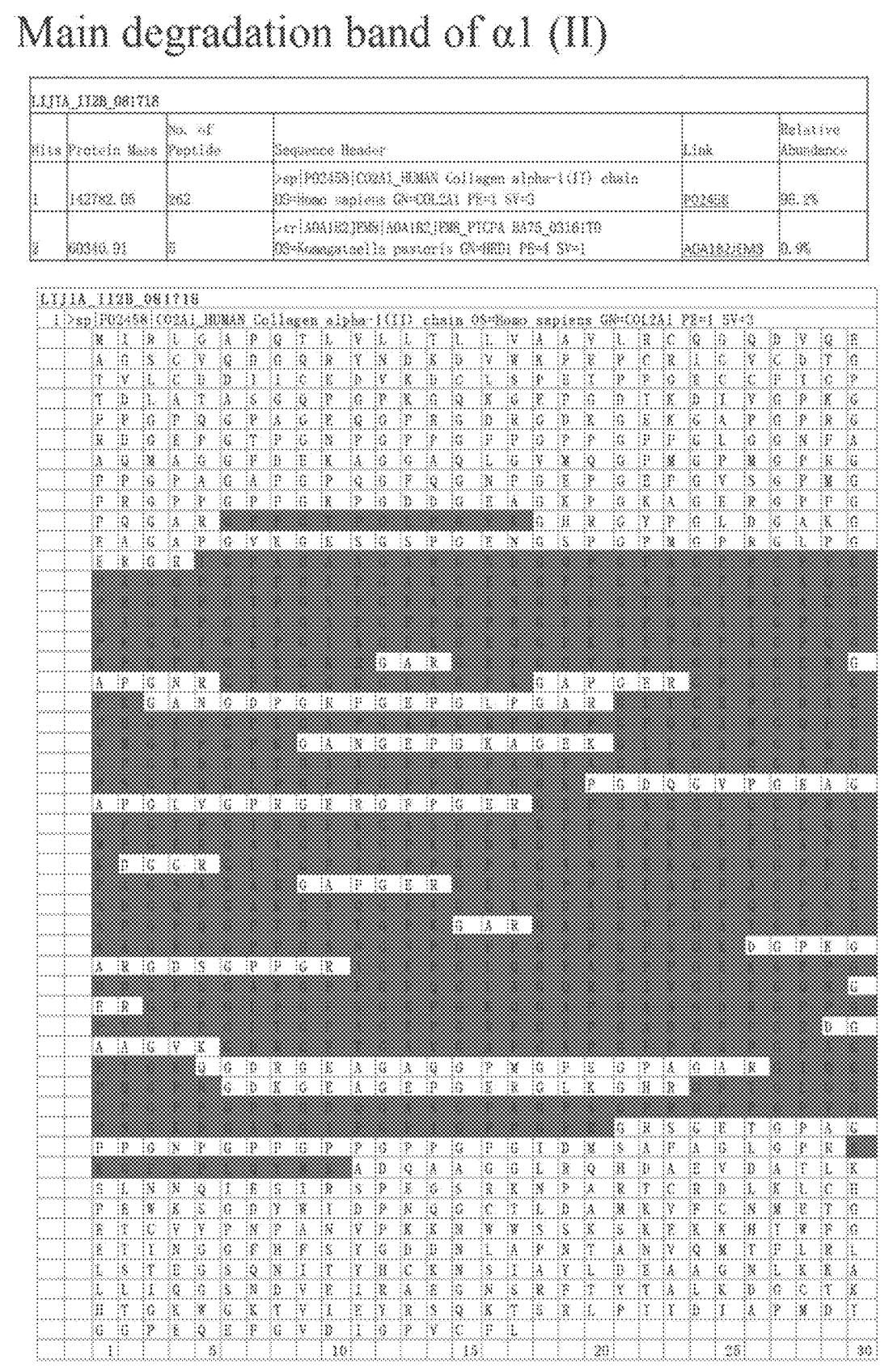

FIG. 7A (SEQ ID NO: 11), FIG. 7B (SEQ ID NO: 11), FIG. 7C (SEQ ID NO: 12), and FIG. 7D (SEQ ID NO: 12) show mass spectrometry results of target bands and main degradation bands in SDS-PAGE results of α1 (I) and α1 (II) collagens.

FIGS. 16A-16C show the following respectively: NIH/3T3 cells growing adherently on the α1 (I) collagen hydrogel (the image being taken with a brightfield microscope), NIH/3T3 cells growing adherently on the α1 (I) collagen hydrogel (stained with Calcein AM, bright parts show cells exhibiting green fluorescence, and the image being taken with a fluorescence microscope), and blue-purple crystals produced by NIH/3T3 cells growing in the α1 (I) collagen hydrogel (stained with MTT, dark parts show the crystals, and the image being taken with a brightfield microscope); and FIGS. 16D-16F show the following respectively: NIW3T3 cells growing adherently on the α1 (I) M1 collagen hydrogel (the image being taken with a brightfield microscope), NIH/3T3 cells growing adherently on the α1 (I) M1 collagen hydrogel (stained with Calcein AM, bright parts show cells exhibiting green fluorescence, and the image being taken with a fluorescence microscope), and blue-purple crystals produced by NIH/3T3 cells growing in the α1 (I) M1 collagen hydrogel (stained with MTT, dark parts show the crystals, and the image being taken with a brightfield microscope).

FIGS. 17A-17C show the following respectively: NIH/3T3 cells growing adherently on the α1 (II) collagen hydrogel (the image being taken with a brightfield microscope), NIH/3T3 cells growing adherently on the α1 (II) collagen hydrogel (stained with Calcein AM, bright parts show cells exhibiting green fluorescence, and the image being taken with a fluorescence microscope), and blue-purple crystals produced by NIH/3T3 cells growing in the α1 (II) collagen hydrogel (stained with MTT, dark parts show the crystals, and the image being taken with a brightfield microscope); and FIGS. 17D-17F show the following respectively: NIH/3T3 cells growing adherently on the α1 (II) M6 collagen hydrogel (the image being taken with a brightfield microscope), NIW3T3 cells growing adherently on the α1 (II) M6 collagen hydrogel (stained with Calcein AM, bright parts show cells exhibiting green fluorescence, and the image being taken with a fluorescence microscope), and blue-purple crystals produced by NIH/3T3 cells growing in the α1 (II) M6 collagen hydrogel (stained with MTT, dark parts show the crystals, and the image being taken with a brightfield microscope).

DETAILED DESCRIPTION OF THE EMBODIMENTS

Figure 3:
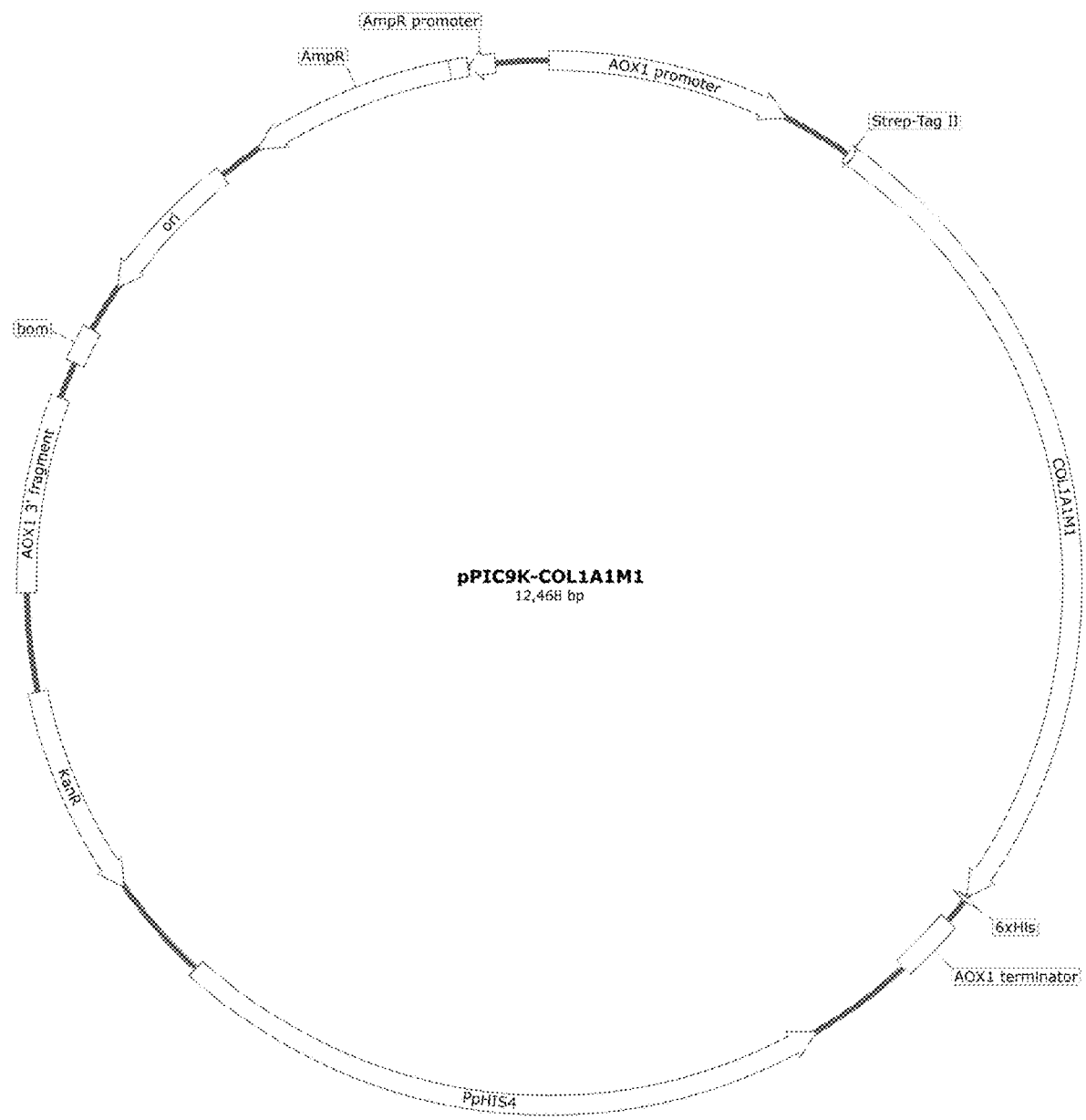
FIG. 3 is a map of a pPIC9K-COL1 A1M1 vector.

In order to make those skilled in the art better understand the technical solutions of the present disclosure, the preferred examples of the present disclosure are described in detail below, but the following examples do not limit the protection scope of the present disclosure.

In the examples of the present disclosure, those not described in detail are all implemented by a conventional molecular biology experimental method; and processes such as polymerase chain reaction (PCR), enzyme digestion, ligation, and codon optimization involved in the examples can all be understood and easily implemented by those skilled in the art according to product instructions or basic knowledge in the art, and thus will not be described in detail.

Example 1 Design and Synthesis of Amino Acid Sequences

With reference to positions 162 to 1218 (PRO_0000005720) of a P02452-1 (uniprot.org) sequence in the Uniprot database, an amino acid sequence of a human type I collagen α1 chain (denoted as α1 (I)) is an amino acid sequence of a human type I collagen α1 chain in a mature form, and does not include regions that would be processed and cleaved in α1 (I) proprotein, such as a signal peptide, a C-terminal propeptide, and an N-terminal propeptide, and is set forth in SEQ ID NO: 1.

```
SEQ ID NO: 1:
QLSYGYDEKSTGGISVPGPMGPSGPRGLPGPPGAPGPQGFQGPPGEPGEPGASGPM

GPRGPPGPPGKNGDDGEAGKPGRPGERGPPGPQGARGLPGTAGLPGMKGHRGFSGLDG

AKGDAGPAGPKGEPGSPGENGAPGQMGPRGLPGERGRPGAPGPAGARGNDGATGAAG

PPGPTGPAGPPGFPGAVGAKGEAGPQGPRGSEGPQGVRGEPGPPGPAGAAGPAGNPGA

DGQPGAKGANGAPGIAGAPGFPGARGPSGPQGPGGPPGPKGNSGEPGAPGSKGDTGAK

GEPGPVGVQGPPGPAGEEGKRGARGEPGPTGLPGPPGERGGPGSRGFPGADGVAGPKGP

AGERGSPGPAGPKGSPGEAGRPGEAGLPGAKGLTGSPGSPGPDGKTGPPGPAGQDGRPG

PPGPPGARGQAGVMGFPGPKGAAGEPGKAGERGVPGPPGAVGPAGKDGEAGAQGPPG

PAGPAGERGEQGPAGSPGFQGLPGPAGPPGEAGKPGEQGVPGDLGAPGPSGARGERGFP

GERGVQGPPGPAGPRGANGAPGNDGAKGDAGAPGAPGSQGAPGLQGMPGERGAAGLP

GPKGDRGDAGPKGADGSPGKDGVRGLTGPIGPPGPAGAPGDKGESGPSGPAGPTGARG

APGDRGEPGPPGPAGFAGPPGADGQPGAKGEPGDAGAKGDAGPPGPAGPAGPPGPIGN

VGAPGAKGARGSAGPPGATGFPGAAGRVGPPGPSGNAGPPGPPGPAGKEGGKGPRGET

GPAGRPGEVGPPGPPGPAGEKGSPGADGPAGAPGTPGPQGIAGQRGVVGLPGQRGERGF

PGLPGPSGEPGKQGPSGASGERGPPGPMGPPGLAGPPGESGREGAPGAEGSPGRDGSPG

AKGDRGETGPAGPPGAPGAPGAPGPVGPAGKSGDRGETGPAGPAGPVGPVGARGPAGP

QGPRGDKGETGEQGDRGIKGHRGFSGLQGPPGPPGSPGEQGPSGASGPAGPRGPPGSAG

APGKDGLNGLPGPIGPPGPRGRTGDAGPVGPPGPPGPPGPPGPPSAGFDFSFLPQPPQEKA

HDGGRYYRA.
```

A long-term experimental research was performed to obtain a variant of a recombinant human type I collagen α1 chain, which was denoted as α1 (I) M1. Compared with the amino acid sequence of α1 (I), 4 amino acids were mutated to proline (Pro, abbreviated as P) in α1 (I) M1. That is, M at position 106, R at position 109, M at position 190, and R at position 193 in the amino acid sequence set forth in SEQ ID NO: 1 all were mutated to P, and the remaining amino acids in the amino acid sequence remained unchanged. A homology of α1 (I) M1 with α1 (T) was 99.6%.

The mutated amino acid sequence (α1 (I) M1) has a full length of 1,057 AA, and is set forth in SEQ ID NO: 2.

```
SEQ ID NO: 2:
QLSYGYDEKSTGGISVPGPMGPSGPRGLPGPPGAPGPQGFQGPPGEPGEPGASGPPG

PPGPPGPPGKNGDDGEAGKPGRPGERGPPGPQGARGLPGTAGLPGMKGHRGFSGLDGA

KGDAGPAGPKGEPGSPGENGAPGQPGPPGLPGERGRPGAPGPAGARGNDGATGAAGPP
```

```
GPTGPAGPPGFPGAVGAKGEAGPQGPRGSEGPQGVRGEPGPPGPAGAAGPAGNPGADG

QPGAKGANGAPGIAGAPGFPGARGPSGPQGPGGPPGPKGNSGEPGAPGSKGDTGAKGE

PGPVGVQGPPGPAGEEGKRGARGEPGPTGLPGPPGERGGPGSRGFPGADGVAGPKGPA

GERGSPGPAGPKGSPGEAGRPGEAGLPGAKGLTGSPGSPGPDGKTGPPGPAGQDGRPGP

PGPPGARGQAGVMGFPGPKGAAGEPGKAGERGVPGPPGAVGPAGKDGEAGAQGPPGP

AGPAGERGEQGPAGSPGFQGLPGPAGPPGEAGKPGEQGVPGDLGAPGPSGARGERGFP

GERGVQGPPGPAGPRGANGAPGNDGAKGDAGAPGAPGSQGAPGLQGMPGERGAAGLP

GPKGDRGDAGPKGADGSPGKDGVRGLTGPIGPPGPAGAPGDKGESGPSGPAGPTGARG

APGDRGEPGPPGPAGFAGPPGADGQPGAKGEPGDAGAKGDAGPPGPAGPAGPPGPIGN

VGAPGAKGARGSAGPPGATGFPGAAGRVGPPGPSGNAGPPGPPGPAGKEGGKGPRGET

GPAGRPGEVGPPGPPGPAGEKGSPGADGPAGAPGTPGPQGIAGQRGVVGLPGQRGERGF

PGLPGPSGEPGKQGPSGASGERGPPGPMGPPGLAGPPGESGREGAPGAEGSPGRDGSPG

AKGDRGETGPAGPPGAPGAPGAPGPVGPAGKSGDRGETGPAGPAGPVGPVGARGPAGP

QGPRGDKGETGEQGDRGIKGHRGFSGLOGPPGPPGSPGEQGPSGASGPAGPRGPPGSAG

APGKDGLNGLPGPIGPPGPRGRTGDAGPVGPPGPPGPPGPPGPSAGFDFSFLPQPPQEKA

HDGGRYYRA.
```

Differences between the amino acid sequences of α1 (1) M1 and α1 (I) are shown by amino acids in bold and gray background in FIG. 1.

A DNA sequence of a gene (denoted as COL1A1M1) encoding the α1 (1) M1 set forth in SEQ ID NO: 2 is set forth in SEQ ID NO: 3.

```
SEQ ID NO: 3:
CAACTTAGTTATGGATACGATGAAAAATCCACAGGTGGAATCAGTGTTCCTGGA

CCTATGGGTCCATCAGGTCCAAGAGGTTTACCAGGACCTCCAGGTGCCCCAGGTCCC

CAGGGATTTCAAGGTCCACCAGGAGAGCCTGGTGAGCCAGGAGCTTCTGGTCCACC

TGGTCCCCCTGGACCACCTGGTCCTCCAGGAAAGAATGGAGATGATGGTGAAGCTG

GAAAACCTGGAAGACCTGGAGAAGAGGACCACCAGGACCCCAGGGTGCCAGAGG

ACTGCCAGGTACCGCAGGTCTGCCTGGAATGAAAGGTCATAGAGGATTTTCAGGATT

AGACGGTGCAAAGGGAGACGCTGGACCTGCAGGACCAAAGGGTGAGCCAGGAAGT

CCAGGAGAGAATGGTGCACCAGGACAGCCAGGTCCACCTGGACTGCCCGGTGAAAG

AGGTAGACCCGGAGCACCAGGACCAGCAGGTGCAAGAGGAAATGATGGAGCTACA

GGTGCTGCAGGACCCCCAGGTCCAACAGGACCAGCCGGTCCTCCCGGTTTCCCAGGT

GCCGTTGGAGCAAAAGGTGAAGCTGGTCCACAGGGTCCAAGAGGTTCTGAAGGTCC

ACAGGGAGTTAGAGGAGAACCAGGACCCCCTGGACCAGCTGGTGCAGCAGGACCA

GCTGGTAACCCTGGTGCTGACGGTCAGCCAGGTGCTAAGGGAGCAAATGGAGCACC

AGGAATAGCTGGTGCCCCAGGATTTCCCGGTGCTAGAGGTCCAAGTGGTCCACAAG

GACCAGGAGGTCCACCCGGTCCCAAAGGAAACAGTGGAGAACCAGGTGCACCCGGT

TCAAAGGGAGATACAGGAGCTAAAGGAGAGCCCGGTCCAGTGGGTGTTCAGGGACC

ACCCGGACCTGCTGGAGAGGAAGGTAAAAGAGGTGCAAGAGGTGAGCCAGGACCA

ACAGGTCTGCCTGGTCCCCCTGGTGAAAGAGGTGGTCCAGGTAGTAGAGGATTTCCA

GGAGCTGATGGTGTTGCAGGACCAAAGGGACCCGCAGGTGAGAGAGGATCACCCGG
```

-continued

```
TCCAGCCGGACCAAAAGGATCACCAGGAGAAGCTGGTAGACCAGGAGAAGCTGGT
CTGCCAGGTGCTAAAGGATTGACAGGATCACCCGGTTCACCTGGTCCTGATGGAAA
GACAGGACCTCCAGGTCCCGCTGGTCAGGACGGTAGACCAGGACCCCCAGGACCCC
CAGGTGCAAGAGGTCAGGCAGGTGTAATGGGTTTCCCCGGACCTAAAGGAGCAGCT
GGAGAACCTGGTAAAGCTGGAGAGAGAGGAGTGCCTGGACCCCCTGGAGCTGTTGG
TCCAGCAGGAAAGGATGGTGAGGCAGGTGCACAAGGTCCACCTGGACCCGCTGGAC
CTGCAGGTGAGAGAGGAGAGCAAGGTCCCGCAGGTTCTCCAGGTTTTCAGGGTTTG
CCAGGTCCAGCCGGTCCTCCTGGAGAGGCAGGAAAGCCAGGAGAACAAGGAGTTCC
AGGAGACCTGGGTGCACCAGGACCCTCTGGTGCAAGAGGAGAGAGAGGATTTCCTG
GAGAAAGAGGTGTGCAGGGACCACCAGGTCCCGCCGGTCCAAGAGGAGCAAATGG
AGCCCCTGGAAATGACGGAGCTAAGGGTGACGCTGGTGCACCAGGAGCACCAGGTT
CTCAAGGTGCTCCCGGATTGCAGGGTATGCCTGGAGAGAGAGGTGCAGCTGGACTG
CCAGGTCCAAAAGGTGACAGAGGAGACGCCGGTCCTAAGGGAGCTGACGGTTCTCC
TGGAAAGGACGGTGTGAGAGGTTTGACAGGACCAATAGGTCCACCCGGTCCTGCTG
GAGCCCCTGGAGACAAAGGTGAATCAGGTCCTTCCGGTCCAGCCGGACCAACAGGA
GCAAGAGGAGCACCTGGAGACAGAGGAGAGCCAGGTCCTCCAGGACCTGCAGGTTT
CGCTGGTCCTCCCGGAGCAGATGGACAGCCAGGAGCTAAGGGAGAACCCGGTGACG
CTGGTGCTAAGGGAGATGCAGGTCCACCAGGTCCTGCTGGTCCTGCTGGACCTCCCG
GACCAATAGGTAATGTTGGAGCACCCGGAGCAAAAGGTGCCAGAGGTTCCGCAGGT
CCTCCCGGAGCAACTGGTTTTCCAGGAGCTGCCGGAAGAGTGGGTCCACCTGGTCCT
TCTGGAAATGCAGGACCACCAGGTCCTCCTGGTCCAGCCGGAAAGGAAGGTGGAAA
GGGACCTAGAGGAGAAACAGGTCCCGCAGGTAGACCCGGTGAGGTGGGTCCACCTG
GTCCACCCGGTCCAGCTGGTGAGAAAGGAAGTCCTGGAGCAGACGGACCAGCTGGT
GCCCCTGGTACACCAGGACCCCAAGGAATAGCTGGTCAAAGAGGTGTTGTTGGTTTA
CCAGGTCAGAGAGGAGAAAGAGGTTTTCCAGGATTACCAGGTCCCTCAGGTGAGCC
CGGAAAACAGGGTCCCTCAGGAGCAAGTGGTGAAAGAGGACCACCAGGACCAATG
GGACCTCCAGGATTAGCTGGTCCACCAGGAGAATCAGGAAGAGAGGGTGCTCCTGG
AGCAGAAGGTTCACCAGGAAGAGACGGTTCACCCGGAGCCAAGGGAGACAGAGGT
GAAACAGGTCCCGCAGGTCCACCAGGAGCACCCGGAGCCCTGGTGCTCCAGGACC
TGTCGGACCAGCAGGAAAATCCGGTGACAGAGGTGAGACTGGACCCGCAGGTCCTG
CTGGTCCTGTTGGACCAGTGGGTGCAAGAGGACCAGCAGGTCCACAAGGTCCAAGA
GGTGACAAAGGTGAGACAGGTGAGCAGGGTGACAGAGGAATTAAAGGTCACAGAG
GATTTTCAGGACTGCAGGGACCACCCGGTCCTCCCGGTTCCCCAGGAGAGCAAGGT
CCATCCGGTGCATCCGGTCCAGCTGGACCCAGAGGACCACCTGGTTCTGCTGGTGCA
CCAGGTAAAGATGGATTGAACGGTTTGCCTGGTCCAATAGGACCTCCTGGTCCAAGA
GGAAGAACTGGTGACGCCGGTCCCGTCGGACCACCCGGTCCACCAGGTCCCCCAGG
TCCACCCGGACCACCATCCGCAGGATTTGATTTCTCATTCCTTCCTCAACCTCCTCAA
GAGAAAGCACATGATGGAGGTAGATACTATAGAGCC.
```

With reference to positions 182 to 1241 (PRO_0000005730) of a P02458 (uniprot.org) sequence in the Uniprot database, an amino acid sequence of a human type II collagen α1 chain (denoted as α1 (II)) is an amino acid sequence of a human type II collagen α1 chain in a mature form, and does not include regions that would be processed and cleaved in α1 (II) proprotein, such as a signal peptide, a C-terminal propeptide, and an N-terminal propeptide, and is set forth in SEQ ID NO: 4.

```
SEQ ID NO: 4:
QMAGGFDEKAGGAQLGVMQGPMGPMGPRGPPGPAGAPGPQGFQGNPGEPGEPG

VSGPMGPRGPPGPPGKPGDDGEAGKPGKAGERGPPGPQGARGFPGTPGLPGVKGHRGY

PGLDGAKGEAGAPGVKGESGSPGENGSPGPMGPRGLPGERGRTGPAGAAGARGNDGQ

PGPAGPPGPVGPAGGPGFPGAPGAKGEAGPTGARGPEGAQGPRGEPGTPGSPGPAGASG

NPGTDGIPGAKGSAGAPGIAGAPGFPGPRGPPGPQGATGPLGPKGQTGEPGIAGFKGEQG

PKGEPGPAGPQGAPGPAGEEGKRGARGEPGGVGPIGPPGERGAPGNRGFPGQDGLAGP

KGAPGERGPSGLAGPKGANGDPGRPGEPGLPGARGLTGRPGDAGPQGKVGPSGAPGED

GRPGPPGPQGARGQPGVMGFPGPKGANGEPGKAGEKGLPGAPGLRGLPGKDGETGAA

GPPGPAGPAGERGEQGAPGPSGFQGLPGPPGPPGEGGKPGDQGVPGEAGAPGLVGPRGE

RGFPGERGSPGAQGLQGPRGLPGTPGTDGPKGASGPAGPPGAQGPPGLQGMPGERGAA

GIAGPKGDRGDVGEKGPEGAPGKDGGRGLTGPIGPPGPAGANGEKGEVGPPGPAGSAG

ARGAPGERGETGPPGPAGFAGPPGADGQPGAKGEQGEAGQKGDAGAPGPQGPSGAPGP

QGPTGVTGPKGARGAQGPPGATGFPGAAGRVGPPGSNGNPGPPGPPGPSGKDGPKGAR

GDSGPPGRAGEPGLQGPAGPPGEKGEPGDDGPSGAEGPPGPQGLAGQRGIVGLPGQRGE

RGFPGLPGPSGEPGKQGAPGASGDRGPPGPVGPPGLTGPAGEPGREGSPGADGPPGRDG

AAGVKGDRGETGAVGAPGAPGPPGSPGPAGPTGKQGDRGEAGAQGPMGPSGPAGARG

IQGPQGPRGDKGEAGEPGERGLKGHRGFTGLQGLPGPPGPSGDQGASGPAGPSGPRGPP

GPVGPSGKDGANGIPGPIGPPGPRGRSGETGPAGPPGNPGPPGPPGPGPGIDMSAFAGLG

PREKGPDPLQYMRA.
```

A long-term experimental research was performed to obtain a variant of a recombinant human type II collagen α1 chain, which was denoted as α1 (IT) M6. Compared with the amino acid sequence of α1 (II), 9 amino acids were mutated to proline (Pro, abbreviated as P) in α1 (II) M6. That is, V at position 67, M at position 68, M at position 72, M at position 75, R at position 78, M at position 108, R at position 11, M at position 162, and R at position 165 in the amino acid sequence set forth in SEQ ID NO: 4 all were mutated to P, and the remaining amino acids in the amino acid sequence remained unchanged. A homology of α1 (II) M6 with α1 (II) was 99.2%.

The mutated amino acid sequence (α1 (II) M6) has a full length of 1,060 AA, and is set forth in SEQ ID NO: 5.

```
SEQ ID NO: 5:
QMAGGFDEKAGGAQLGPPQGPPGPPGPPGPGPAGAPGPQGFQGNPGEPGEPGVS

GPPGPPGPPGPPGKPGDDGEAGKPGKAGERGPPGPQGARGFPGTPGLPGVKGHRGYPGL

DGAKGEAGAPGVKGESGSPGENGSPGPPGPPGLPGERGRTGPAGAAGARGNDGQPGPA

GPPGPVGPAGGPGFPGAPGAKGEAGPTGARGPEGAQGPRGEPGTPGSPGPAGASGNPGT

DGIPGAKGSAGAPGIAGAPGFPGPRGPPGPQGATGPLGPKGQTGEPGIAGFKGEQGPKGE

PGPAGPQGAPGPAGEEGKRGARGEPGGVGPIGPPGERGAPGNRGFPGQDGLAGPKGAP

GERGPSGLAGPKGANGDPGRPGEPGLPGARGLTGRPGDAGPQGKVGPSGAPGEDGRPG
```

```
-continued
PPGPQGARGQPGVMGFPGPKGANGEPGKAGEKGLPGAPGLRGLPGKDGETGAAGPPGP

AGPAGERGEQGAPGPSGFQGLPGPPGPPGEGGKPGDQGVPGEAGAPGLVGPRGERGFP

GERGSPGAQGLQGPRGLPGTPGTDGPKGASGPAGPPGAQGPPGLQGMPGERGAAGIAG

PKGDRGDVGEKGPEGAPGKDGGRGLTGPIGPPGPAGANGEKGEVGPPGPAGSAGARGA

PGERGETGPPGPAGFAGPPGADGQPGAKGEQGEAGQKGDAGAPGPQGPSGAPGPQGPT

GVTGPKGARGAQGPPGATGFPGAAGRVGPPGSNGNPGPPGPPGPSGKDGPKGARGDSG

PPGRAGEPGLQGPAGPPGEKGEPGDDGPSGAEGPPGPQGLAGQRGIVGLPGQRGERGFP

GLPGPSGEPGKQGAPGASGDRGPPGPVGPPGLTGPAGEPGREGSPGADGPPGRDGAAGV

KGDRGETGAVGAPGAPGPPGSPGPAGPTGKQGDRGEAGAQGPMGPSGPAGARGIQGPQ

GPRGDKGEAGEPGERGLKGHRGFTGLQGLPGPPGPSGDQGASGPAGPSGPRGPPGPVGP

SGKDGANGIPGPIGPPGPRGRSGETGPAGPPGNPGPPGPPGPPGPGIDMSAFAGLGPREKG

PDPLQYMRA.
```

Differences between the amino acid sequences of α1 (II) M6 and α1 (II) are shown by amino acids in bold and gray background in FIG. 2.

A DNA sequence of a gene (denoted as COL2A1M6) encoding the α1 (II) M6 set forth in SEQ ID NO: 5 is set forth in SEQ ID NO: 6.

```
SEQ ID NO: 6:
CAAATGGCTGGTGGATTCGATGAAAAGGCTGGTGGAGCCCAATTAGGTCCTCC

ACAAGGTCCTCCCGGTCCACCTGGTCCTCCCGGTCCTCCAGGTCCCGCCGGTGCTCC

TGGACCACAGGGTTTCCAAGGAAACCCCGGTGAACCAGGTGAGCCTGGTGTTTCAG

GTCCTCCCGGTCCTCCAGGACCACCTGGACCACCAGGAAAGCCTGGTGACGACGGA

GAAGCTGGTAAACCAGGAAAGGCAGGAGAGAGAGGTCCACCTGGACCTCAGGGTG

CCAGAGGTTTCCCAGGTACCCCTGGTCTTCCTGGTGTCAAGGGTCATAGAGGTTACC

CCGGTTTGGATGGTGCCAAGGGTGAAGCCGGTGCCCCTGGTGTTAAGGGTGAATCA

GGAAGTCCCGGTGAAAATGGAAGTCCCGGTCCACCCGGTCCACCTGGACTGCCAGG

TGAGAGAGGAAGAACCGGACCAGCTGGTGCTGCAGGTGCTAGAGGAAATGACGGA

CAGCCCGGACCAGCCGGACCTCCCGGTCCTGTTGGGCCCGCAGGTGGTCCTGGTTTC

CCtgGTGCTCCTGGAGCCAAAGGAGAAGCCGGACCCACCGGAGCCAGAGGTCCCGA

GGGAGCACAGGGACCTAGAGGAGAACCAGGTACACCAGGTAGTCCCGGTCCTGCTG

GTGCATCAGGAAATCCCGGAACTGACGGTATTCCAGGAGCAAAGGGATCTGCAGGA

GCACCAGGAATAGCTGGTGCTCCTGGATTTCCAGGTCCCAGAGGACCTCCCGGTCCT

CAAGGAGCAACAGGTCCTTTGGGACCAAAAGGTCAAACAGGAGAACCAGGTATTGC

TGGATTCAAAGGAGAGCAAGGTCCAAAGGGAGAGCCCGGTCCCGCAGGTCCCCAAG

GAGCCCCAGGACCAGCTGGTGAAGAAGGAAAAAGAGGAGCCAGAGGTGAACCTGG

AGGAGTAGGACCTATTGGTCCTCCTGGTGAGAGAGGTGCTCCCGGAAACAGAGGTT

TTCCTGGTCAAGATGGTCTGGCTGGACCTAAAGGTGCTCCAGGAGAGAGAGGACCT

TCAGGACTTGCTGGTCCAAAAGGTGCTAACGGAGATCCAGGAAGACCCGGTGAACC

TGGTCTGCCTGGAGCTAGAGGATTAACAGGAAGACCAGGTGACGCAGGTCCCCAGG

GTAAAGTGGGTCCCAGTGGTGCCCCAGGTGAAGATGGAAGACCTGGTCCTCCCGGA

CCCCAAGGTGCAAGAGGTCAGCCTGGAGTGATGGGATTTCCTGGACCCAAGGGTGC

TAACGGAGAACCTGGAAAAGCTGGTGAGAAAGGACTGCCCGGTGCCCCAGGTCTTA

GAGGTTTGCCAGGTAAAGATGGAGAAACAGGAGCCGCAGGACCACCCGGTCCAGCC
```

-continued

```
GGACCAGCAGGAGAGAGAGGTGAACAAGGAGCACCTGGTCCAAGTGGTTTTCAGGG

TCTTCCAGGTCCCCCTGGTCCACCAGGAGAGGGAGGTAAACCAGGTGACCAAGGTG

TCCCTGGAGAAGCAGGTGCACCCGGTCTTGTGGGTCCAAGAGGTGAAAGAGGATTC

CCTGGTGAGAGAGGATCTCCCGGAGCCCAGGGACTTCAAGGTCCTAGAGGTCTGCC

AGGTACCCCTGGTACAGACGGACCAAAGGGAGCATCAGGACCCGCTGGACCTCCCG

GAGCCCAAGGTCCTCCAGGTTTACAAGGTATGCCTGGTGAAGAGGTGCTGCAGGT

ATAGCTGGACCAAAAGGAGACAGAGGTGACGTTGGTGAGAAGGGTCCCGAAGGAG

CCCCTGGAAAAGATGGTGGAAGAGGATTAACAGGTCCTATAGGACCACCCGGTCCA

GCCGGTGCTAATGGAGAAAAAGGAGAAGTAGGTCCTCCAGGTCCAGCAGGATCTGC

AGGTGCTAGAGGTGCCCCTGGAGAGAGAGGTGAAACAGGACCACCTGGTCCAGCTG

GTTTCGCTGGTCCCCCAGGAGCTGATGGACAGCCCGGTGCAAAAGGTGAACAAGGA

GAAGCCGGACAGAAGGGAGATGCTGGAGCCCCGGTCCACAAGGTCCCTCAGGAGC

ACCAGGTCCTCAAGGTCCAACTGGTGTGACCGGGCCAAAGGGTGCAAGAGGAGCAC

AGGGACCTCCAGGAGCAACAGGTTTCCCAGGAGCTGCTGGTAGAGTCGGTCCACCC

GGATCTAATGGTAACCCCGGACCACCAGGACCACCTGGACCATCTGGAAAGGATGG

ACCCAAAGGAGCAAGAGGAGATTCAGGACCACCCGGAAGAGCAGGAGAACCTGGA

TTACAGGGTCCCGCCGGTCCACCAGGAGAGAAAGGAGAGCCCGGAGATGATGGTCC

CTCAGGTGCAGAGGGACCCCCAGGACCCCAAGGTCTGGCAGGTCAAAGAGGTATAG

TGGGTCTTCCAGGTCAAAGAGGTGAAAGAGGATTTCCAGGACTTCCAGGTCCTTCAG

GTGAACCCGGTAAACAGGGAGCCCCCGGAGCCTCAGGTGACAGAGGTCCTCCAGGA

CCAGTAGGACCCCCAGGTTTAACCGGACCAGCAGGTGAGCCAGGAAGAGAAGGTTC

TCCTGGAGCCGATGGACCTCCAGGAAGAGACGGTGCAGCTGGTGTTAAGGGTGACA

GAGGTGAAACTGGAGCCGTAGGAGCCCCAGGTGCCCCCGGACCACCCGGATCACCC

GGACCTGCAGGTCCTACTGGTAAACAAGGAGATAGAGGAGAAGCCGGTGCCCAGGG

TCCTATGGGTCCTTCTGGTCCTGCAGGAGCAAGAGGTATACAAGGTCCACAGGGTCC

CAGAGGTGACAAGGGTGAAGCAGGAGAACCCGGTGAGAGAGGTCTGAAGGGTCAT

AGAGGATTCACCGGGTTACAGGGTTTGCCAGGACCCCCTGGACCAAGTGGTGACCA

GGGTGCATCCGGTCCAGCAGGTCCTTCTGGACCAAGAGGTCCTCCCGGTCCAGTTGG

TCCATCAGGTAAAGACGGAGCCAACGGTATCCCAGGTCCCATCGGTCCTCCAGGTCC

TAGAGGAAGAAGTGGAGAGACTGGTCCTGCTGGACCTCCTGGAAACCCTGGTCCTC

CAGGACCTCCAGGTCCTCCAGGTCCCGGAATAGATATGTCCGCTTTCGCTGGATTGG

GACCAAGAGAGAAAGGTCCTGACCCTCTTCAATATATGAGAGCA.
```

Two termini of the DNA sequence encoding the α1 (1) M1 were modified as follows: a DNA sequence encoding a Strep-Tag H tag was added to the amino terminus and a DNA sequence encoding a 6×His Tag was added to the carboxyl terminus; and α1 (1) M1 protein with the tags was finally obtained by expression, which has 1,071 amino acids in total and is set forth in SEQ ID NO: 7.

SEQ ID NO: 7:
WSHPQFEKQLSYGYDEKSTGGISVPGPMGPSGPRGLPGPPGAPGPQGFQGPPGEPG

EPGASGPPGPPGPPGPPGKNGDDGEAGKPGRPGERGPPGPQGARGLPGTAGLPGMKGH

-continued

RGFSGLDGAKGDAGPAGPKGEPGSPGENGAPGQPGPPGLPGERGRPGAPGPAGARGND

GATGAAGPPGPTGPAGPPGFPGAVGAKGEAGPQGPRGSEGPQGVRGEPGPPGPAGAAG

PAGNPGADGQPGAKGANGAPGIAGAPGFPGARGPSGPQGPGGPPGPKGNSGEPGAPGS

KGDTGAKGEPGPVGVQGPPGPAGEEGKRGARGEPGPTGLPGPPGERGGPGSRGFPGAD

GVAGPKGPAGERGSPGPAGPKGSPGEAGRPGEAGLPGAKGLTGSPGSPGPDGKTGPPGP

AGQDGRPGPPGPPGARGQAGVMGFPGPKGAAGEPGKAGERGVPGPPGAVGPAGKDGE

AGAQGPPGPAGPAGERGEQGPAGSPGFQGLPGPAGPPGEAGKPGEQGVPGDLGAPGPS

GARGERGFPGERGVQGPPGPAGPRGANGAPGNDGAKGDAGAPGAPGSQGAPGLQGMP

GERGAAGLPGPKGDRGDAGPKGADGSPGKDGVRGLTGPIGPPGPAGAPGDKGESGPSG

PAGPTGARGAPGDRGEPGPPGPAGFAGPPGADGQPGAKGEPGDAGAKGDAGPPGPAGP

AGPPGPIGNVGAPGAKGARGSAGPPGATGFPGAAGRVGPPGPSGNAGPPGPPGPAGKEG

GKGPRGETGPAGRPGEVGPPGPPGPAGEKGSPGADGPAGAPGTPGPQGIAGQRGVVGLP

GQRGERGFPGLPGPSGEPGKQGPSGASGERGPPGPMGPPGLAGPPGESGREGAPGAEGS

PGRDGSPGAKGDRGETGPAGPPGAPGAPGAPGPVGPAGKSGDRGETGPAGPAGPVGPV

GARGPAGPQGPRGDKGETGEQGDRGIKGHRGFSGLQGPPGPPGSPGEQGPSGASGPAGP

RGPPGSAGAPGKDGLNGLPGPIGPPGPRGRTGDAGPVGPPGPPGPPGPPGPPSAGFDFSFL

PQPPQEKAHDGGRYYRAHHHHHH.

After optimization design, a DNA sequence of a gene (denoted as COL1A1M1) encoding the amino acid sequence (α1 (I) M1) set forth in SEQ ID NO: 7 is set forth in SEQ ID NO: 8.

SEQ ID NO: 8:
TGGTCTCATCCACAATTTGAAAAGCAACTTAGTTATGGATACGATGAAAAATCC

ACAGGTGGAATCAGTGTTCCTGGACCTATGGGTCCATCAGGTCCAAGAGGTTTACCA

GGACCTCCAGGTGCCCCAGGTCCCCAGGGATTTCAAGGTCCACCAGGAGAGCCTGG

TGAGCCAGGAGCTTCTGGTCCACCTGGTCCCCCTGGACCACCTGGTCCTCCAGGAAA

GAATGGAGATGATGGTGAAGCTGGAAAACCTGGAAGACCTGGAGAAAGAGGACCA

CCAGGACCCCAGGGTGCCAGAGGACTGCCAGGTACCGCAGGTCTGCCTGGAATGAA

AGGTCATAGAGGATTTTCAGGATTAGACGGTGCAAAGGGAGACGCTGGACCTGCAG

GACCAAAGGGTGAGCCAGGAAGTCCAGGAGAGAATGGTGCACCAGGACAGCCAGG

TCCACCTGGACTGCCCGGTGAAAGAGGTAGACCCGGAGCACCAGGACCAGCAGGTG

CAAGAGGAAATGATGGAGCTACAGGTGCTGCAGGACCCCCAGGTCCAACAGGACCA

GCCGGTCCTCCCGGTTTCCCAGGTGCCGTTGGAGCAAAAGGTGAAGCTGGTCCACA

GGGTCCAAGAGGTTCTGAAGGTCCACAGGGAGTTAGAGGAGAACCAGGACCCCCTG

GACCAGCTGGTGCAGCAGGACCAGCTGGTAACCCTGGTGCTGACGGTCAGCCAGGT

GCTAAGGGAGCAAATGGAGCACCAGGAATAGCTGGTGCCCCAGGATTTCCCGGTGC

TAGAGGTCCAAGTGGTCCACAAGGACCAGGAGGTCCACCCGGTCCCAAAGGAAACA

GTGGAGAACCAGGTGCACCCGGTTCAAAGGGAGATACAGGAGCTAAAGGAGAGCC

CGGTCCAGTGGGTGTTCAGGGACCACCCGGACCTGCTGGAGAGGAAGGTAAAAGAG

GTGCAAGAGGTGAGCCAGGACCAACAGGTCTGCCTGGTCCCCCTGGTGAAAGAGGT

GGTCCAGGTAGTAGAGGATTTCCAGGAGCTGATGGTGTTGCAGGACCAAAGGGACC

-continued

```
CGCAGGTGAGAGAGGATCACCCGGTCCAGCCGGACCAAAAGGATCACCAGGAGAA
GCTGGTAGACCAGGAGAAGCTGGTCTGCCAGGTGCTAAAGGATTGACAGGATCACC
CGGTTCACCTGGTCCTGATGGAAAGACAGGACCTCCAGGTCCCGCTGGTCAGGACG
GTAGACCAGGACCCCCAGGACCCCCAGGTGCAAGAGGTCAGGCAGGTGTAATGGGT
TTCCCCGGACCTAAAGGAGCAGCTGGAGAACCTGGTAAAGCTGGAGAGAGAGGAGT
GCCTGGACCCCTGGAGCTGTTGGTCCAGCAGGAAAGGATGGTGAGGCAGGTGCAC
AAGGTCCACCTGGACCCGCTGGACCTGCAGGTGAGAGAGGAGAGCAAGGTCCCGCA
GGTTCTCCAGGTTTTCAGGGTTTGCCAGGTCCAGCCGGTCCTCCTGGAGAGGCAGGA
AAGCCAGGAGAACAAGGAGTTCCAGGAGACCTGGGTGCACCAGGACCCTCTGGTGC
AAGAGGAGAGAGAGGATTTCCTGGAGAAAGAGGTGTGCAGGGACCACCAGGTCCC
GCCGGTCCAAGAGGAGCAAATGGAGCCCCTGGAAATGACGGAGCTAAGGGTGACG
CTGGTGCACCAGGAGCACCAGGTTCTCAAGGTGCTCCCGGATTGCAGGGTATGCCTG
GAGAGAGAGGTGCAGCTGGACTGCCAGGTCCAAAAGGTGACAGAGGAGACGCCGG
TCCTAAGGGAGCTGACGGTTCTCCTGGAAAGGACGGTGTGAGAGGTTTGACAGGAC
CAATAGGTCCACCCGGTCCTGCTGGAGCCCCTGGAGACAAAGGTGAATCAGGTCCT
TCCGGTCCAGCCGGACCAACAGGAGCAAGAGGAGCACCTGGAGACAGAGGAGAGC
CAGGTCCTCCAGGACCTGCAGGTTTCGCTGGTCCTCCCGGAGCAGATGGACAGCCA
GGAGCTAAGGGAGAACCCGGTGACGCTGGTGCTAAGGGAGATGCAGGTCCACCAGG
TCCTGCTGGTCCTGCTGGACCTCCCGGACCAATAGGTAATGTTGGAGCACCCGGAGC
AAAAGGTGCCAGAGGTTCCGCAGGTCCTCCCGGAGCAACTGGTTTTCCAGGAGCTG
CCGGAAGAGTGGGTCCACCTGGTCCTTCTGGAAATGCAGGACCACCAGGTCCTCCTG
GTCCAGCCGGAAAGGAAGGTGGAAAGGGACCTAGAGGAGAAACAGGTCCCGCAGG
TAGACCCGGTGAGGTGGGTCCACCTGGTCCACCCGGTCCAGCTGGTGAGAAAGGAA
GTCCTGGAGCAGACGGACCAGCTGGTGCCCCTGGTACACCAGGACCCCAAGGAATA
GCTGGTCAAAGAGGTGTTGTTGGTTTACCAGGTCAGAGAGGAGAAAGAGGTTTTCC
AGGATTACCAGGTCCCTCAGGTGAGCCCGGAAAACAGGGTCCCTCAGGAGCAAGTG
GTGAAAGAGGACCACCAGGACCAATGGGACCTCCAGGATTAGCTGGTCCACCAGGA
GAATCAGGAAGAGAGGGTGCTCCTGGAGCAGAAGGTTCACCAGGAAGAGACGGTTC
ACCCGGAGCCAAGGGAGACAGAGGTGAAACAGGTCCCGCAGGTCCACCAGGAGCA
CCCGGAGCCCCTGGTGCTCCAGGACCTGTCGGACCAGCAGGAAAATCCGGTGACAG
AGGTGAGACTGGACCCGCAGGTCCTGCTGGTCCTGTTGGACCAGTGGGTGCAAGAG
GACCAGCAGGTCCACAAGGTCCAAGAGGTGACAAAGGTGAGACAGGTGAGCAGGG
TGACAGAGGAATTAAAGGTCACAGAGGATTTTCAGGACTGCAGGGACCACCCGGTC
CTCCCGGTTCCCCAGGAGAGCAAGGTCCATCCGGTGCATCCGGTCCAGCTGGACCCA
GAGGACCACCTGGTTCTGCTGGTGCACCAGGTAAAGATGGATTGAACGGTTTGCCTG
GTCCAATAGGACCTCCTGGTCCAAGAGGAAGAACTGGTGACGCCGGTCCCGTCGGA
CCACCCGGTCCACCAGGTCCCCCAGGTCCACCCGGACCACCATCCGCAGGATTTGAT
TTCTCATTCCTTCCTCAACCTCCTCAAGAGAAAGCACATGATGGAGGTAGATACTAT
AGAGCCCATCACCACCATCATCATTAA.
```

Two termini of the DNA sequence encoding the α1 (II) M6 were modified as follows: a DNA sequence encoding a Strep-Tag II tag was added to the amino terminus and a DNA sequence encoding a 6×His Tag was added to the carboxyl terminus; and α1 (II) M6 protein with the tags was finally obtained by expression, which has 1,076 amino acids in total and is set forth in SEQ ID NO: 9.

```
SEQ ID NO: 9:
EFWSHPQFEKQMAGGFDEKAGGAQLGPPQGPPGPPGPPGPPGPAGAPGPQGFQGN

PGEPGEPGVSGPPGPPGPPGPPGKPGDDGEAGKPGKAGERGPPGPQGARGFPGTPGLPG

VKGHRGYPGLDGAKGEAGAPGVKGESGSPGENGSPGPPGPPGLPGERGRTGPAGAAGA

RGNDGQPGPAGPPGPVGPAGGPGFPGAPGAKGEAGPTGARGPEGAQGPRGEPGTPGSP

GPAGASGNPGTDGIPGAKGSAGAPGIAGAPGFPGPRGPPGPQGATGPLGPKGQTGEPGIA

GFKGEQGPKGEPGPAGPQGAPGPAGEEGKRGARGEPGGVGPIGPPGERGAPGNRGFPG

QDGLAGPKGAPGERGPSGLAGPKGANGDPGRPGEPGLPGARGLTGRPGDAGPQGKVGP

SGAPGEDGRPGPPGPQGARGQPGVMGFPGPKGANGEPGKAGEKGLPGAPGLRGLPGKD

GETGAAGPPGPAGPAGERGEQGAPGPSGFQGLPGPPGPPGEGGKPGDQGVPGEAGAPG

LVGPRGERGFPGERGSPGAQGLQGPRGLPGTPGTDGPKGASGPAGPPGAQGPPGLQGM

PGERGAAGIAGPKGDRGDVGEKGPEGAPGKDGGRGLTGPIGPPGPAGANGEKGEVGPP

GPAGSAGARGAPGERGETGPPGPAGFAGPPGADGQPGAKGEQGEAGQKGDAGAPGPQ

GPSGAPGPQGPTGVTGPKGARGAQGPPGATGFPGAAGRVGPPGSNGNPGPPGPPGPSGK

DGPKGARGDSGPPGRAGEPGLQGPAGPPGEKGEPGDDGPSGAEGPPGPQGLAGQRGIV

GLPGQRGERGFPGLPGPSGEPGKQGAPGASGDRGPPGPVGPPGLTGPAGEPGREGSPGA

DGPPGRDGAAGVKGDRGETGAVGAPGAPGPPGSPGPAGPTGKQGDRGEAGAQGPMGP

SGPAGARGIQGPQGPRGDKGEAGEPGERGLKGHRGFTGLQGLPGPPGPSGDQGASGPA

GPSGPRGPPGPVGPSGKDGANGIPGPIGPPGPRGRSGETGPAGPPGNPGPPGPPGPPGPGI

DMSAFAGLGPREKGPDPLQYMRAHHHHHH.
```

After optimization design, a DNA sequence of a gene (denoted as COL2A1M6) encoding the amino acid sequence (α1 (II) M6) set forth in SEQ ID NO: 9 is set forth in SEQ ID NO: 10.

```
SEQ ID NO: 10:
GAATTCTGGAGTCATCCTCAATTCGAAAAACAAATGGCTGGTGGATTCGATGAA

AAGGCTGGTGGAGCCCAATTAGGTCCTCCACAAGGTCCTCCCGGTCCACCTGGTCCT

CCCGGTCCTCCAGGTCCCGCCGGTGCTCCTGGACCACAGGGTTTCCAAGGAAACCCC

GGTGAACCAGGTGAGCCTGGTGTTTCAGGTCCTCCCGGTCCTCCAGGACCACCTGGA

CCACCAGGAAAGCCTGGTGACGACGGAGAAGCTGGTAAACCAGGAAAGGCAGGAG

AGAGAGGTCCACCTGGACCTCAGGGTGCCAGAGGTTTCCCAGGTACCCCTGGTCTTC

CTGGTGTCAAGGGTCATAGAGGTTACCCCGGTTTGGATGGTGCCAAGGGTGAAGCC

GGTGCCCCTGGTGTTAAGGGTGAATCAGGAAGTCCCGGTGAAAATGGAAGTCCCGG

TCCACCCGGTCCACCTGGACTGCCAGGTGAGAGAGGAAGAACCGGACCAGCTGGTG

CTGCAGGTGCTAGAGGAAATGACGGACAGCCCGGACCAGCCGGACCTCCCGGTCCT

GTTGGGCCCGCAGGTGGTCCTGGTTTCCCtgGTGCTCCTGGAGCCAAAGGAGAAGCC

GGACCCACCGGAGCCAGAGGTCCCGAGGGAGCACAGGGACCTAGAGGAGAACCAG

GTACACCAGGTAGTCCCGGTCCTGCTGGTGCATCAGGAAATCCCGGAACTGACGGT

ATTCCAGGAGCAAAGGGATCTGCAGGAGCACCAGGAATAGCTGGTGCTCCTGGATT

TCCAGGTCCCAGAGGACCTCCCGGTCCTCAAGGAGCAACAGGTCCTTTGGGACCAA
```

-continued

```
AAGGTCAAACAGGAGAACCAGGTATTGCTGGATTCAAAGGAGAGCAAGGTCCAAA
GGGAGAGCCCGGTCCCGCAGGTCCCCAAGGAGCCCCAGGACCAGCTGGTGAAGAA
GGAAAAAGAGGAGCCAGAGGTGAACCTGGAGGAGTAGGACCTATTGGTCCTCCTGG
TGAGAGAGGTGCTCCCGGAAACAGAGGTTTTCCTGGTCAAGATGGTCTGGCTGGAC
CTAAAGGTGCTCCAGGAGAGAGAGGACCTTCAGGACTTGCTGGTCCAAAAGGTGCT
AACGGAGATCCAGGAAGACCCGGTGAACCTGGTCTGCCTGGAGCTAGAGGATTAAC
AGGAAGACCAGGTGACGCAGGTCCCCAGGGTAAAGTGGGTCCCAGTGGTGCCCCAG
GTGAAGATGGAAGACCTGGTCCTCCCGGACCCCAAGGTGCAAGAGGTCAGCCTGGA
GTGATGGGATTTCCTGGACCCAAGGGTGCTAACGGAGAACCTGGAAAAGCTGGTGA
GAAAGGACTGCCCGGTGCCCCAGGTCTTAGAGGTTTGCCAGGTAAAGATGGAGAAA
CAGGAGCCGCAGGACCACCCGGTCCAGCCGGACCAGCAGGAGAGAGAGGTGAACA
AGGAGCACCTGGTCCAAGTGGTTTTCAGGGTCTTCCAGGTCCCCCTGGTCCACCAGG
AGAGGGAGGTAAACCAGGTGACCAAGGTGTCCCTGGAGAAGCAGGTGCACCCGGTC
TTGTGGGTCCAAGAGGTGAAAGAGGATTCCCTGGTGAGAGAGGATCTCCCGGAGCC
CAGGGACTTCAAGGTCCTAGAGGTCTGCCAGGTACCCCTGGTACAGACGGACCAAA
GGGAGCATCAGGACCCGCTGGACCTCCCGGAGCCCAAGGTCCTCCAGGTTTACAAG
GTATGCCTGGTGAAAGAGGTGCTGCAGGTATAGCTGGACCAAAAGGAGACAGAGGT
GACGTTGGTGAGAAGGGTCCCGAAGGAGCCCCTGGAAAAGATGGTGGAAGAGGATT
AACAGGTCCTATAGGACCACCCGGTCCAGCCGGTGCTAATGGAGAAAAAGGAGAAG
TAGGTCCTCCAGGTCCAGCAGGATCTGCAGGTGCTAGAGGTGCCCCTGGAGAGAGA
GGTGAAACAGGACCACCTGGTCCAGCTGGTTTCGCTGGTCCCCCAGGAGCTGATGG
ACAGCCCGGTGCAAAAGGTGAACAAGGAGAAGCCGGACAGAAGGGAGATGCTGGA
GCCCCCGGTCCACAAGGTCCCTCAGGAGCACCAGGTCCTCAAGGTCCAACTGGTGT
GACCGGGCCAAAGGGTGCAAGAGGAGCACAGGGACCTCCAGGAGCAACAGGTTTC
CCAGGAGCTGCTGGTAGAGTCGGTCCACCCGGATCTAATGGTAACCCCGGACCACC
AGGACCACCTGGACCATCTGGAAAGGATGGACCCAAAGGAGCAAGAGGAGATTCA
GGACCACCCGGAAGAGCAGGAGAACCTGGATTACAGGGTCCCGCCGGTCCACCAGG
AGAGAAAGGAGAGCCCGGAGATGATGGTCCCTCAGGTGCAGAGGGACCCCCAGGA
CCCCAAGGTCTGGCAGGTCAAAGAGGTATAGTGGGTCTTCCAGGTCAAAGAGGTGA
AAGAGGATTTCCAGGACTTCCAGGTCCTTCAGGTGAACCCGGTAAACAGGGAGCCC
CCGGAGCCTCAGGTGACAGAGGTCCTCCAGGACCAGTAGGACCCCCAGGTTTAACC
GGACCAGCAGGTGAGCCAGGAAGAGAAGGTTCTCCTGGAGCCGATGGACCTCCAGG
AAGAGACGGTGCAGCTGGTGTTAAGGGTGACAGAGGTGAAACTGGAGCCGTAGGA
GCCCCAGGTGCCCCCGGACCACCCGGATCACCCGGACCTGCAGGTCCTACTGGTAA
ACAAGGAGATAGAGGAGAAGCCGGTGCCCAGGGTCCTATGGGTCCTTCTGGTCCTG
CAGGAGCAAGAGGTATACAAGGTCCACAGGGTCCCAGAGGTGACAAGGGTGAAGC
AGGAGAACCCGGTGAGAGAGGTCTGAAGGGTCATAGAGGATTCACCGGGTTACAGG
GTTTGCCAGGACCCCCTGGACCAAGTGGTGACCAGGGTGCATCCGGTCCAGCAGGT
CCTTCTGGACCAAGAGGTCCTCCCGGTCCAGTTGGTCCATCAGGTAAAGACGGAGCC
AACGGTATCCCAGGTCCCATCGGTCCTCCAGGTCCTAGAGGAAGAAGTGGAGAGAC
```

```
-continued
TGGTCCTGCTGGACCTCCTGGAAACCCTGGTCCTCCAGGACCTCCAGGTCCTCCAGG

TCCCGGAATAGATATGTCCGCTTTCGCTGGATTGGGACCAAGAGAGAAAGGTCCTG

ACCCTCTTCAATATATGAGAGCACACCATCACCATCATCACTAA.
```

The synthesis of DNA sequences was entrusted to Nanjing Genscript Biotechnology Co., Ltd. to synthesize DNA fragments of the genes set forth in SEQ ID NO: 8 and SEQ ID NO: 10.

Example 2 Construction of Recombinant Expression Vectors and Screening of Strains (1) Construction of Recombinant Expression Vectors Synthesized gene fragments set forth in SEQ ID NO: 8 and SEQ ID NO: 10 were recombined into a pPIC9K empty vector (purchased from Thermo Fisher Scientific) with a target fragment being accurately inserted into a secretion signal a factor-containing reading frame of a secretory vector to obtain a recombinant expression vector plasmid pPIC9K-COL2A1M6 expressing α1 (II) M6 and a recombinant expression vector plasmid pPIC9K-COL1A1M1 expressing α1 (I) M1.

Figure 4:
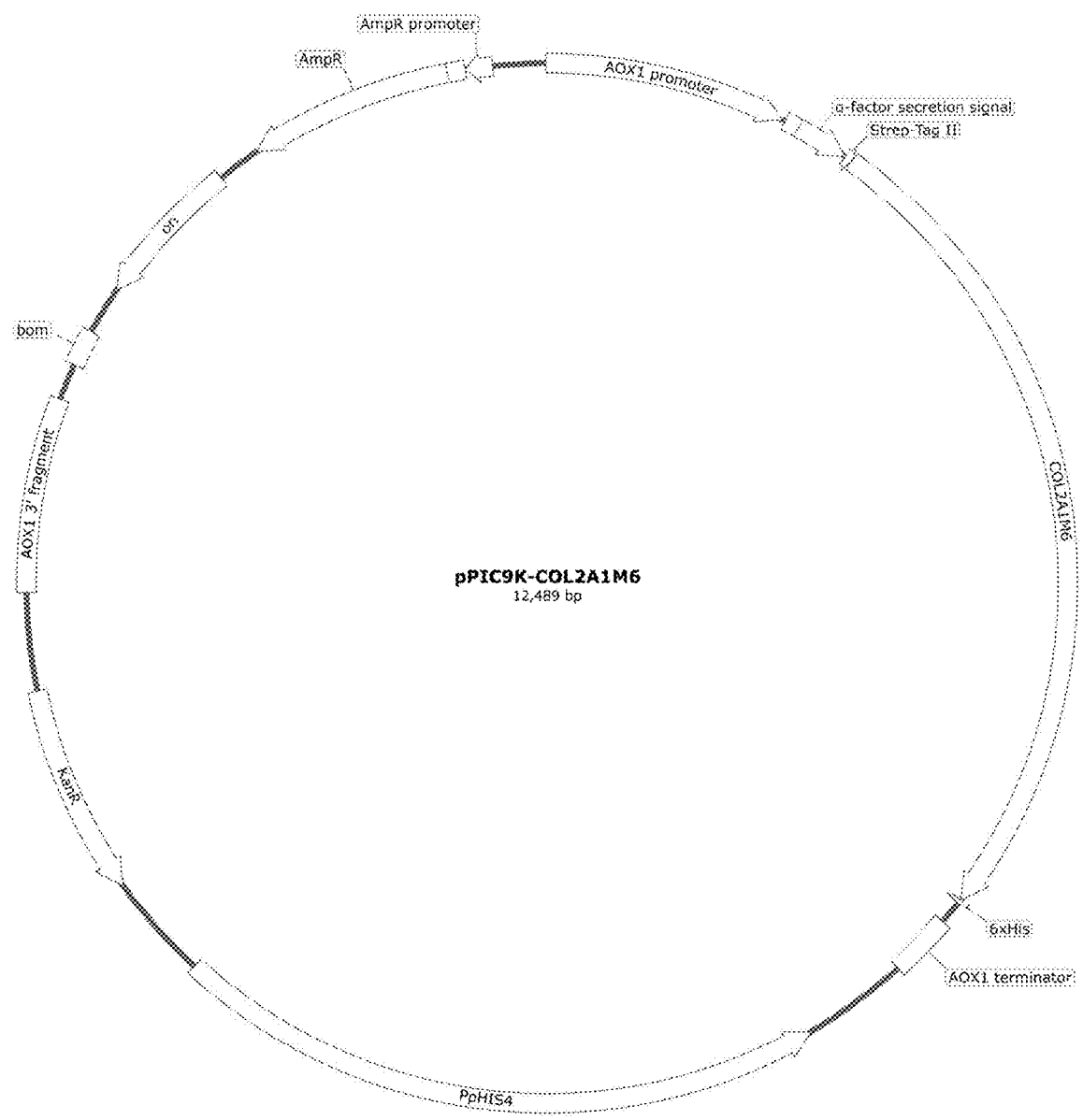
FIG. 4 is a map of a pPIC9K-COL2A1M6 vector.

The plasmids pPIC9K-COL2A1M6 and pPIC9K-COL1A1M1 were transformed into competent *Escherichia coli* DH5α (purchased from the Sangon Biotech (Shanghai) Co., Ltd.), positive clones were screened on an LB resistant plate with ampicillinum, and the recombinant plasmids were extracted for sequencing (which was entrusted to the Sangon Biotech (Shanghai) Co., Ltd.). Sequencing results showed that the recombinant plasmids were correct. Maps of the plasmids pPIC9K-COL1A1M1 and pPIC9K-COL2A1M6 are shown in FIG. 3 and FIG. 4, respectively.

(2) Screening of Strains

10 μg of the recombinant expression vector plasmids was digested overnight at 37° C. with SacI (SacI was purchased from the Dalian TaKaRa, and specific operations were performed according to instructions of a kit) for linearization, and then a PCR product purification kit (purchased from the Sangon Biotech (Shanghai) Co., Ltd.) was used to recover a linearized plasmid, with a volume controlled at about 10 μL.

The linearized plasmid was electrotransformed into a host *Pichia pastoris* SMD1168 (purchased from Thermo Fisher Scientific) competent cell, an electrotransformed *Pichia pastoris* solution was coated on MD plates with 100 μL to 200 μL for each plate, and the plates were allowed to stand at room temperature for 10 min and invertedly incubated at 30° C. for 2 d to 5 d until single colonies (positive transformants) appeared. 2 mL of sterile double-distilled water was added to a surface of each MD plate, then His' transformants on the surface of the plate were gently scraped off with a sterile triangular spreader, transferred to a 50 mL centrifuge tube, and diluted with sterile double-distilled water to obtain a suspension, $10^5$ cells were coated on a YPD plate including 0.5 mg/mL G418, and the plate was inverted and incubated at 30° C. for 3 d to 4 d until single colonies appeared. Colonies were picked from the YPD plate and added to a first sterile 96-well plate (200 μL of YPD/well), and a resulting mixture in each well was thoroughly mixed and incubated at 30° C. for 48 h to obtain a first cultivation system. The first cultivation system in each well of the first sterile 96-well plate was thoroughly mixed, and 10 μL of the first cultivation system was taken, added to a second sterile 96-well plate, and then incubated at 30° C. for 24 h to obtain a second cultivation system. The second cultivation system in each well of the second sterile 96-well plate was thoroughly mixed, and 10 μL of the second cultivation system was taken, added to a third sterile 96-well plate, and then incubated at 30° C. for 24 h to obtain a third cultivation system. 1 μL of the third cultivation system in the third sterile 96-well plate was taken, spotted on YPD plates with 1.0 mg/mL and 4 mg/mL G418, and further incubated at 30° C. for 96 h to 120 h. If *Pichia pastoris* transformants could grow on a plate with a high G418 concentration (4 mg/mL), it indicated that the transformants carried a plurality of copies of a target gene, that is, a plurality of recombinant fragments had entered *Pichia pastoris* and had been integrated into a chromosome of *Pichia pastoris* through homologous recombination. After the screening in this step, a recombinant engineered *Pichia pastoris* strain with a high copy number and a high expression level was obtained.

The two engineered strain samples respectively carrying pPIC9K-COL1A1M1 and pPIC9K-COL2A1M6 constructed were deposited in the China General Microbiological Culture Collection Center (CGMCC).

The engineered strain carrying the recombinant expression vector pPIC9K-COL1A1M1 could express the recombinant collagen α1 (I) M1, and was deposited in the China General Microbiological Culture Collection Center (CGMCC) located at NO. 1, West Beichen Road, Chaoyang District, Beijing, China on Mar. 11, 2021, with an accession number of CGMCC NO. 21891 and a taxonomic name of *Pichia pastoris*.

The engineered strain carrying the recombinant expression vector pPIC9K-COL2A1M6 could express the recombinant collagen α1 (II) M6, and was deposited in the China General Microbiological Culture Collection Center (CGMCC) located at NO. 1, West Beichen Road, Chaoyang District, Beijing, China on Mar. 11, 2021, with an accession number of CGMCC NO. 21892 and a taxonomic name of *Pichia pastoris*.

Example 3 Inducible Expression and Identification of Recombinant Collagen

The recombinant engineered strains expressing α1 (I) M1 and α1 (II) M6 obtained in Example 2 were taken, and an engineered *Pichia pastoris* strain expressing a full-length type I collagen α1 chain and an engineered *Pichia pastoris* strain expressing a full-length type II collagen α1 chain in the known patents were taken as controls. The two control engineered strains were the previous research results of the team of the inventors, and full-length collagen α1 chains expressed by the two control engineered strains also had a Strep-Tag II at an amino terminus and a 6×His Tag at a carboxyl terminus. The two control engineered strains were from the application No. 201911135958.0 (title: Yeast Recombinant Human Type I Collagen α1 Chain and Synthesis Method and Use thereof, an engineered *Pichia pastoris* strain expressing a full-length α1 (1) chain in this patent was deposited in the China General Microbiological Culture Collection Center (CGMCC), with an accession number of CGMCC NO. 17150) and the application No. 201911088025.0 (title: Method for Producing Recombinant Human Type H Collagen Single-Chain with *Pichia pastoris*, an engineered *Pichia pastoris* strain expressing a full-length α1 (II) chain in this patent was deposited in the China General Microbiological Culture Collection Center (CGMCC), with an accession number of CGMCC NO. 17149). The four engineered strains each were placed in a 100 mL erlenmeyer flask filled with 10 mL of a BMGY medium, and cultivated at 28° C. to 30° C. and 220 rpm until $OD_{600}$ was 2 to 6 (16 h to 18 h) to obtain a cultivation system. The cultivation system was centrifuged at 1,500 g to 3,000 g for 5 min at room temperature to obtain a precipitate, the precipitate was resuspended in a BMMY medium to obtain a suspension with $OD_{600}$ of about 2, and then the suspension was cultivated on a shaker at 28° C. to 30° C. and 220 rpm for 3 d, during which 100% methanol was added to the medium every 24 h to make a final concentration of methanol in the medium was 1.0%. After the induction with methanol was performed for 16 h or more, 1 mL of a strain solution sample was collected, placed in a 1.5 mL EP tube, and centrifuged at 12,000 g and 4° C. for 5 min to obtain an expression supernatant, and the expression supernatant was collected and stored at –80° C. for later use.

A 5× loading buffer (250 mM Tris-HCl, pH 6.8, 10% SDS, 0.5% bromophenol blue, 50% glycerin, and 5% β-mercaptoethanol) was added to the collected expression supernatant, and a resulting mixed solution was heated in a metal bath at 100° C. for 10 min and then tested by SDS-PAGE. Because the expressed target protein included a Srtep-Tag II at an amino terminus and a 6×His Tag at a carboxyl terminus, WB could be performed with an anti-Srtep-Tag II antibody and an anti-6×His Tag antibody (purchased from Nanjing Genscript Biotechnology Co., Ltd.) (specific operations could refer to instructions).

Figure 5:
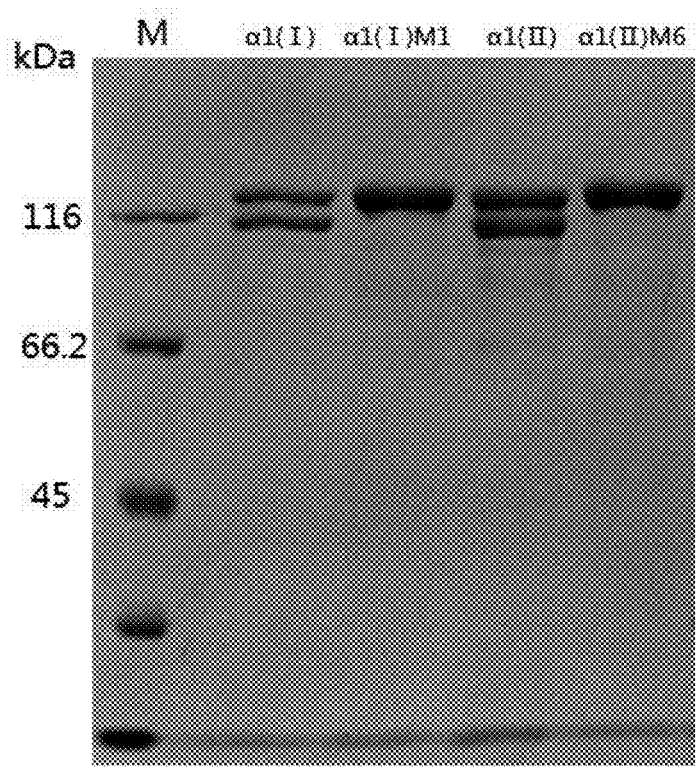
FIG. 5 shows an SDS-PAGE pattern of supernatants produced after inducible expression of α1 (I) M1 and α1 (II) M6 collagens for 24 h.

SDS-PAGE results of expression supernatants are shown in FIG. 5. α1 (I) M1, α1 (II) M6, α1 (I), and α1 (11) could be efficiently produced by secretory expression in an extracellular expression supernatant after 24 h of inducible expression. α1 (I) and α1 (II) each have a clear main degradation band (<116 kDa) below an expected target band (>116 kDa), while α1 (I) M1 and α1 (II) M6 of the present disclosure each merely have an expected target band (>116 kDa).

The measurement was performed with the Image Lab software (Bio-Rad Gel Doc XR+Imager), and measurement results were as follows.
  (1) An apparent molecular weight (116.3 kDa) of a target band of α1 (I) M1 was substantially consistent with an apparent molecular weight (116.4 kDa) of a target band of α1 (I), and an apparent molecular weight (118.2 kDa) of a target band of α1 (II) M6 was substantially consistent with an apparent molecular weight (118.1 kDa) of a target band of α1 (II). Apparent molecular weights of the target band of α1 (I) M1 and the target band of α1 (II) M6 were significantly larger than an apparent molecular weight of the main degradation band (104.5 kDa) of α1 (1) and an apparent molecular weight of the main degradation band (106.9 kDa) of α1 (II).
  (2) A ratio of a target band to a main degradation band in an electrophoresis result of α1 (I) was 51.5%: 48.3%, and a ratio of a target band to a main degradation band in an electrophoresis result of α1 (II) was 52.1%: 47.8%. The two ratios were substantially the same.

Figure 6A:
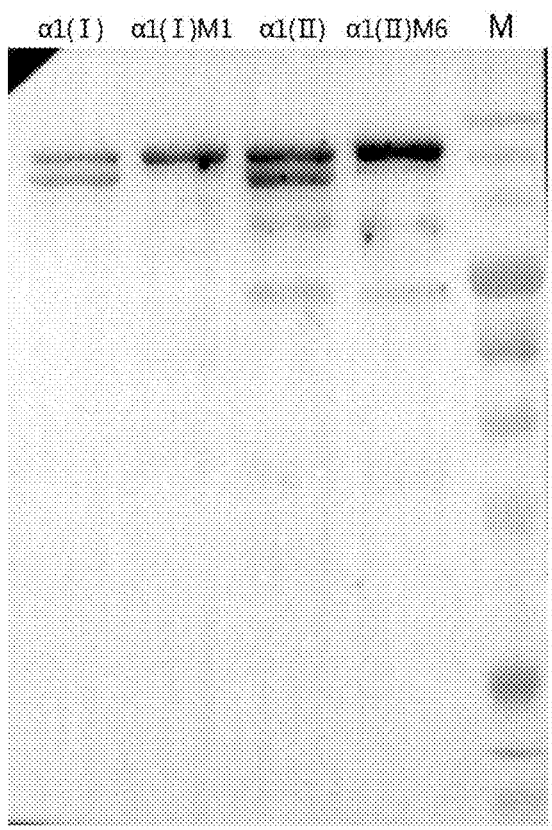
FIGS. 6A-6B show WB patterns of supernatants produced after inducible expression of α1 (I) M1 and α1 (II) M6 collagens for 24 h, where
Figure 6B:
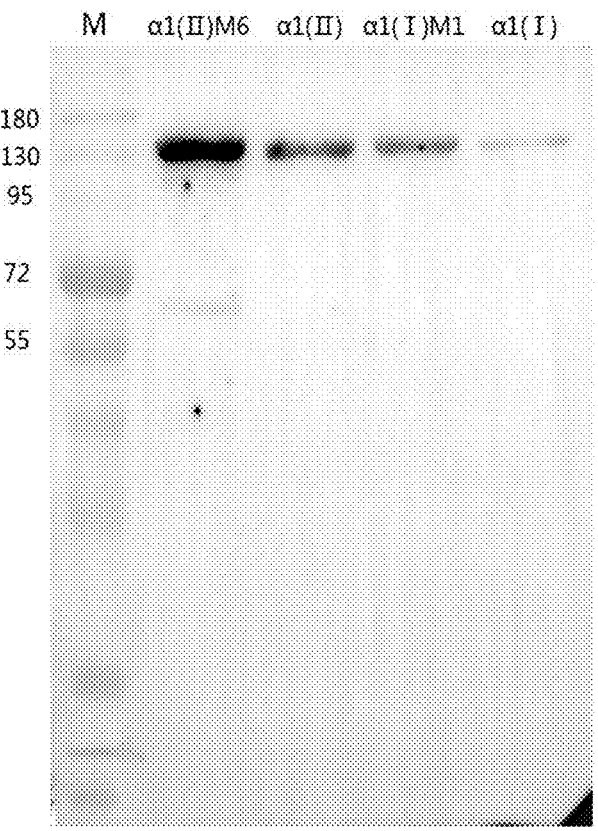
Figure 8B:
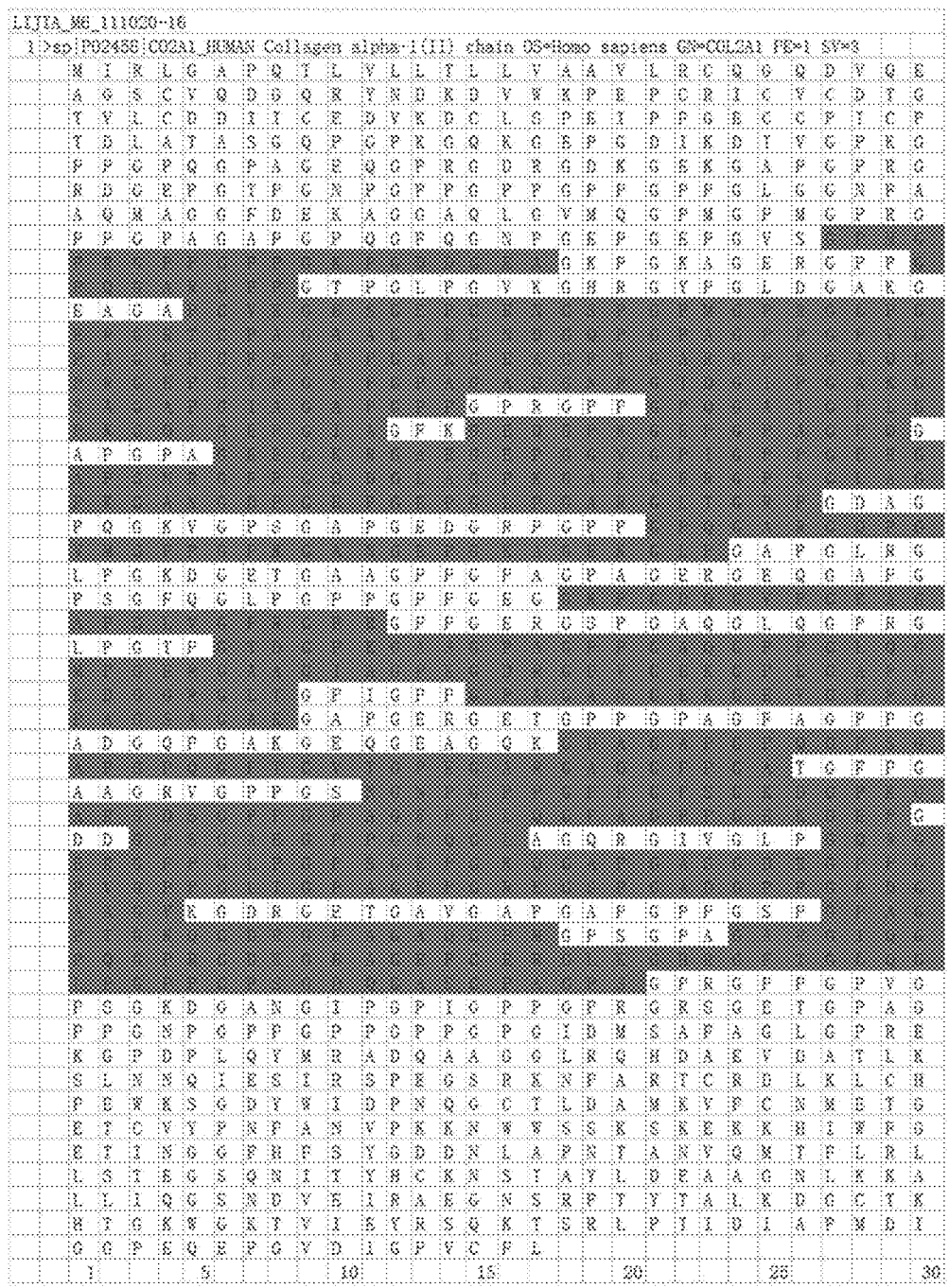
FIG. 8A (SEQ ID NO: 11) and FIG. 8B (SEQ ID NO: 12) show mass spectrometry results of target bands in SDS-PAGE results of α1 (I) M1 and α1 (II) M6 collagens.

It can be seen from enhanced chemiluminescence (ECL) color development results in FIGS. 6A-6B (a fully automatic chemiluminescence image analysis system Tanon 5200 integrates protein molecular weight markers into images) that the Srtep-Tag U tag at the amino terminus and the 6×His Tag at the carboxyl terminus both could be detected in the recombinant collagen α1 (1) M1 and α1 (II) M6, and target bands have the same apparent molecular weights as in SDS-PAGE, indicating that full-length sequences of the recombinant collagen α1 (I) M1 and α1 (II) M6 are successfully and efficiently produced by secretory expression and the expression of target bands is as expected. Although sequences of target bands of α1 (I) and α1 (II) collagens are full-length and complete, main degradation bands of α1 (I) and α1 (II) lack the amino-terminal sequence, and only the carboxyl-terminal 6×His Tag can be detected.

Target bands of α1 (I) M1 and α1 (II) M6 on an SDS-PAGE pattern, target bands of α1 (I) and al (II) on an SDS-PAGE pattern, and main degradation bands were cut off, subjected to enzymolysis with trypsin, and then tested by Nano-HPLC-MS/MS (which was entrusted to Suzhou ProtTech Inc.). Detected peptides were subjected to sequence alignment (Uniprot database), and data alignment results and alignment coverage maps of identified peptides with native sequences (parts with gray background, indicating parts of a peptide identified by mass spectrometry in a band that were identical to a native sequence) are shown in FIG. 7A-FIG. 7D and FIG. 8A-FIG. 8B. It could be found that:
  (1) Peptides detected after enzymolysis of target bands of α1 (I) M1 and α1 (I) and a main degradation band of α1 (I) all were sequences on a type I collagen α1 chain.
  (2) Peptides detected after enzymolysis of target bands of α1 (II) M6 and α1 (11) and a main degradation band of α1 (II) all were sequences on a type II collagen α1 chain.

The above results showed that α1 (I) M1 and α1 (II) M6 were expressed as successfully as α1 (T) and α1 (U), and were recombinant collagens of a human type I collagen α1 chain and a human type II collagen α1 chain, respectively, but α1 (1) and α1 (II) were degraded during expression, and main degradation bands of α1 (I) and α1 (II) also were collagens of respective types.

Example 4 High-Density Fermentation and Purification (1) High-Density Fermentation with Genetically Engineered Strains The recombinant collagen α1 (I) M1 and α1 (II) M6 were produced by expression on a large scale to obtain fermentation broths containing the recombinant collagen α1 (I) M1 and α1 (II) M6, respectively.

A seed medium YPG (yeast powder: 10 g/L, yeast peptone: 20 g/L, and anhydrous glycerin: 10 g/L); a fermentation medium ($NH_4H_2PO_4$: 190.4 g/L, $KH_2PO_4$: 10.06 g/L, $CaSO_4·2H_2O$: 1.18 g/L, $K_2SO_4$: 18.2 g/L, $MgSO_4·7H_2O$: 14.9 g/L, and glycerin: 40 g/L); a feed medium (including 50% W/V glycerin and 12 mL of PTM1 trace salts per liter); and an induction medium (including 100% methanol and 12 mL of PTM1 trace salts per liter) were adopted. The PTM1 was filtered through a 0.22 μm filter membrane for sterilization and stored at 4° C. The fermentation medium was sterilized at a high temperature and cooled to room temperature, then PTM1 was added to obtain a PTM1-containing fermentation medium, and the pH of the PTM1-containing fermentation medium was adjusted with ammonia water to 5.0.

Batch-cultivation and inducible expression of the constructed engineered strains were performed as follows.

The fed-batch cultivation was performed at 30° C.

The engineered strain was inoculated into a 1 L shake flask with the seed medium YPG, and cultivated at 220 rpm and 30° C. for 18 h to 20 h until $OD_{600}$ was 2 to 10.5 L fermentation tanks (Baoxing Biological Equipment Co., Ltd.) were used to be filled with 2 L of the fermentation medium containing 2% glycerin, and were sterilized separately. Before inoculation, a rotational speed was adjusted to 300 rpm, a ventilation rate was adjusted to 4 L/min, a temperature was adjusted to 30° C., and a pH was adjusted with an alkaline solution prepared from concentrated ammonia water to 4.5. 0.9 mL of PTM1 was added to the fermentation tank, and then 200 mL of a seed solution prepared was inoculated in the fermentation tank (flame ring inoculation). Then a dissolved oxygen electrode was clicked for hundred calibration, and fermentation was started. When the dissolved oxygen level fell to 30% for the first time, the dissolved oxygen level was kept at 30% by the dissolved oxygen/rotational speed cascade function. After glycerin was exhausted and the dissolved oxygen level rebounded to greater than 70% ($OD_{600}$ about 20), the dissolved oxygen/rotational speed cascade function was canceled, the stirring speed was increased to 650 rpm, and 80 mL of 30% glycerin was supplemented through linkage feeding. After the glycerin supplementation was completed and the dissolved oxygen level rebounded to 70% or more, the pH was set to 4 and the temperature was set to 29° C. to allow induced cultivation with a mixed carbon source of methanol and glycerin (methanol: 50% glycerin=7:3). 5 mL of the mixed carbon source was manually added. After the dissolved oxygen level rebounded to 70% or more, the feeding rate was set to 8 mL/h, then increased to 10 mL/h one hour later, and then further increased to 20 mL/h one hour later. When the dissolved oxygen level was lower than 30%, the feeding was stopped. After the dissolved oxygen level rebounded to 30%, linkage feeding was started. When a protein concentration measured by a UV method did not increase significantly or decreased after 40 h to 60 h of induction, a resulting fermentation broth was discharged. UV protein quantification formula: C (mg/mL)=$0.144*(A215-A225)$, $A215<1.5$. An engineered *Pichia pastoris* strain expressing a full-length α1 (I) chain (which was deposited in the China General Microbiological Culture Collection Center (CGMCC), with an accession number of CGMCC NO. 17150) and an engineered *Pichia pastoris* strain expressing a full-length α1 (II) chain (which was deposited in the China General Microbiological Culture Collection Center (CGMCC), with an accession number of CGMCC NO. 17149) each were used for high-density fermentation.

Figure 9A:
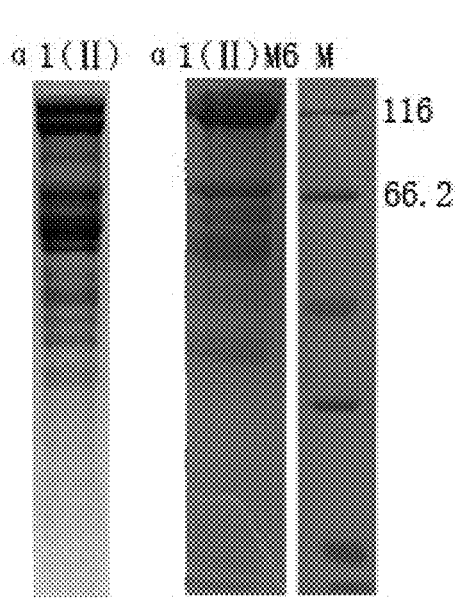
FIGS. 9A-9B show SDS-PAGE patterns of fermentation supernatants produced after inducible expression of α1 (I) M1, α1 (II) M6, α1 (1), and α1(II) collagens for 48 h.
Figure 9B:
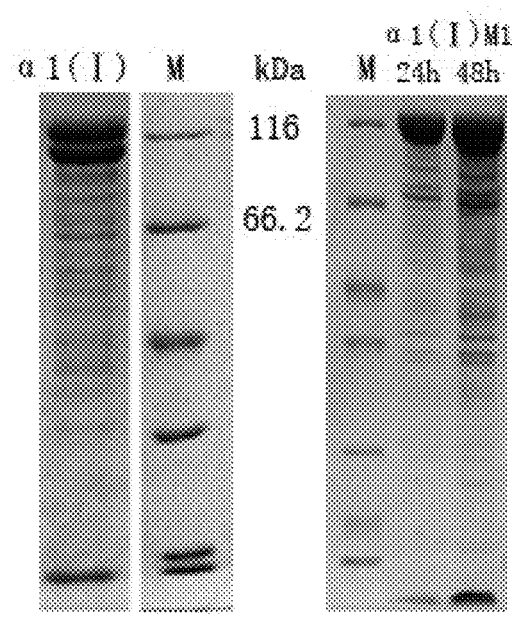

Results were shown in Table 1. After 48 h of induction, there was no significant difference between α1 (I) and α1 (I) M1 and between α1 (II) M6 and α1 (II) in terms of a strain concentration ($OD_{600}$), a strain wet weight, and a UV-quantified protein concentration expressed in a fermentation broth. Fermentation supernatants were collected and tested by SDS-PAGE, and test results are shown in FIGS. 9A-9B. Under high-density fermentation conditions, main degradation bands of α1 (I) and α1 (TI) were extremely obvious, which had no difference from the inducible expression in shake flasks. Main products of α1 (I) M1 and α1 (II) M6 were still target bands, and no main degradation band occurred, indicating that effects of α1 (I) M1 and α1 (II) M6 for eliminating main degradation bands (main degradation products) could still be effectively maintained under the high-density fermentation conditions.

TABLE 1

Strain concentrations, strain wet weights, and protein expression levels (UV quantification) in fermentation pilot experiments

| Type | $OD_{600}$ | Strain wet weight (g/L) | Protein (UV, g/L) |
|---|---|---|---|
| α1(II) | 189.0 | 260.0 | 17.8 |
| α1(II)M6 | 198.0 | 265.0 | 18.7 |
| α1(I) | 215.0 | 310.0 | 18.1 |
| α1(I)M1 | 201.0 | 301.0 | 17.3 |

(2) Collagen Purification

Buffer A: 20 mM $KH_2PO_4$, pH 4.0; and buffer B: 20 mM $KH_2PO_4$, 0.5 M NaCl, pH 4.0.

Figures 10A, 10B:
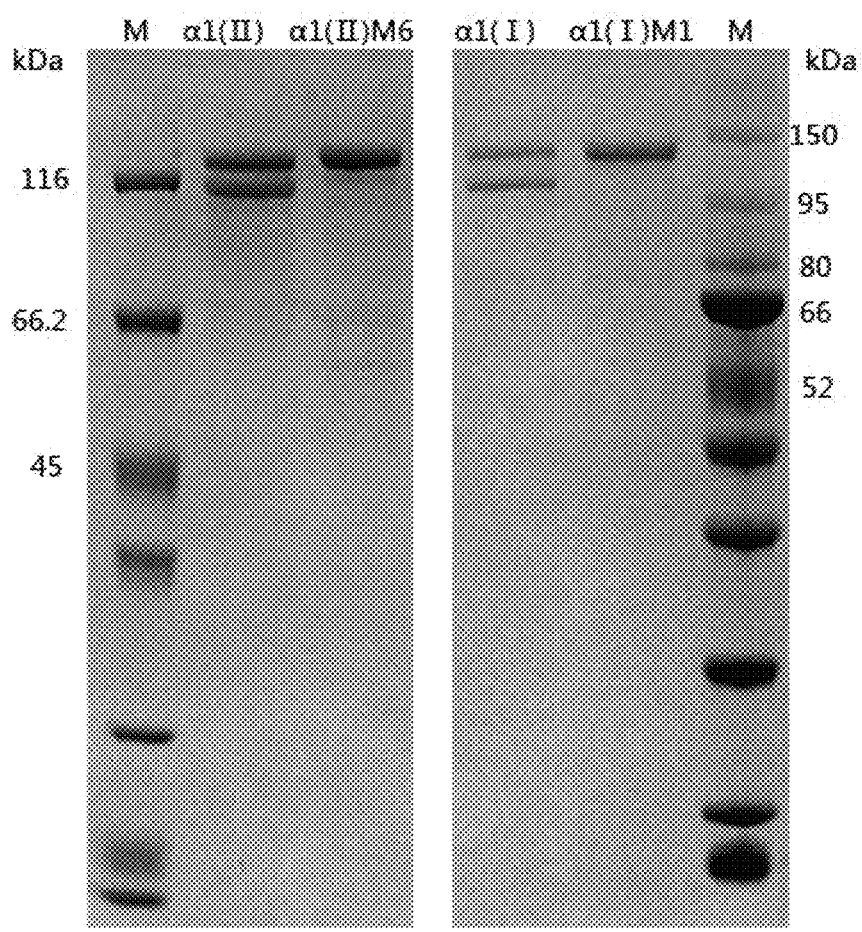
FIGS. 10A-10B show SDS-PAGE patterns of purified and lyophilized α1 (I) M1, α1 (II) M6, α1 (I), and α1 (II) sponges.
Figure 11A:
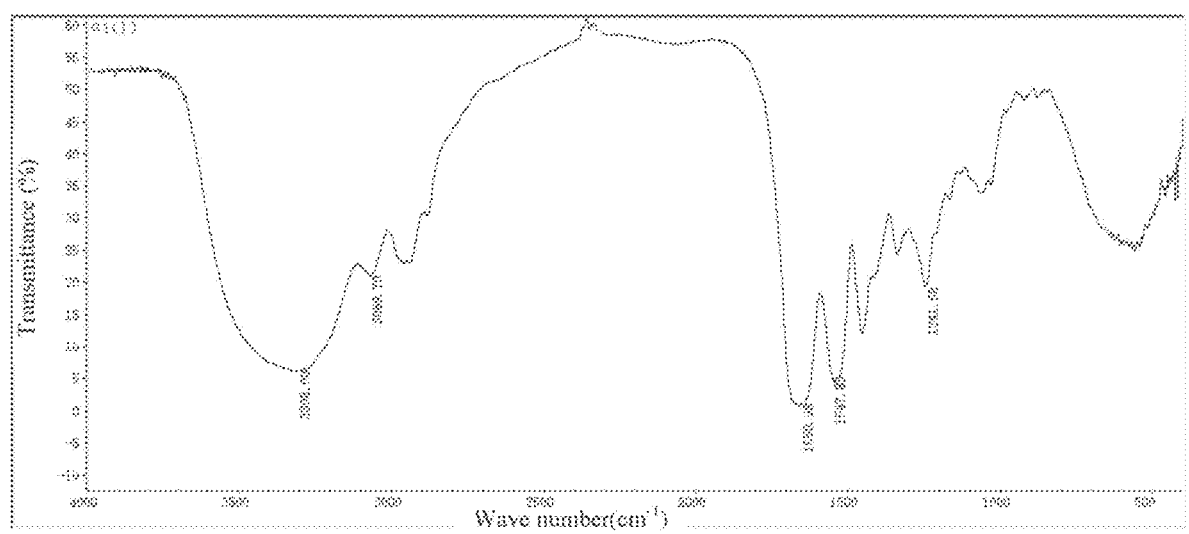
FIG. 11A and FIG. 11B show Fourier transform infrared (FT-IR) spectroscopy results of α1 (1) and α1 (II) collagens.
Figure 11B:
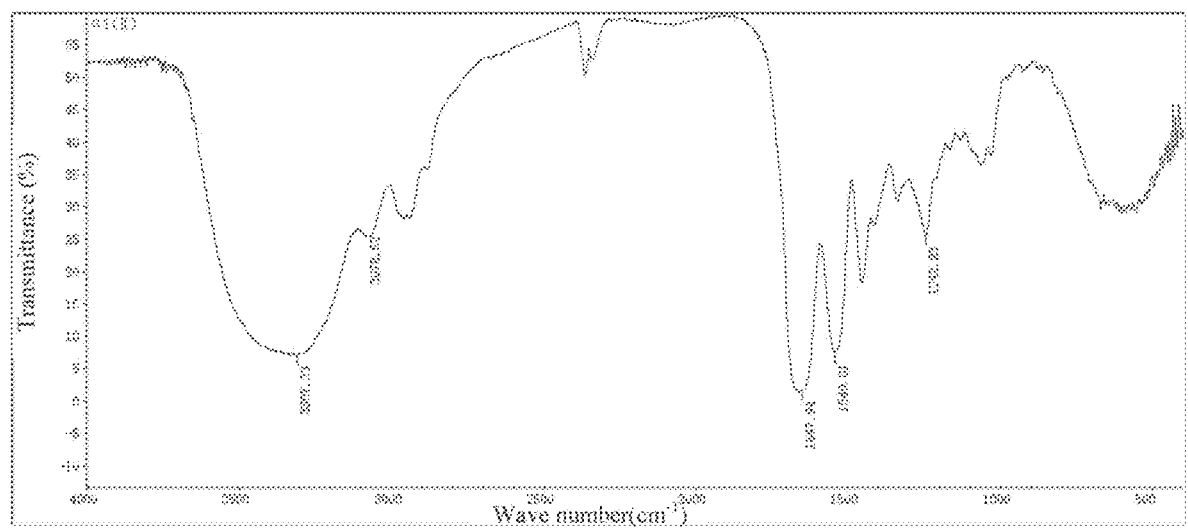
Figure 12A:
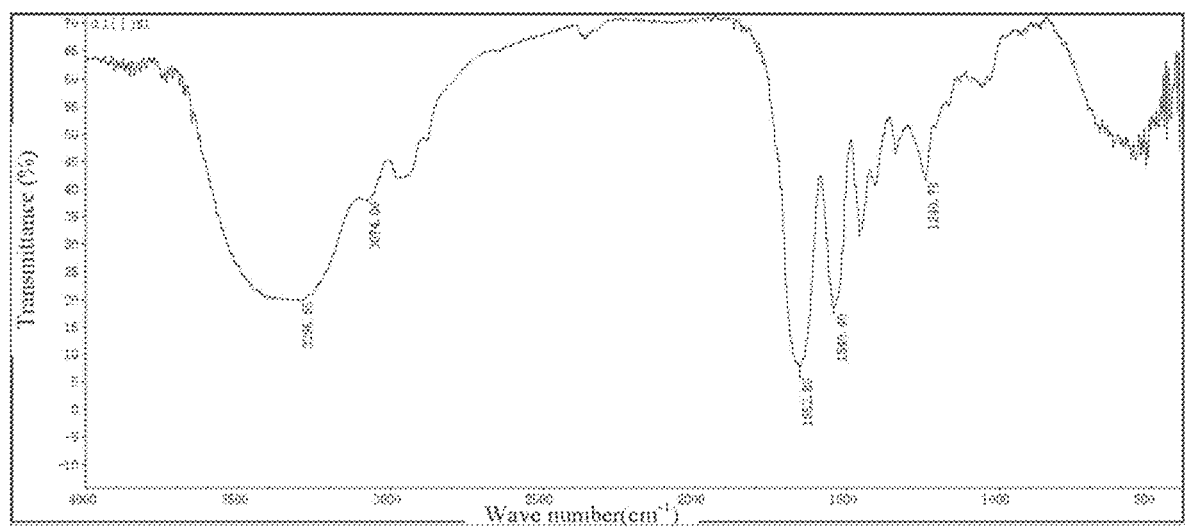
FIG. 12A and FIG. 12B show FT-IR spectroscopy results of α1 (I) M1 and α1 (II) M6 collagens.
Figure 12B:
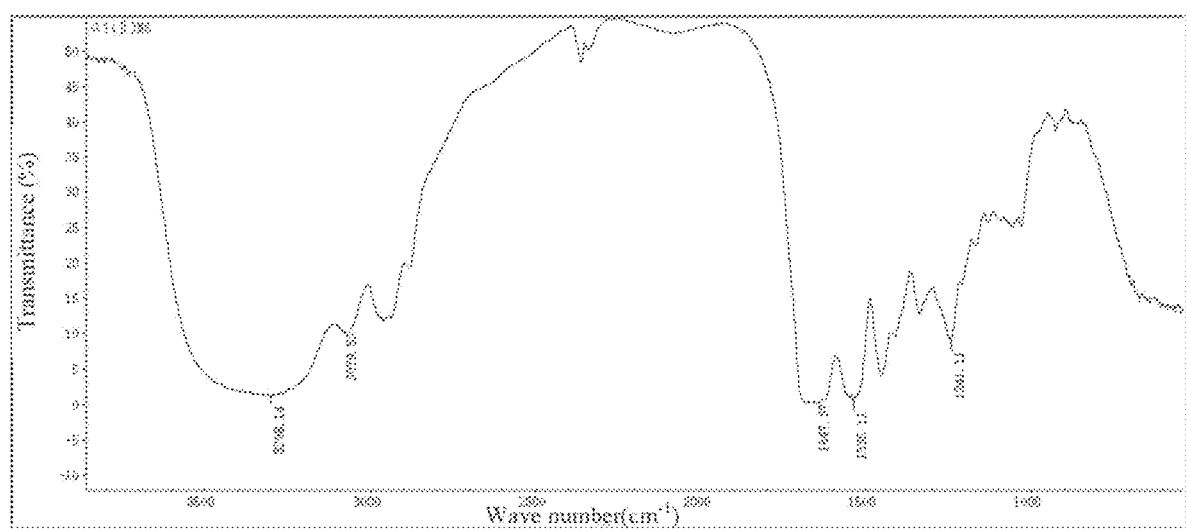

A fermentation broth was collected and centrifuged at 2,000 g and 4° C. for 30 min to obtain a strain precipitate and a fermentation supernatant. A cation exchange medium (a chromatography packing was UniGel-80sp produced by Suzhou Nanomicro Technology Co., Ltd., the chromatography packing was loaded on a GCC-50-400 chromatography column produced by the Lisure Science, and a GE AKTA Pure Protein Separation Chromatography Purification System was adopted) was equilibrated with the buffer A until an A215 absorbance value and a conductivity value remained unchanged, and then a sample was loaded at a flow rate of 40 us/cm and a volume of 0.5 L/time. The UV A215 absorbance was detected, and when it increased, the collection of an effluent was started. When the sample loading was completed, the collection of an effluent was stopped, and then the cation exchange medium was equilibrated with the buffer A. When the A215 absorbance decreased, the collection of an effluent was started until the UV absorbance and conductivity dropped to minimum values and no longer changed. An eluate was collected, tested to determine a composition, and then subjected to dialysis (with ultrapure water as a dialysis solution), concentration, and lyophilization to obtain a lyophilized collagen sponge, and the lyophilized collagen sponge was collected, dissolved in ultrapure water, and subjected to SDS-PAGE. Results are shown in FIGS. 10A-10B. After one-step ion exchange purification of α1 (I) M1 and α1 (II) M6, most of heteroproteins and small degradation bands were removed, and single target proteins with high purities were obtained (according to measurement results of the Image Lab software, a purity of α1 (1) M1 was 90.1% and a purity of α1 (II) M6 was 88.3%). However, after the same purification step of α1 (I) and a1 (II), a main degradation band still appeared and could not be eliminated, and a main degradation product had a similar size and very similar properties to a target product, such that the main degradation product and the target product could hardly be separated through one-step purification. According to the content in the applications No. 201911135958.0 and No. 201911088025.0, in order to obtain single target full-length α1 (I) and α1 (I) chain products, tandem affinity purification needed to be performed with Ni-NTA and Strep-Tactin affinity chromatography media based on the fact that a full-length α1 (I) chain and a full-length α1 (II) chain had a Srtep-Tag U at an amino terminus and a 6×His Tag at a carboxyl terminus. In this case, a main degradation product presented as a main degradation band during SDS-PAGE was discarded, which caused a waste of a biosynthetic resource of a strain, increased purification steps, and reduced a yield of a target product.

Example 5 Detection of Recombinant Collagens (1) FT-IR Spectroscopy

A trace amount of each of the purified and lyophilized α1 (I) M1, α1 (II) M6, α1 (I), and α1 (I) collagen samples was taken for test, mixed with potassium bromide (KBr), ground into a powder, then pressed into a tablet, and scanned in a range of 4,000 cm$^{-1}$ to 400 cm$^{-1}$ at room temperature (Thermo Scientific, Nicolet™ iS™ 10 FT-IR Spectrometer). The method and result analysis could be found in the literature (Jeong, H., J. Venkatesan and S. Kim, Isolation and characterization of collagen from marine fish (Thunnus obesus). Biotechnology and Bioprocess Engineering, 2013. 18 (6): p. 1185-1191.).

Infrared (IR) spectra of the purified α1 (1) M1, α1 (II) M6, α1 (I), and α1 (II) protein samples are shown in FIG. 11A-FIG. 11B and FIG. 12A-FIG. 12B. It can be seen that characteristic absorption average wave numbers of α1 (I) M1, α1 (II) M6, α1 (I), and α1 (I) all were in line with structural characteristics of recombinant collagen: an amide A (about 3,299 cm$^{-1}$), an amide B (about 3,081 cm$^{-1}$), an amide I (about 1,650 cm$^{-1}$), an amide II (about 1,530 cm$^{-1}$ to 1,550 cm$^{-1}$), and an amide III (about 1,240 cm$^{-1}$), indicating that amino acid mutations in α1 (I) M1 and α1 (II) M6 did not affect the properties of collagen itself (as shown in literatures [1]. Chen Jingtao et al., Infrared Spectroscopy of Recombinant Collagen and Bovine Type I Collagen. Materials Reports, 2008 (03): p. 119-121; [2]. Doyle, B. B., E. G. Bendit and E. R. Blout, Infrared spectroscopy of collagen and collagen-like polypeptides. Biopolymers, 1975. 14 (5): p. 937-957; and [3]. Zhou Aimei et al., Isolation, Purification, and Structural Characterization of Recombinant Human Collagen. Food and Fermentation Industries, 2015 (03): p. 46-52.).

(2) Detection of a Cell Adhesion Activity of Recombinant Collagens

A method for detecting a cell adhesion activity of recombinant collagen could be found in the literature: Juming Yao, Satoshi Yanagisawa, Tetsuo Asakura. Design, Expression and Characterization of Collagen-Like Proteins Based on the Cell Adhesive and Crosslinking Sequences Derived from Native Collagens, J Biochem. 136, 643-649 (2004). The detection of a cell adhesion activity was entrusted to the Functional Nanomaterials and Biomedical Testing Laboratory of School of Pharmacy, Changzhou University.

A specific implementation method was as follows: NIH/3T3 cells purchased from the Cell Bank of the Chinese Academy of Sciences (Product No. GNM6, the cultivation and passage methods were performed according to instructions of the cells) were cultivated normally. Lyophilized α1 (I) M1, α1 (II) M6, α1 (1), and α1 (II) recombinant collagen sponges, control human collagen (purchased from Sigma, Product No. C7774), and bovine serum albumin (BSA, purchased from Sangon Biotech (Shanghai) Co., Ltd.) each were taken and dissolved with ultrapure water or a 1 M HCl solution, then a protein concentration was determined according to a UV protein quantification empirical formula of C (mg/mL)=0.144×(A215−A225), and resulting solutions each were diluted with phosphate buffered saline (PBS) (pH 7.4) to 0.5 mg/mL. 100 μL of each of protein solutions and a blank PBS solution was added to a 96-well cell culture plate, and the plate was allowed to stand for 60 min at room temperature. Then NIH/3T3 cells in a well growth state were added at $10^5$ cells/well, and cultivated at 37° C. and 5% CO2 for 60 min. Cells in each well were washed with PBS 4 times. An LDH detection kit (Roche, 04744926001) was used to detect the absorbance $OD_{492\ nm}$ (specific operations were performed with reference to instructions).

Figure 13:
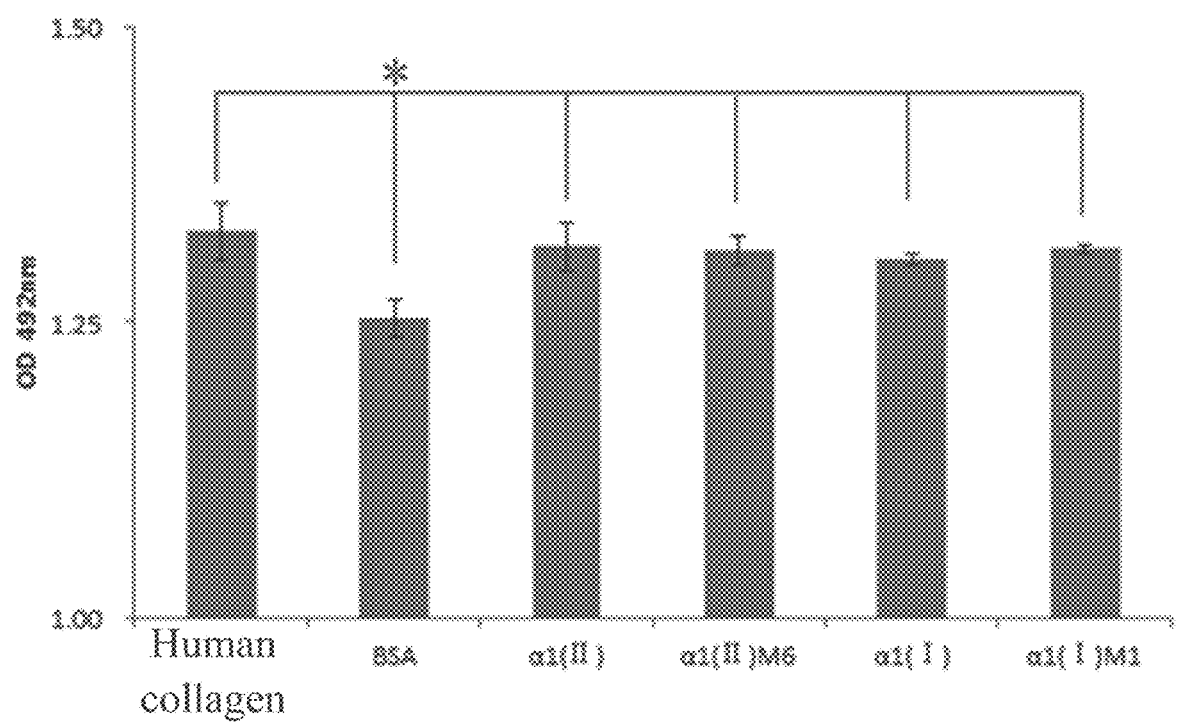
FIG. 13 shows cell adhesion activity results of α1 (I) M1, α1 (II) M6, α1 (I), and α1 (II) collagens.
Figure 14A:
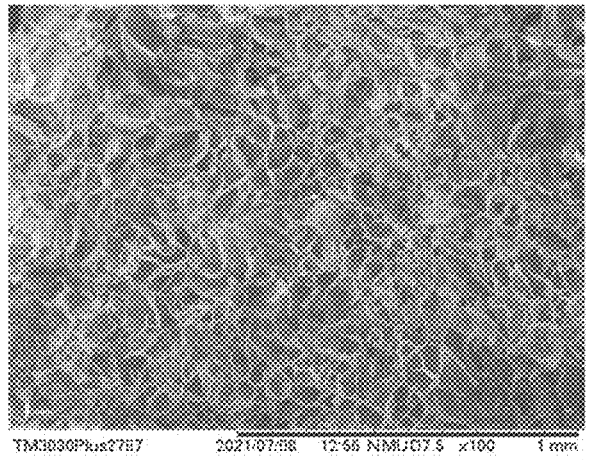
FIGS. 14A-14D show SEM images of surfaces of lyophilized α1 (I) and α1 (I) M1 collagen hydrogels (FIGS. 14A-14B show the α1 (I) collagen hydrogel and FIGS. 14C-14D show the α1 (I) M1 collagen hydrogel).
Figure 14B:
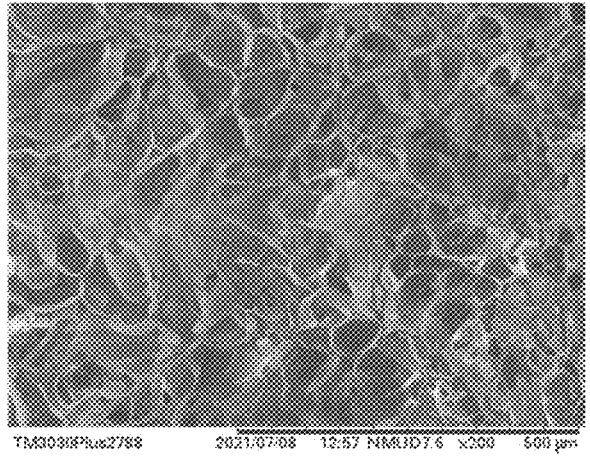
Figure 14C:
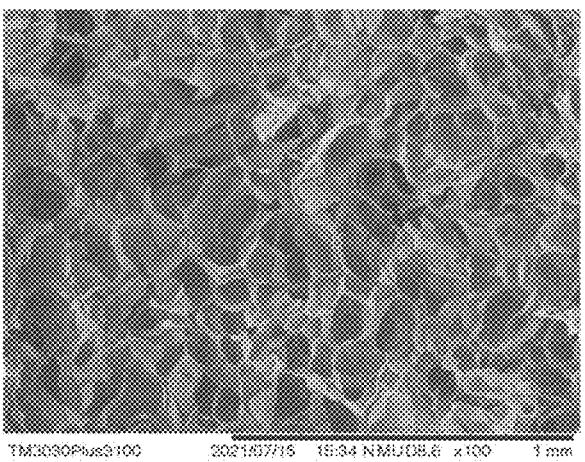
Figure 14D:
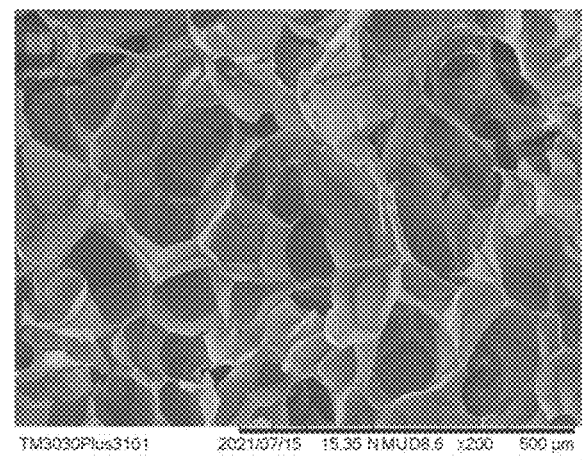
Figure 15A:
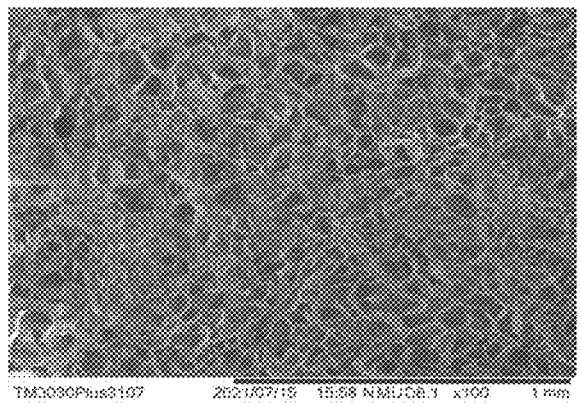
FIGS. 15A-15D show SEM images of surfaces of lyophilized α1 (I) and α1 (II) M6 collagen hydrogels (FIGS. 15A-15B show the α1 (II) collagen hydrogel and FIGS. 15C-15D show the α1 (II) M6 collagen hydrogel).
Figure 15B:
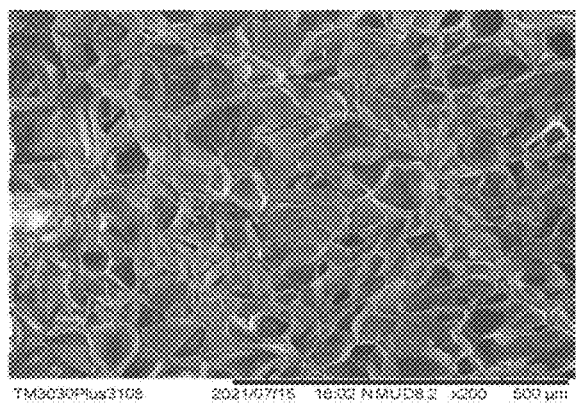
Figure 15C:
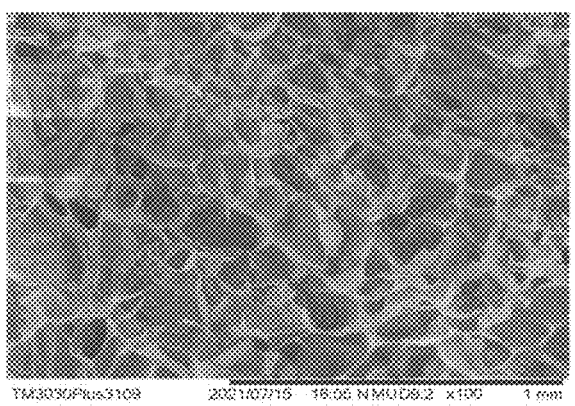
Figure 15D:
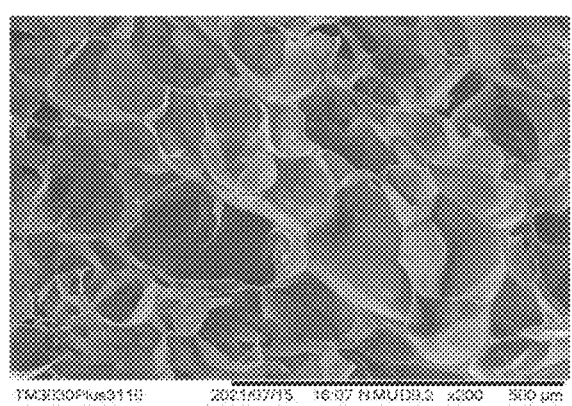
Figure 16A:
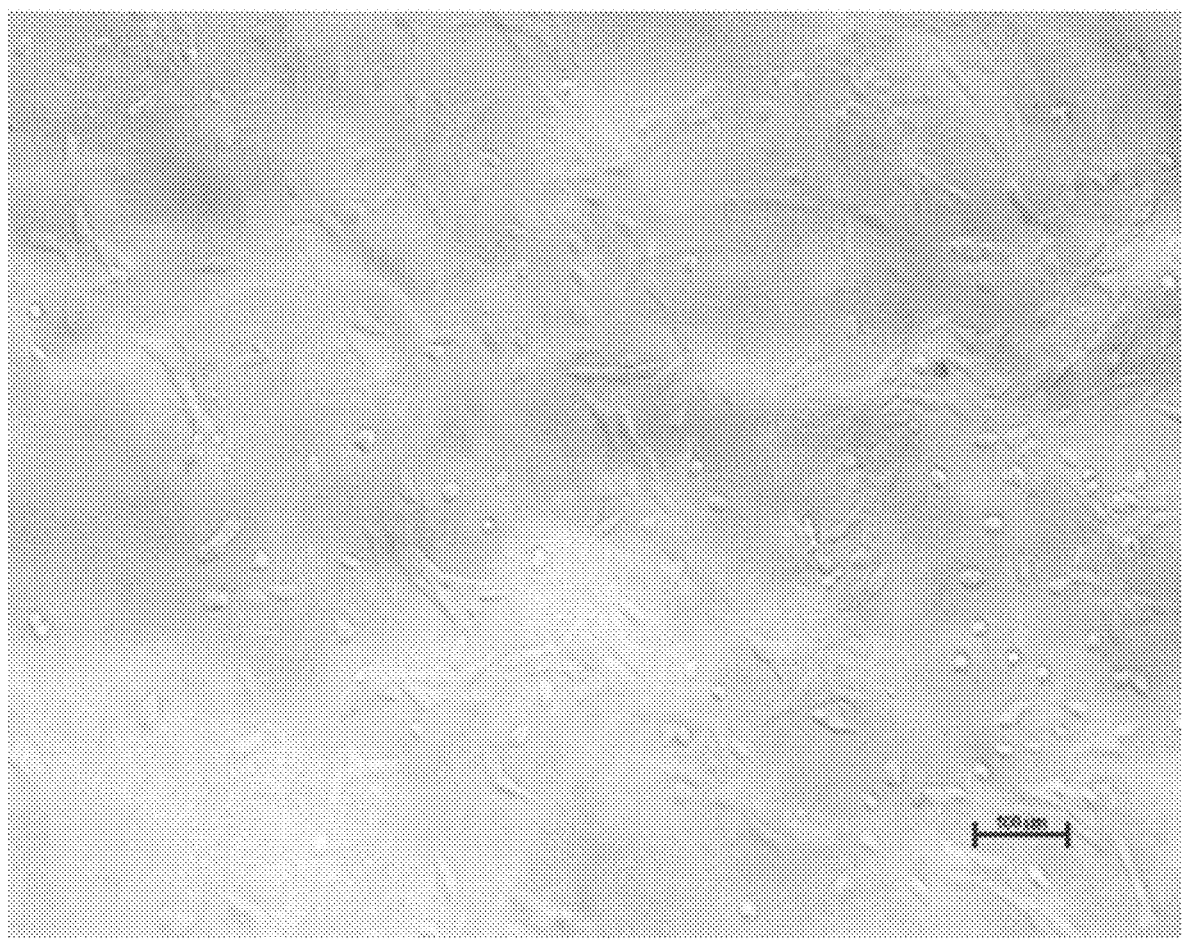
FIGS. 16A-16F show results of adherent growth of NIH/3T3 cells in α1 (I) and α1 (I) M1 collagen hydrogels, where
Figure 16B:
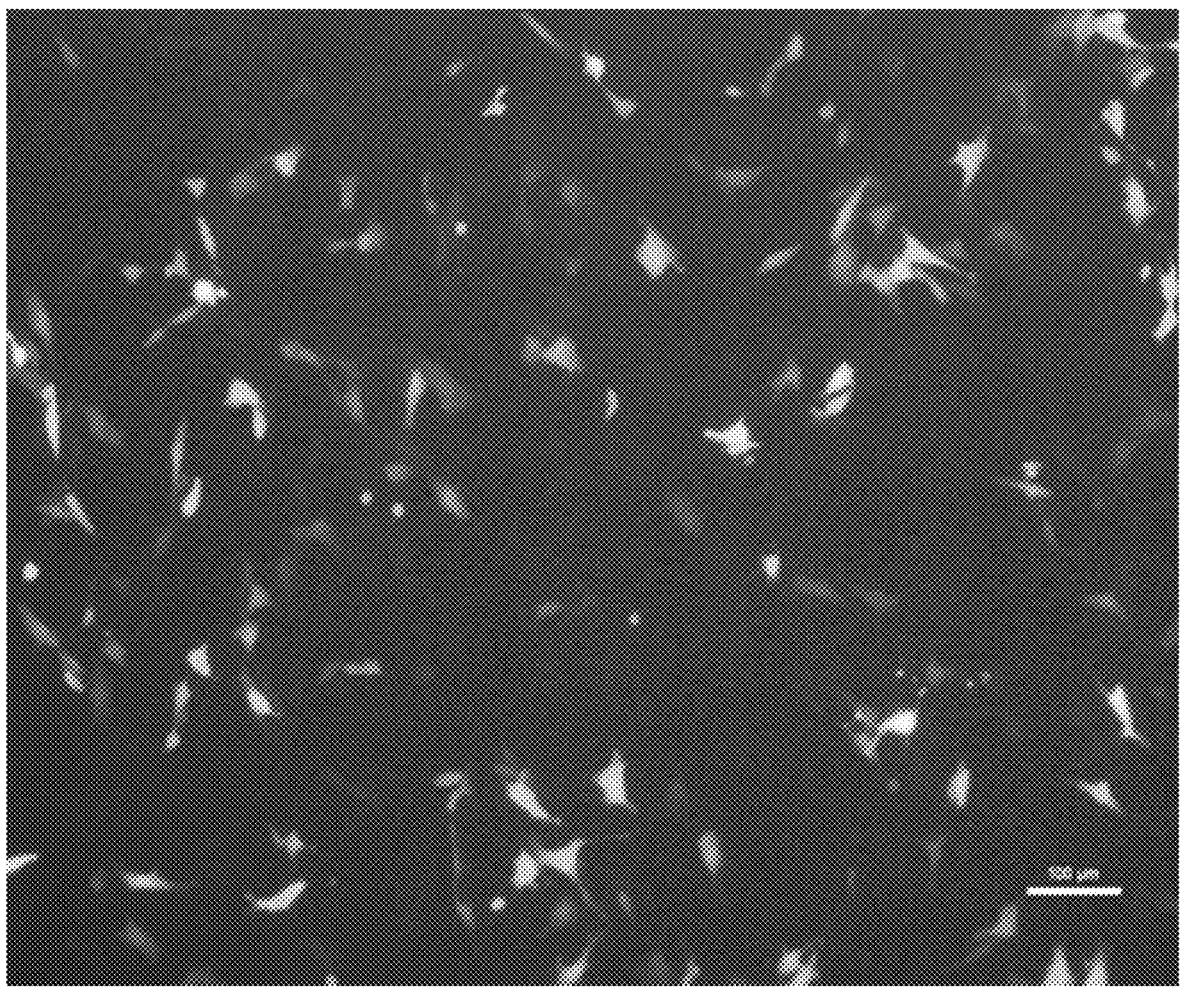
Figure 16C:
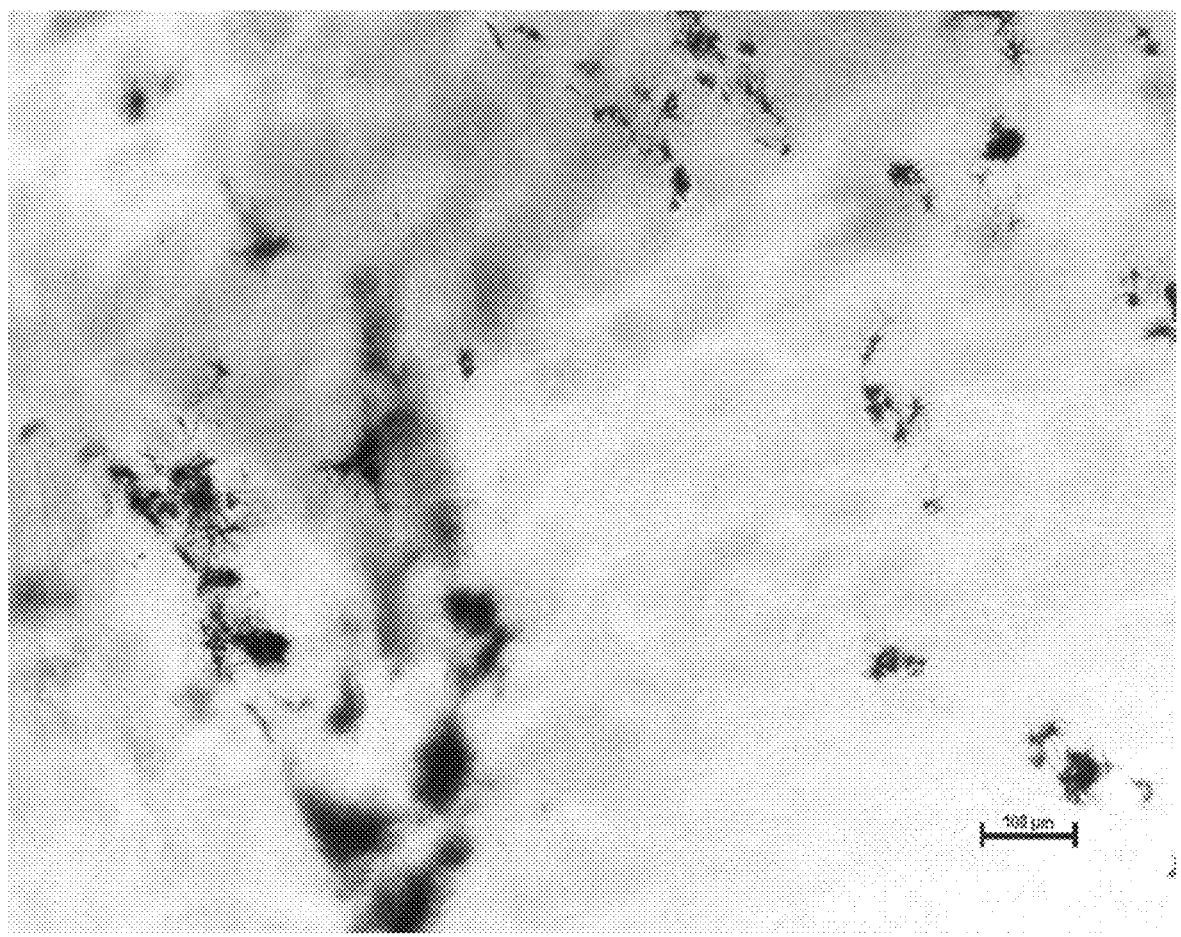
Figure 16D:
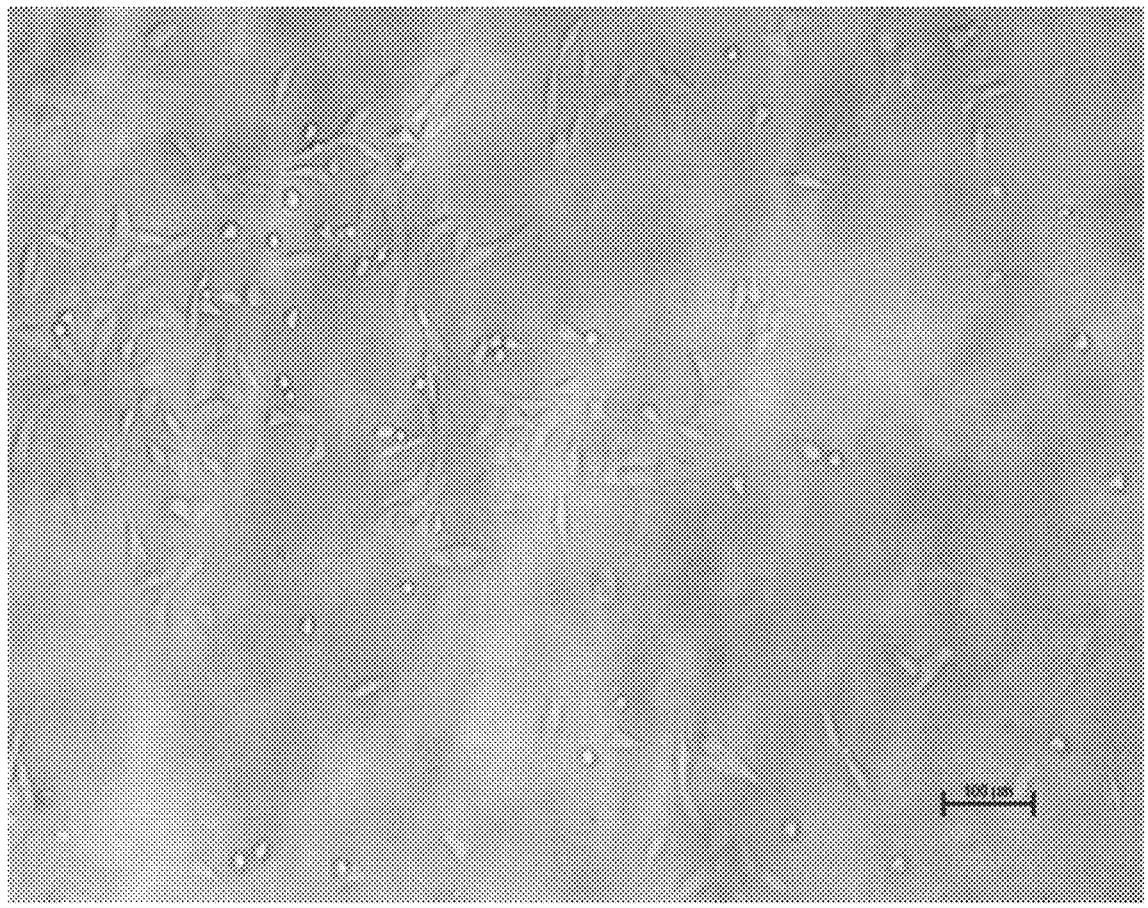
Figure 16E:
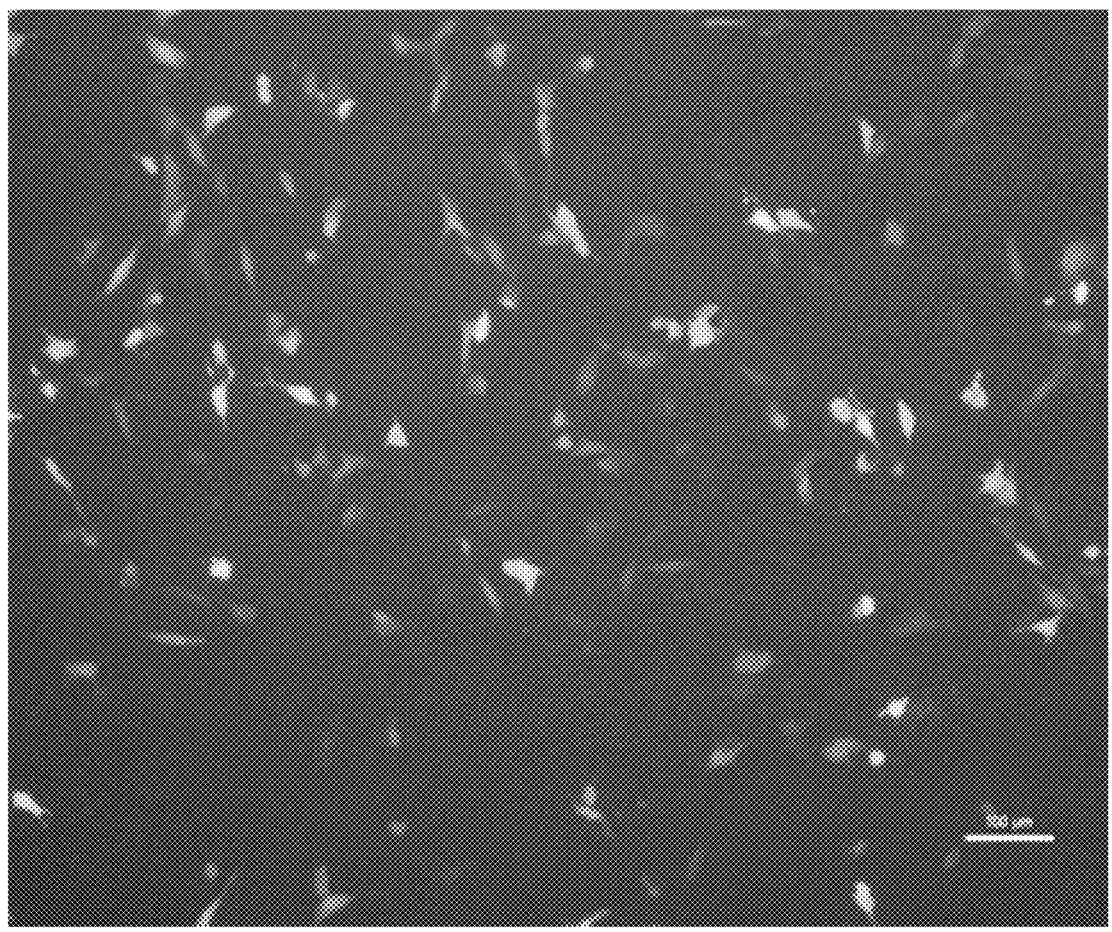
Figure 16F:
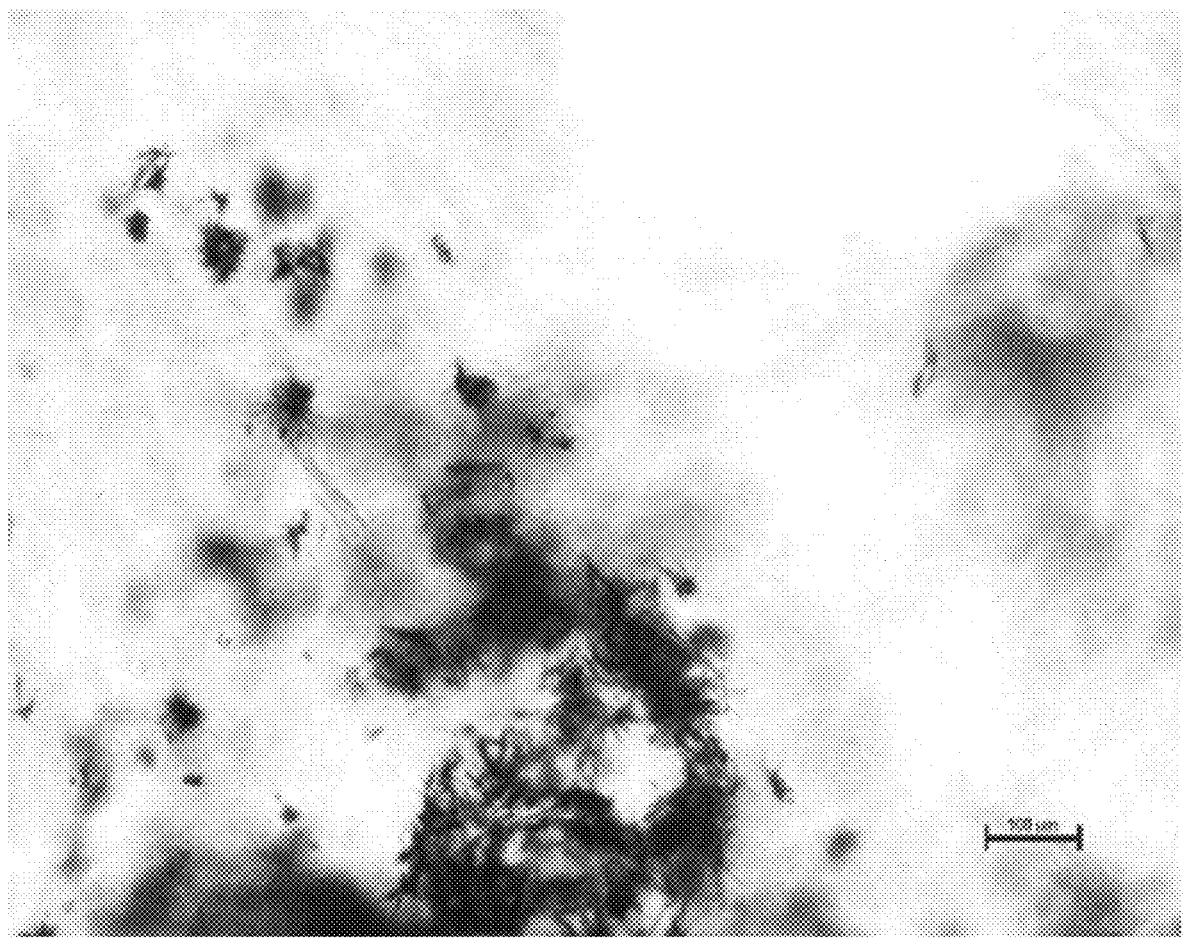
Figure 17A:
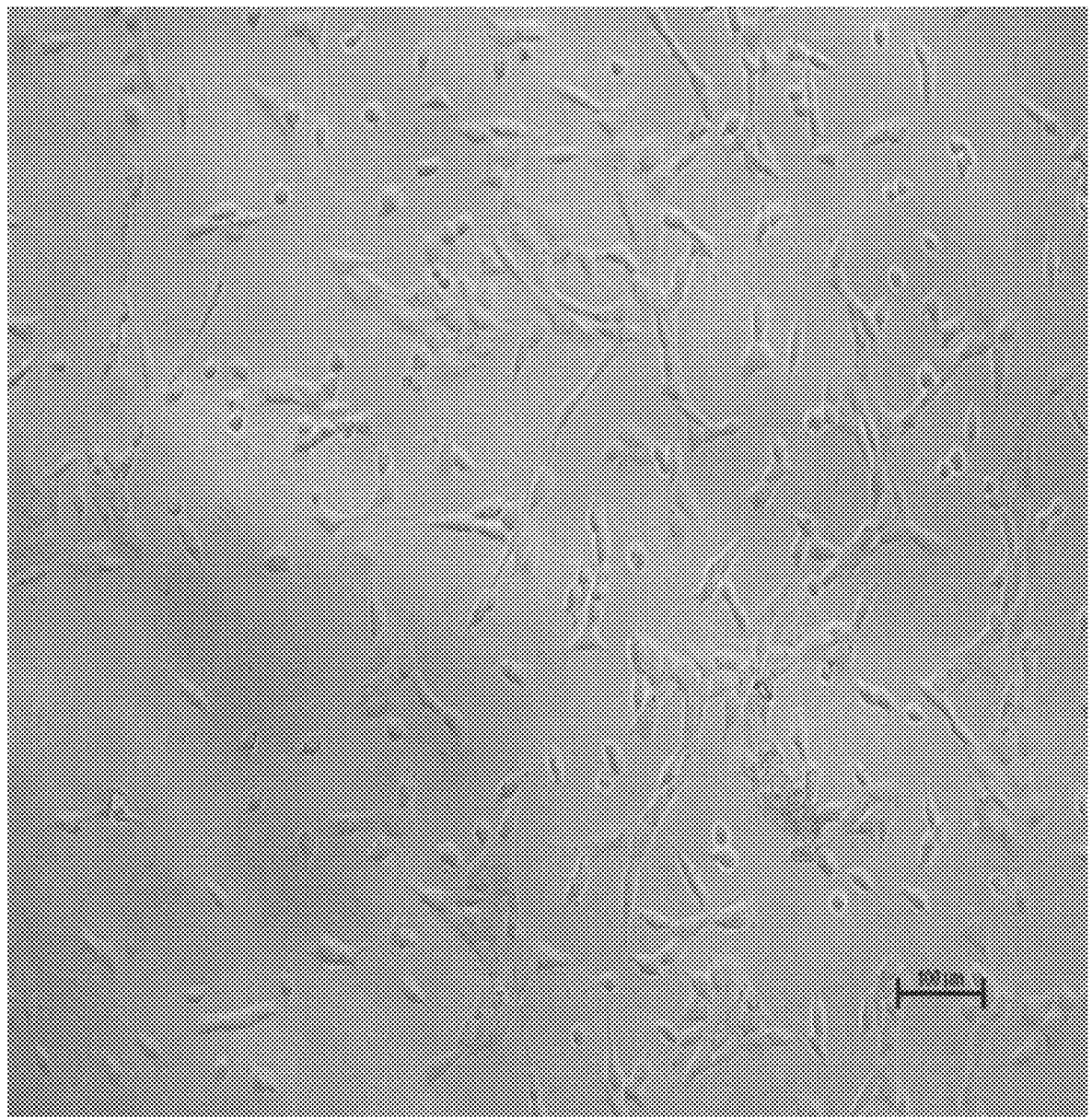
FIGS. 17A-17F show results of adherent growth of NIH/3T3 cells in α1 (II) and α1 (II) M6 collagen hydrogels, where
Figure 17B:
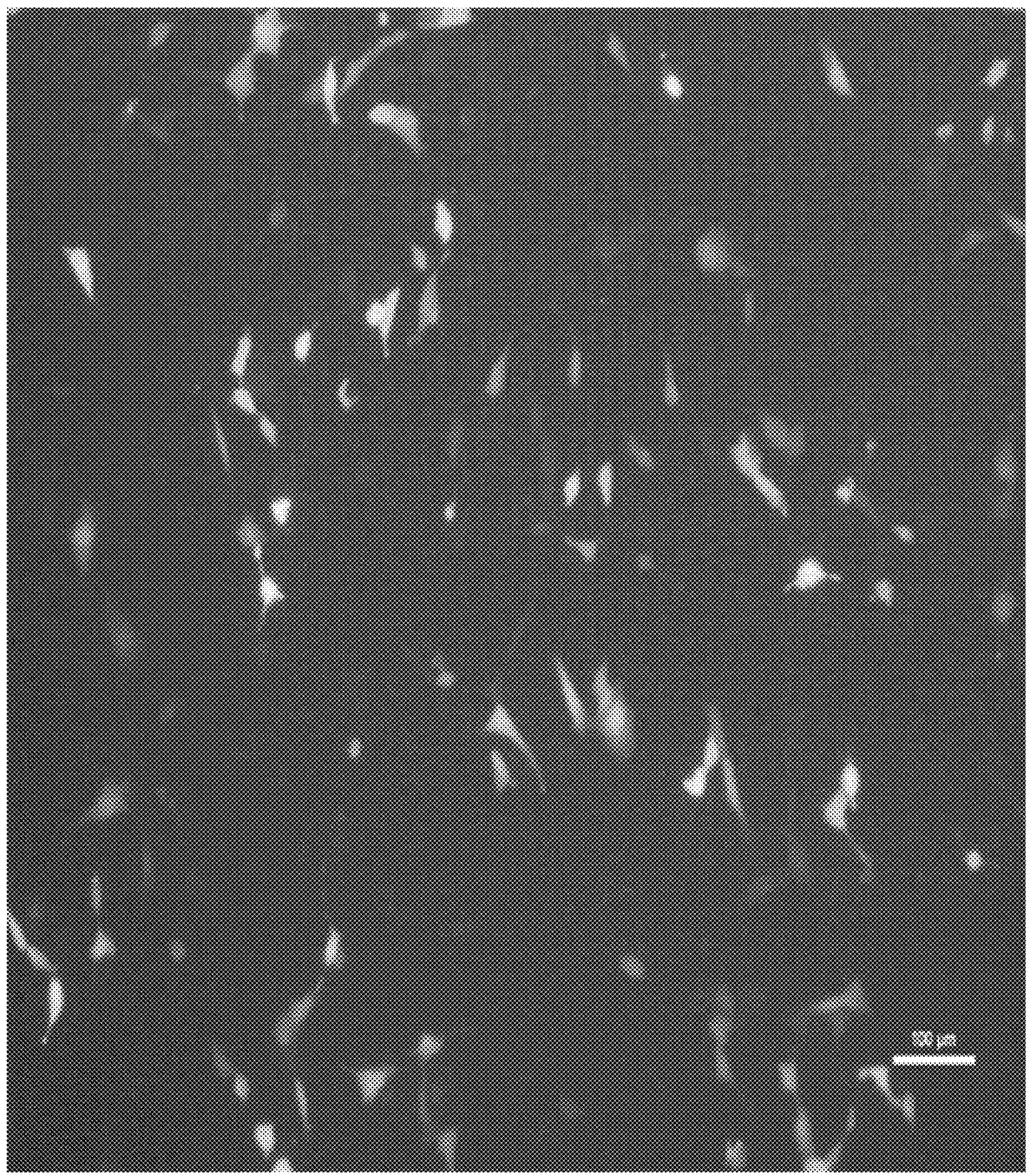
Figure 17C:
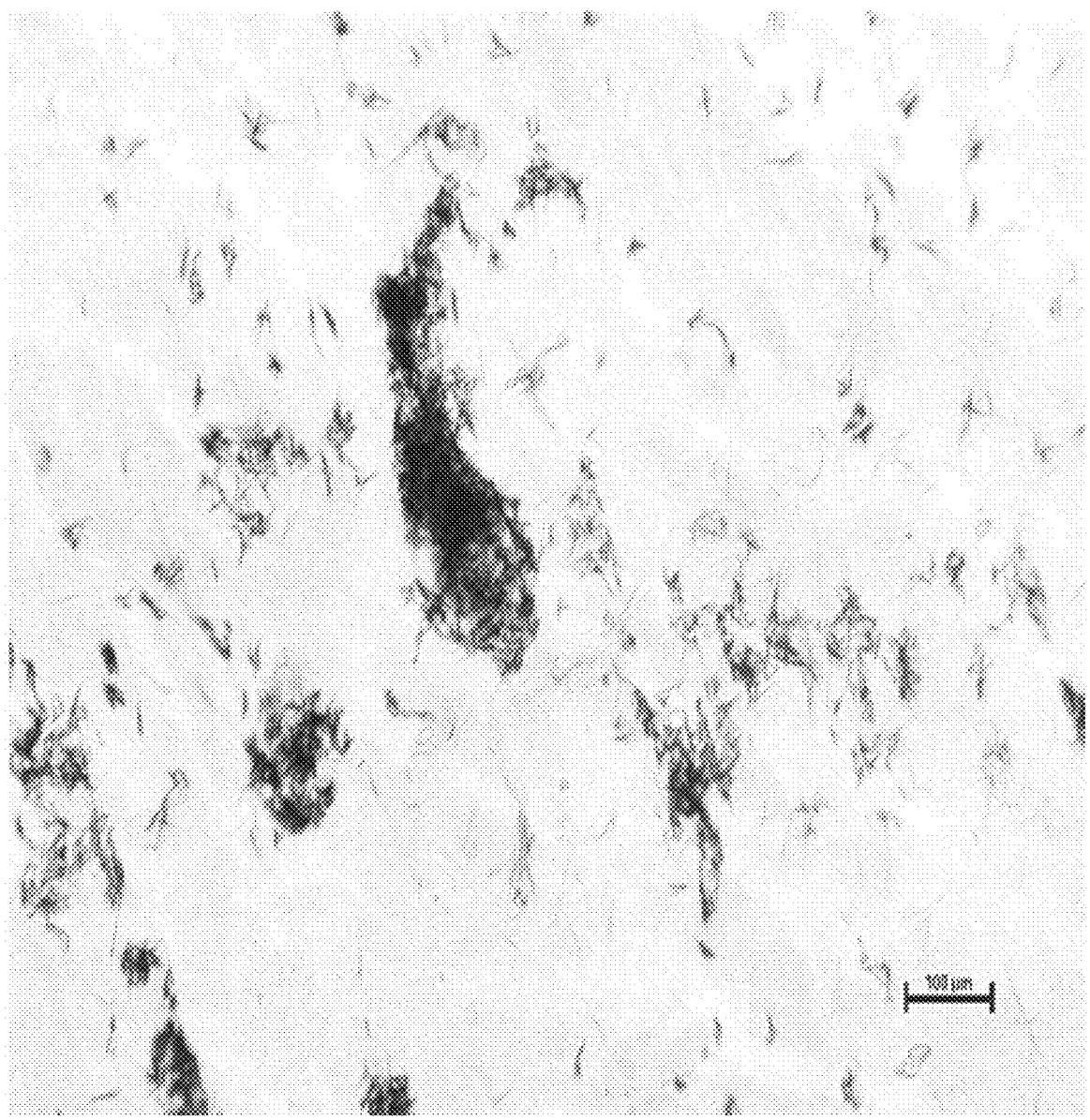
Figure 17D:
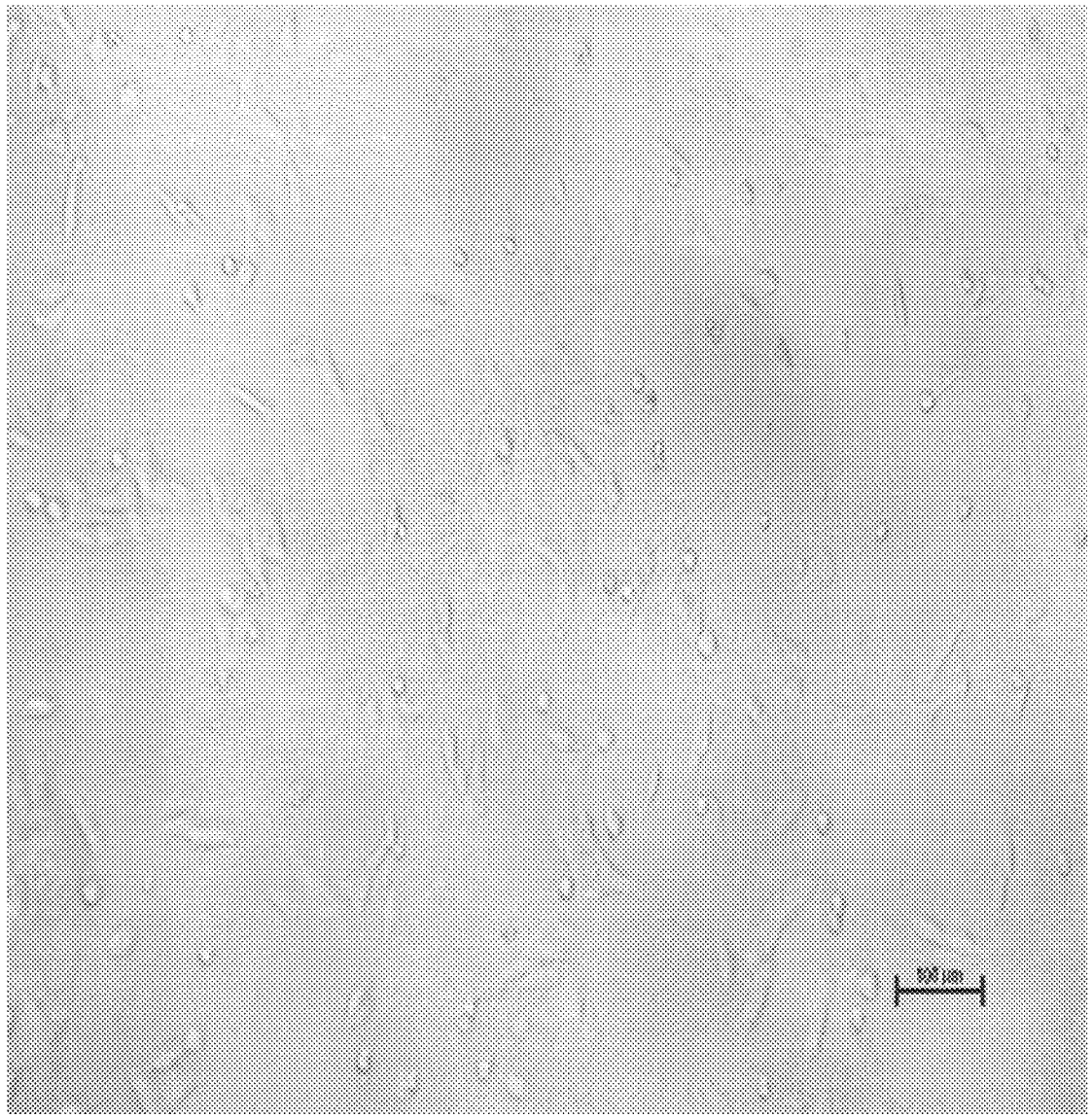
Figure 17E:
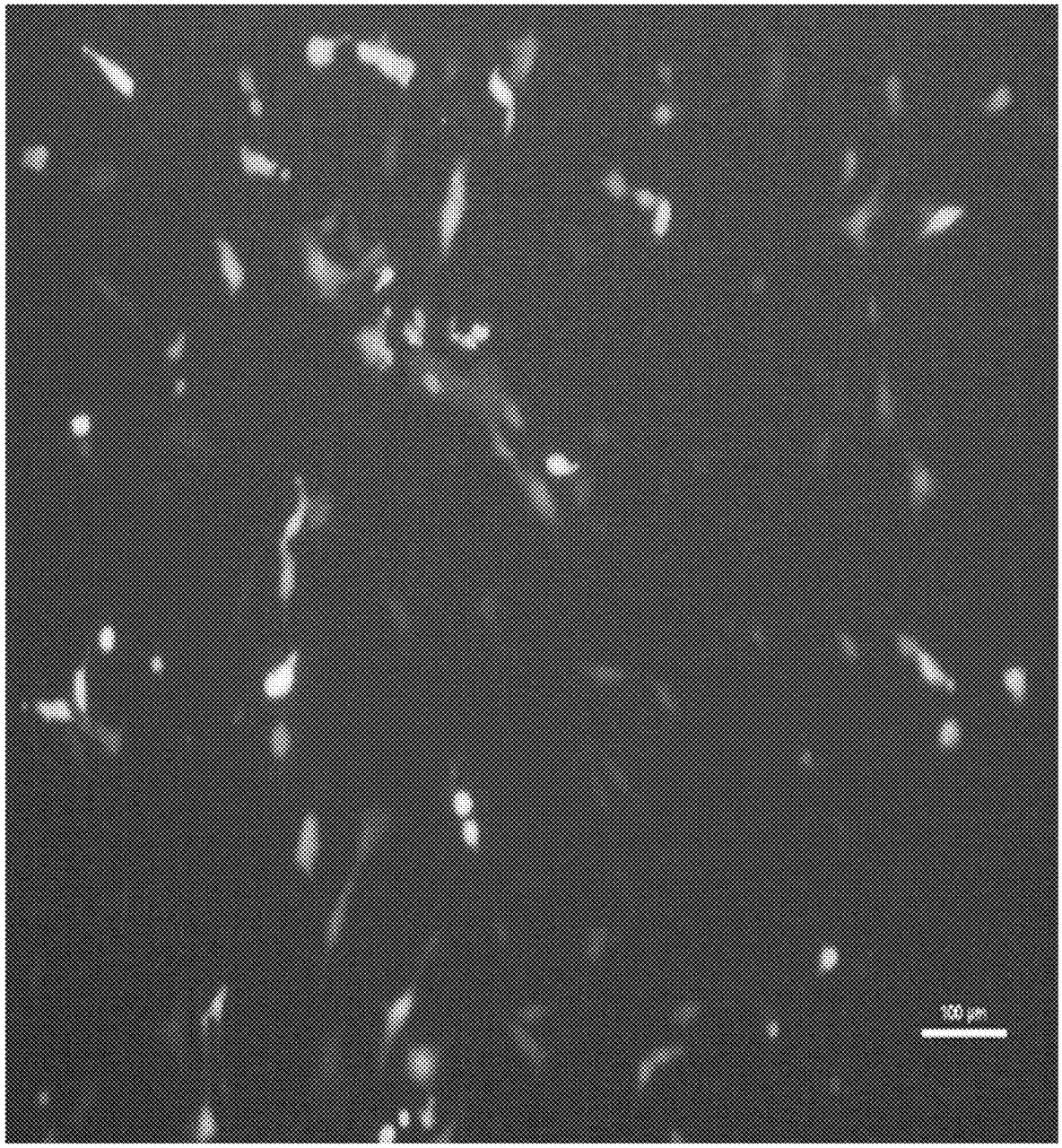
Figure 17F:
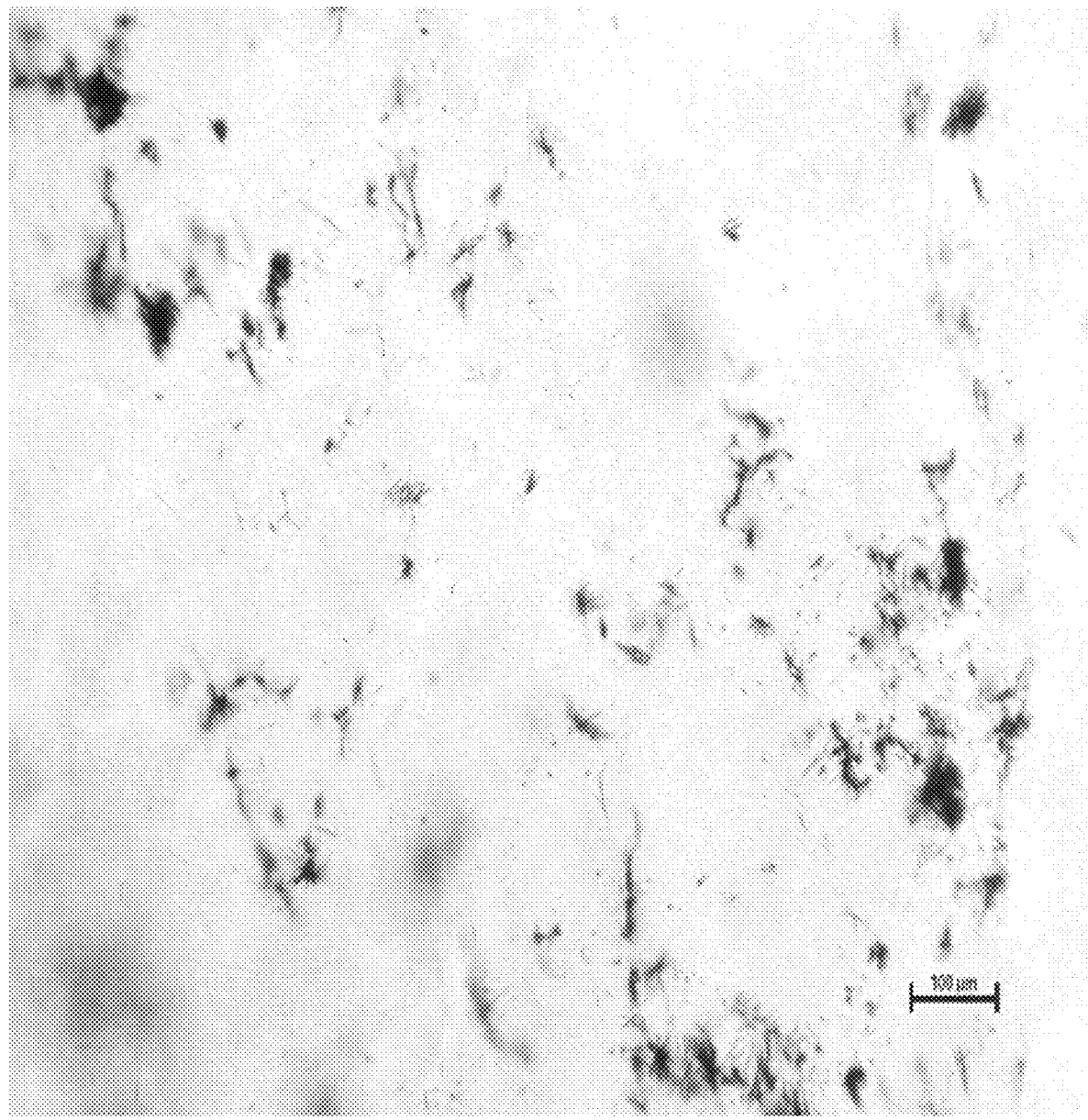

The absorbance $OD_{492\ nm}$ can correspondingly characterize a cell adhesion activity of a collagen sample. The higher the absorbance $OD_{492\ nm}$, the more the cells to which the collagen adheres and the higher the cell adhesion activity, such that the collagen is more likely to help cells adhere to a wall or adhere to an extracellular matrix in a short time, which is conducive to building an excellent extracellular environment. As shown in FIG. 13, the recombinant collagen α1 (I) M1, α1 (II) M6, α1 (I), and α1 (II) all have a similar cell adhesion activity to commercially available native human collagen, and all have a significantly higher cell adhesion activity than the control group, and there is no significant difference between α1 (I) M1 and α1 (I) and between α1 (II) M6 and α1 (II) in terms of the cell adhesion activity.

(3) Preparation and Detection of Recombinant Collagen Hydrogels

Recombinant collagens α1 (I) M1, α1 (II) M6, α1 (I), and α1 (II) each were taken and dissolved in water for injection at a concentration of 10% to obtain recombinant collagen solutions, a pH of the recombinant collagen solutions was controlled in a range of 4 to 6, and the recombinant collagen solutions were filtered through a 0.22 m sterile filter for sterilization; 0.1 g of a sterile 10% (w/w)N-hydroxysuccinimide (NHS) solution was added per 1 g of a dry collagen powder to obtain first mixed solutions, and first mixed solutions each were thoroughly mixed; then 0.13 g of a sterile 50% (w/w) 1-ethyl-3-(-3-dimethylaminopropyl) carbodiimide hydrochloride (EDC) solution was added per 1 g of a dry collagen powder to obtain second mixed solutions; and the second mixed solutions each were allowed to stand at room temperature (20° C. to 30° C.) to allow a reaction for 2 h to 6 h to obtain hydrogels. The hydrogels each were subjected to dialysis in a sterile PBS solution (NaCl: 8.5 g/L, $Na_2HPO_4$: 0.5 g/L, and $NaH_2PO_4$: 0.15 g/L, pH: 7.2) continuously for 120 h, where a ratio of a hydrogel to a PBS dialysis solution was 1:6 (m/m), and a PBS dialysis solution was completely changed every 24 h to remove NHS and EDC residues. Purified hydrogels produced after the dialysis each were filled in a sterile container and placed at room temperature.

The purified hydrogels each were lyophilized to remove moisture, weighed, then placed in a sterile PBS solution for 24 h until each hydrogel completely absorbed water and swelled, and then taken out. The moisture on a surface of each swollen hydrogel was removed with absorbent paper, and then the swollen hydrogel was weighed. A swelling ratio was calculated with reference to the method in the literature: $Q_{swelling\ ratio} = (W_{water\text{-}absorbed\ swollen\ gel\ weight} - W_{dry\ gel\ weight})/W_{dry\ gel\ weight}$. The elasticity modulus (storage modulus, small amplitude frequency scan, 25° C., stress: 0.5%, and 0.1 rad/s to 100.0 rad/s) and a dynamic viscosity (flow peak hold, 25° C., and shear rate: 2.0 s$^{-1}$) of a hydrogel were measured by a rheometer (Discovery HR-2). A lyophilized hydrogel was transferred to liquid nitrogen, quickly frozen, broken, and subjected to surface scanning by SEM (Hitachi TM3030PLUS). Elasticity modulus, dynamic viscosity, and swelling ratio results were shown in Table 2. There is no significant difference between hydrogels prepared from α1 (1) M1 and α1 (I) and between hydrogels prepared from α1 (II) M6 and al (II) under the same conditions in terms of hydrodynamic properties.

TABLE 2

Detection results of elasticity moduli, dynamic viscosities, and swelling ratios of four hydrogels

| Hydrogel type | Elasticity modulus (Pa) | Viscosity (Pa · S) | Swelling ratio (g/g of a dry hydrogel) |
|---|---|---|---|
| α1(II) | 104.63 | 82.87 | 14.18 |
| α1(II)M6 | 102.02 | 77.80 | 14.01 |
| α1(I) | 234.67 | 190.67 | 12.53 |
| α1(I)M1 | 292.68 | 170.97 | 12.22 |

As shown in FIGS. 14A-14D and FIGS. 15A-15D, hydrogels prepared from α1 (I) M1 and α1 (II) M6 are the same as hydrogels prepared from α1 (I) and α1 (II), respectively, and all have a porous network structure with a pore size in a range of 100 μm to 200 μm, excellent permeability, and a spatial structure basis for retaining a large amount of moisture. Thus, the hydrogels prepared from α1 (1) M1 and α1 (II) M6 can provide a space for adhesion, support, growth, and migration of cells and serve as a channel for delivering nutrients and metabolites, and have the potential of being used in the field of biomedical materials.

(4) Cell Detection of Recombinant Collagen Hydrogels

Hydrogels stored aseptically each were placed in a 24-well cell culture plate. NIH/3T3 cells cultivated normally purchased from the Cell Bank of the Chinese Academy of Sciences (Product No. GNM6, the cultivation and passage methods were performed according to instructions of the cells) were taken, washed with PBS, and digested with trypsin, then a medium was added to obtain a cell suspension, and the cell suspension was pipetted up and down for thorough mixing and then counted. The cell suspension was inoculated at $10^5$ cells/well into the cell culture plate coated with the hydrogels and cultivated for 24 h to 72 h, and the adhesion and proliferation of cells on the hydrogels were observed.

(1) A 24-well plate was taken, 1 mM Calcein AM (purchased from the Research Institute of Beyotime Biotechnology) solution was prepared with DMSO and diluted with D-PBS to obtain a 50 μM calcein working solution. The medium in wells of the cell culture plate was removed, and the wells were washed with PBS several times. Then I mL of a serum-containing DMEM medium and 100 L of the Calcein AM solution (¹⁄₁₀ of the medium) were added to the cell culture plate, and the cell culture plate was incubated for 30 min to allow the staining of cells. Then the medium was changed, the cells were cultivated for 30 min, and the hydrogel was gently taken out, placed in a new culture well, and photographed under a fluorescence microscope (a maximum excitation wavelength was 494 nm and a maximum emission wavelength was 514 nm).

(2) Another 24-well plate was taken, 200 μL of an MTT solution (purchased from the Research Institute of Beyotime Biotechnology) was added to the 24-well plate, the NIH/3T3 cells were cultivated for 4 h, and the production of blue-purple crystals in the cells was observed. The medium was discarded, and the hydrogel was washed with PBS, cut longitudinally, placed in a new culture well, and photographed under a microscope.

The experiments in this example were entrusted to the Functional Nanomaterials and Biomedical Testing Laboratory of School of Pharmacy, Changzhou University.

Results are shown in FIGS. 16A-16F and FIGS. 17A-17F. The hydrogels prepared from α1 (I) M1 and α1 (II) M6 are the same as the hydrogels prepared from α1 (I) and α1 (II), and NIH/3T3 cells have a normal morphology under a brightfield microscope, which is a typical fibroblast morphology. After NIH/3T3 cells growing adherently on a hydrogel are stained with Calcein AM, green fluorescence can be detected (bright parts in an image). After MTT is added to NIH/3T3 cells growing in a hydrogel, blue-purple crystals can be produced (dark parts in an image). The green fluorescence and the blue-purple crystals can only be produced by viable cells. It indicates that NIH/3T3 cells can adhere to, grow, and migrate normally in the hydrogels. The hydrogels prepared from α1 (I) M1 and α1 (II) M6 have similar biological functions to the hydrogels prepared from α1 (1) and α1 (II) with native sequences, and thus can be used as novel biomedical devices in fields such as wound healing and tissue regeneration.

What is claimed is:

1. A recombinant collagen α1 chain, wherein the recombinant collagen α1 chain is α1 (I) M1 or α1 (II) M6; the α1 (I) M1 is obtained through an amino acid mutation in a native full-length amino acid sequence of a human type I collagen α1 chain, and the α1 (II) M6 is obtained through an amino acid mutation in a native full-length amino acid sequence of a human type II collagen α1 chain; and the α1 (I) M1 has a sequence as set forth in SEQ ID NO: 2, and the α1 (II) M6 has a sequence as set forth in SEQ ID NO: 5.

2. A nucleotide sequence encoding the recombinant collagen α1 chain according to claim 1.

3. The nucleotide sequence according to claim 2, wherein the nucleotide sequence encoding the α1 (I) M1 is set forth in SEQ ID NO: 3; and the nucleotide sequence encoding the α1 (II) M6 is set forth in SEQ ID NO: 6.

4. A recombinant expression vector comprising the nucleotide sequence according to claim 2.

5. An engineered strain expressing the recombinant collagen α1 chain according to claim 1, wherein the engineered strain is *Pichia pastoris*.

6. The engineered strain according to claim 5, wherein the engineered strain is deposited in the China General Microbiological Culture Collection Center (CGMCC), with an accession number of CGMCC NO. 21891 or CGMCC NO. 21892, wherein the engineered strain with the accession number of CGMCC NO. 21891 expresses the recombinant collagen α1 chain α1 (I) M1, and the engineered strain with the accession number of CGMCC NO. 21892 expresses the recombinant collagen α1 chain α1 (II) M6.

7. A preparation method of the recombinant collagen α1 chain according to claim 1, comprising the following steps:
  (1) synthesizing a nucleotide sequence encoding the recombinant collagen α1 chain according to claim 1;
  (2) constructing a recombinant expression vector containing the nucleotide sequence from step (1);
  (3) constructing engineered strains by electrotransforming the recombinant expression vector from step (2) into competent cells, and screening the engineered strains to obtain an engineered strain with an expression of the recombinant expression vector from step (2);
  (4) cultivating the engineered strain from step (3) for a high-density fermentation to obtain a fermentation supernatant; and
  (5) purifying the fermentation supernatant, followed by lyophilization, to obtain the recombinant collagen α1 chain.

8. The preparation method according to claim 7, wherein the engineered strain is *Pichia pastoris*, and is deposited in the China General Microbiological Culture Collection Center (CGMCC), with an accession number of CGMCC NO. 21891 or CGMCC NO. 21892.

9. An article comprising the recombinant collagen α1 chain according to claim 1, wherein the article is selected from the group consisting of a drug, a medical device, a biological material, a tissue-engineered product, and a cosmetic.

10. The article according to claim 9, wherein the article is a material for providing an adhesion, a support, and a growth and migration space for a cell or a material serving as a channel for delivering a nutrient and a metabolite.

11. A collagen hydrogel comprising the recombinant collagen al chain according to claim 1.

12. The method according to claim 7, wherein the nucleotide sequence encoding the recombinant collagen α1 chain is the nucleotide sequence encoding the α1 (I) M1 is set forth in SEQ ID NO: 3; or the nucleotide sequence encoding the α1 (II) M6 is set forth in SEQ ID NO: 6.

* * * * *